(12) United States Patent
Miller et al.

(10) Patent No.: US 9,666,915 B2
(45) Date of Patent: May 30, 2017

(54) TRANSFER PRIORITY FOR A WIRELESS TRANSFER STATION

(71) Applicant: Enovate Medical, LLC, Murfreesboro, TN (US)

(72) Inventors: David R. Miller, Murfreesboro, TN (US); Mary Metelko, Murfreesboro, TN (US); Allen Kilbourne, Canton, MI (US)

(73) Assignee: Enovate Medical, LLC, Murfreesboro, TN (US)

( * ) Notice: Subject to any disclaimer, the term of this patent is extended or adjusted under 35 U.S.C. 154(b) by 305 days.

(21) Appl. No.: 14/323,410

(22) Filed: Jul. 3, 2014

(65) Prior Publication Data
US 2015/0364945 A1 Dec. 17, 2015

Related U.S. Application Data

(60) Provisional application No. 62/010,921, filed on Jun. 11, 2014.

(51) Int. Cl.
| | |
|---|---|
| *H02J 7/00* | (2006.01) |
| *H02J 7/14* | (2006.01) |
| *H01M 10/659* | (2014.01) |
| *H02J 5/00* | (2016.01) |
| *H02J 7/02* | (2016.01) |
| *H01M 10/658* | (2014.01) |
| *H01M 2/10* | (2006.01) |

(Continued)

(52) U.S. Cl.
CPC ....... *H01M 10/659* (2015.04); *H01M 2/1022* (2013.01); *H01M 2/1264* (2013.01); *H01M 2/348* (2013.01); *H01M 10/46* (2013.01); *H01M 10/482* (2013.01); *H01M 10/486* (2013.01); *H01M 10/658* (2015.04); *H02J 5/005* (2013.01); *H02J 7/007* (2013.01); *H02J 7/0021* (2013.01); *H02J 7/0047* (2013.01); *H02J 7/025* (2013.01); *H02J 17/00* (2013.01); *H04B 5/0037* (2013.01); *H04Q 9/00* (2013.01); *G01V 3/12* (2013.01); *H01M 2200/10* (2013.01); *H01M 2200/103* (2013.01); *H01M 2220/30* (2013.01); *Y10T 307/469* (2015.04)

(58) Field of Classification Search
USPC ....... 320/108, 103, 107, 137, 109, 138, 101, 320/106, 114, 124, 125, 141, 155, 160, 320/162, 165; 307/104, 149, 151, 39
See application file for complete search history.

(56) References Cited

U.S. PATENT DOCUMENTS

| | | | |
|---|---|---|---|
| 8,115,448 B2 * | 2/2012 | John | A61N 1/3785 320/108 |
| 8,663,106 B2 | 3/2014 | Stivoric et al. | |

(Continued)

*Primary Examiner* — Alexis A Boateng
(74) *Attorney, Agent, or Firm* — Nathan J. Bailey; Waller Lansden Dortch & Davis, LLP

(57) ABSTRACT

A technology for a wireless transfer station that is operable to wirelessly provide energy to other wireless transfer stations. A wireless transfer request can be received from one or more of the other wireless transfer stations to receive wireless energy from the wireless transfer station. A transferring of wireless energy to the one or more of the other wireless transfer stations can be prioritized using selected energy transfer priority criteria. Wireless energy can be provided to the one or more of the other wireless transfer stations based on the prioritization.

21 Claims, 37 Drawing Sheets

(51) Int. Cl.
*H01M 2/12* (2006.01)
*H01M 2/34* (2006.01)
*H01M 10/48* (2006.01)
*H04B 5/00* (2006.01)
*H02J 17/00* (2006.01)
*H04Q 9/00* (2006.01)
*H01M 10/46* (2006.01)
*G01V 3/12* (2006.01)

(56) References Cited

U.S. PATENT DOCUMENTS

| | | | | |
|---|---|---|---|---|
| 8,723,642 B2 * | 5/2014 | Park | ................ | G07F 15/006 320/103 |
| 8,772,979 B2 * | 7/2014 | Tsai | ................ | H02J 5/005 307/104 |
| 8,853,890 B2 * | 10/2014 | Suzuki | ................ | H04B 5/0037 307/104 |
| 2010/0181964 A1 * | 7/2010 | Huggins | ................ | H02J 17/00 320/108 |
| 2010/0244576 A1 * | 9/2010 | Hillan | ................ | G06K 7/0008 307/104 |
| 2011/0050164 A1 * | 3/2011 | Partovi | ................ | H01F 5/003 320/108 |
| 2012/0249051 A1 | 10/2012 | Son et al. | | |
| 2012/0280650 A1 * | 11/2012 | Kim | ................ | H02J 17/00 320/108 |
| 2013/0026981 A1 | 1/2013 | Van Der Lee | | |
| 2013/0117595 A1 | 5/2013 | Murawski et al. | | |
| 2013/0154557 A1 * | 6/2013 | Lee | ................ | H02J 7/0052 320/108 |
| 2013/0214735 A1 * | 8/2013 | Kang | ................ | H02J 7/025 320/108 |
| 2013/0221915 A1 * | 8/2013 | Son | ................ | H02J 7/025 320/108 |
| 2013/0234661 A1 * | 9/2013 | Yang | ................ | H02J 7/025 320/108 |
| 2013/0241474 A1 | 9/2013 | Moshfeghi | | |
| 2013/0249305 A1 * | 9/2013 | Kudo | ................ | H02J 17/00 307/104 |
| 2014/0002014 A1 | 1/2014 | Sultenfuss et al. | | |
| 2014/0253032 A1 * | 9/2014 | Bruwer | ................ | H02M 1/36 320/108 |
| 2014/0266024 A1 * | 9/2014 | Chinnadurai | ................ | B25H 3/00 320/108 |
| 2016/0028770 A1 | 1/2016 | Raleigh et al. | | |

\* cited by examiner

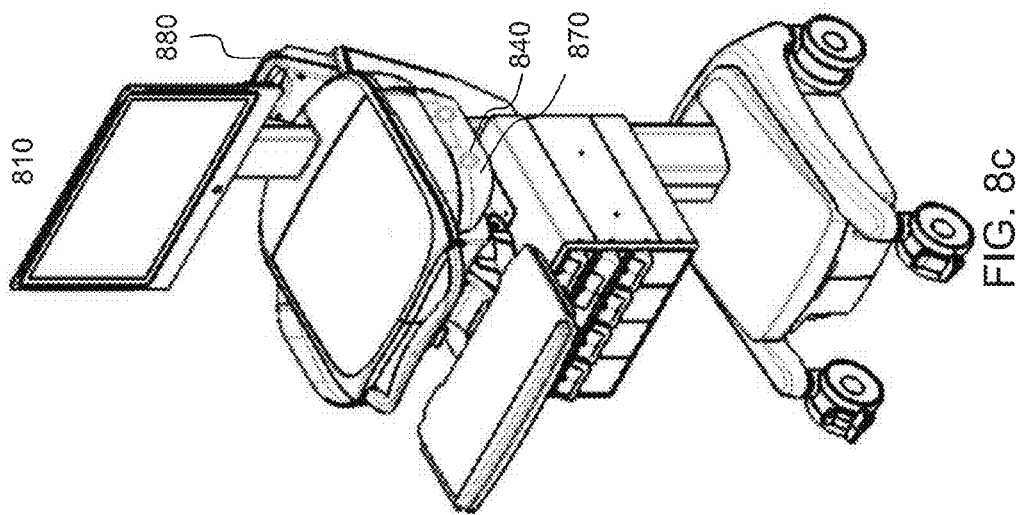
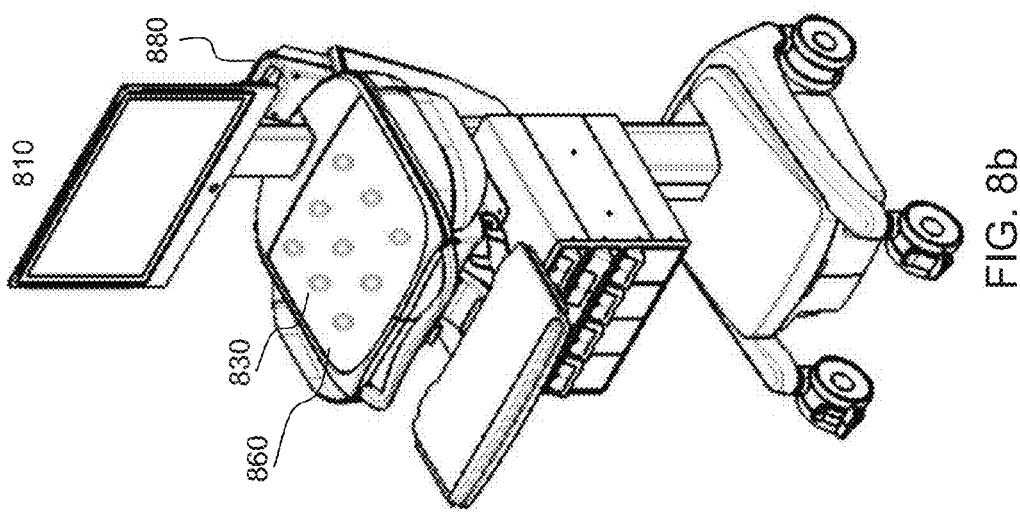
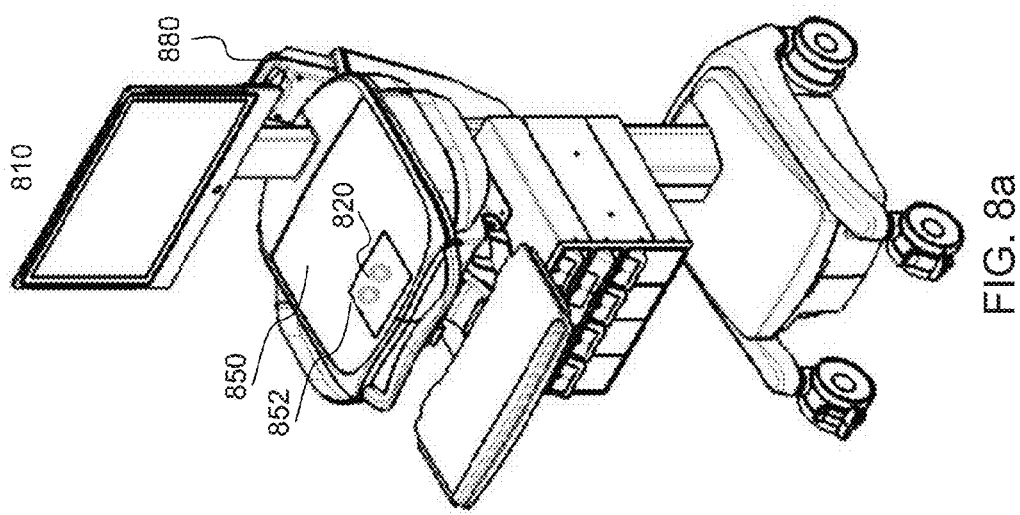

TRANSFER PRIORITY FOR A WIRELESS TRANSFER STATION

This application claims the benefit of and hereby incorporates by reference U.S. Provisional Patent Application Ser. No. 62/010,921, filed Jun. 11, 2014.

BACKGROUND

With an increase of electrical devices used in the transportation and communication markets, the energy industry is continually expanding to meet an increasing energy need. Typically, batteries can be broadly classified into two categories: primary batteries and secondary batteries. A primary battery, also known as a disposable battery, can be used once until the battery is depleted, after which the disposable battery can be replaced with a new battery. A secondary battery, also known as a rechargeable battery, can be capable of repeated recharging and reuse. One advantage of rechargeable batteries can be a cost advantage, environmental friendlier alternative, and an ease-of-use compared to disposable batteries. As the battery industry continues to grow, rechargeable batteries are taking an increasingly central role in meeting the needs of the various markets.

As a number of devices using rechargeable batteries increase, there is an increasing demand to recharge the rechargeable batteries more efficiently and rapidly. Charging a plurality of rechargeable batteries together can be useful to reduce a time period a user must wait before a charged battery is available. Reducing waiting period for users of rechargeable batteries can be important in environments where a large number of rechargeable batteries are used or where there is a high demand for the batteries. Additionally, efficiently managing the charging of a plurality of batteries can aid in balancing user demand with a health of each battery.

BRIEF DESCRIPTION OF THE DRAWINGS

Features and advantages of the disclosure will be apparent from the detailed description which follows, taken in conjunction with the accompanying drawings, which together illustrate, by way of example, features of the disclosure; and, wherein:

FIG. 8a depicts a wheeled medical cart with a plurality of wireless transfer stations integrated into a selected area of a work surface of the wheeled medical cart in accordance with an example;

FIG. 8b depicts a wheeled medical cart with a plurality of wireless transfer stations integrated into a work surface of the wheeled medical cart in accordance with an example;

FIG. 8c depicts a wheeled medical cart with one or more of wireless transfer stations integrated into a device holder of the wheeled medical cart in accordance with an example;

Figure 1:
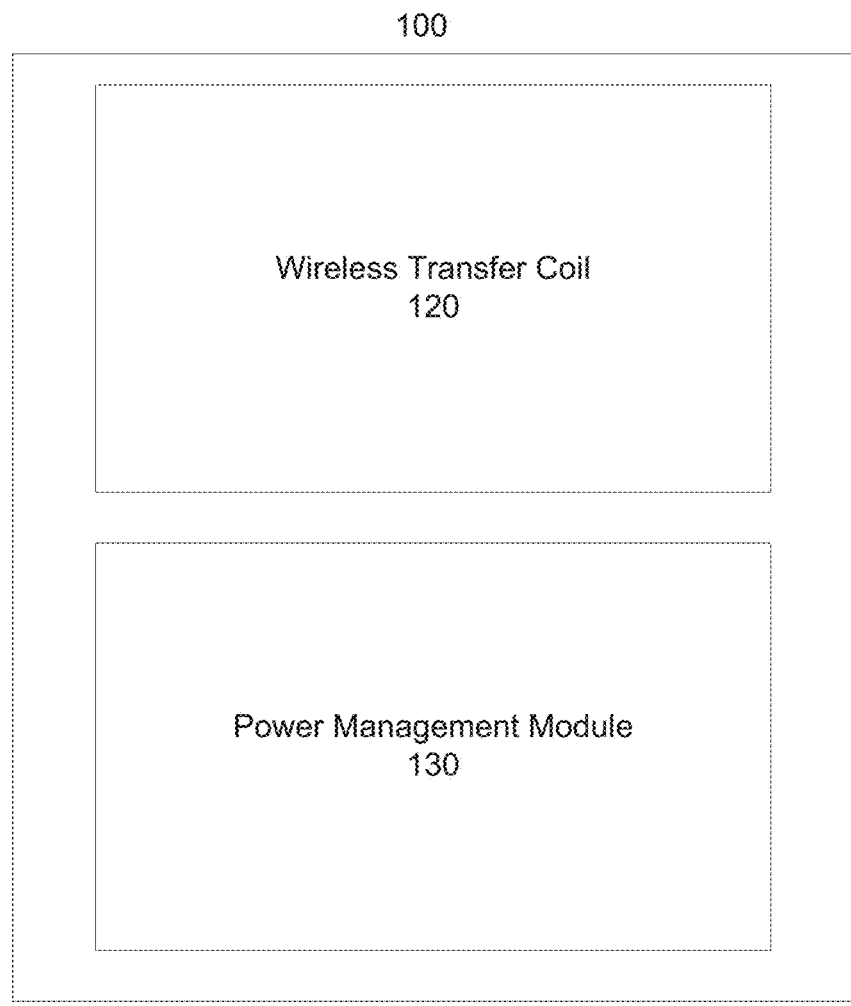
FIG. 1 depicts a wireless transfer station in accordance with an example.

Reference will now be made to the exemplary embodiments illustrated, and specific language will be used herein to describe the same. It will nevertheless be understood that no limitation of the scope of the invention is thereby intended.

DETAILED DESCRIPTION

Before the present invention is disclosed and described, it is to be understood that this invention is not limited to the particular structures, process steps, or materials disclosed herein, but is extended to equivalents thereof as would be recognized by those ordinarily skilled in the relevant arts. It should also be understood that terminology employed herein is used for the purpose of describing particular examples only and is not intended to be limiting. The same reference numerals in different drawings represent the same element. Numbers provided in flow charts and processes are provided for clarity in illustrating steps and operations and do not necessarily indicate a particular order or sequence.

The terms battery, cell, and/or battery cell as used herein can be used interchangeably and can refer to any of a variety of different cell chemistries and configurations. In one embodiment the cell chemistries and configurations can include, but are not limited to, lithium ion (e.g., lithium iron phosphate, lithium cobalt oxide, other lithium metal oxides, etc.), lithium ion polymer, nickel metal hydride, nickel cadmium, nickel hydrogen, nickel zinc, silver zinc, or other battery type/configurations.

The term battery pack as used herein can refer to one or more individual batteries contained within a single piece housing, or a multiple piece housing. The one or more individual batteries can be electrically interconnected in parallel and/or in series to achieve a selected energy level (such as a voltage level or a current level) and capacity level.

An increasing number and variety of electronic devices are powered using non-wired energy sources, such as batteries or wireless energy sources that provide power directly to the device or to energy storage systems. The electronic devices can range from mobile phones, portable music players, laptop computers, and tablet computers to medical devices such as hearing aids, pace makers, wheeled medical carts, medical measurement equipment, medical test equipment, and other types of medical equipment.

Traditionally, battery chargers operate to charge one or more batteries by either simultaneously charging one or more batteries of the same type using a single charging port or by charging each of the batteries of the same type simultaneously using multiple charging ports. Traditional battery chargers can only recharge one type of battery and do not account for individual characteristics of different types of batteries. The battery chargers are often limited in the type of battery they can recharge. In one example, a traditional battery charger can only provide a fixed voltage output and a fixed current output to a selected battery or type of battery with a selected energy level. Energy levels in batteries are typically measured in watt-hours or amp-hours.

Often, rechargeable batteries are used as a replenishable energy source for electronic devices. In one embodiment, a battery pack can include one or more rechargeable batteries. In one example, the one or more rechargeable batteries can be a lead-based battery, a lithium-based battery, a nickel based battery, or another type of chemical storage battery. Traditionally, a rechargeable battery pack provides energy to an electronic device using physical electrically conductive connections between the rechargeable battery pack and the electronic device. When the traditional rechargeable batteries of the rechargeable battery pack are depleted, the rechargeable batteries can be replenished by connecting physical electrically conductive contacts between the rechargeable battery pack and a battery charger.

In one embodiment of the present invention, a wireless transfer station can receive energy and/or send energy to another device, such as another wireless transfer station, using a wireless energy transfer scheme (e.g. transfer energy without wires). A wireless energy transfer scheme can be any form of wireless energy transfer associated with the use of electric fields, magnetic fields, electromagnetic fields, and so forth that allows electrical energy to be transmitted between two or more wireless transfer elements without using physical electrical contacts. In one example, a wireless energy transfer of wireless energy can be a transfer of electrical energy from an energy source to an electrical load without the use of interconnecting wires or physical electrical contacts.

In one embodiment, the wireless transfer station can include one or more wireless transfer coils to transfer energy and/or data with other wireless transfer stations. The wireless transfer coil can include one or more power management modules to control the energy transfers and/or data transfers with the other wireless transfer stations.

Examples of a wireless transfer station includes a wireless energy rechargeable battery pack, a wireless energy transfer platform and/or data transceiver integrated into a medical cart, a wireless energy transfer platform and/or data transceiver integrated into an electronic device, a wireless energy transfer platform and/or data transceiver integrated into a piece of furniture, a wireless energy transfer platform and/or data transceiver integrated into a plate mounted to a wall, a wireless energy transfer platform and/or data transceiver integrated into a device (such as a medical device or medical equipment), and so forth.

In one example, the wireless transfer station can be a wireless energy battery pack that can be attached to a device, such as a medical cart or medical equipment. The wireless transfer station that transfers energy and/or data with the device can also relay the energy and/or data with other devices and/or wireless transfer stations. These examples are not intended to be limiting. The wireless transfer station can be implemented in a variety of electronic devices and mounting locations.

In one embodiment, the wireless transfer station can receive data from and/or send data or information to another device, such as another wireless transfer station, using a wireless data transfer scheme. In another embodiment, the wireless data transfer scheme can be any form of data transfer associated with a communications network. In another embodiment, the communications network can be a cellular network. The cellular network can be configured to operate based on a cellular standard, such as the third generation partnership projection (3GPP) long term evolution (LTE) Rel. 8, 9, 10, 11, or 12 standard, or the institute of electronic and electrical engineers (IEEE) 802.16p, 802.16n, 802.16m-2011, 802.16h-2010, 802.16j-2009, or 802.16-2009 standard.

In another embodiment, the communications network can be a wireless local area network (such as a wireless fidelity network (Wi-Fi)) that can be configured to operate using a standard such as the IEEE 802.11-2012, IEEE 802.11ac, or IEEE 802.11ad standard. In another embodiment, the communications network can be configured to operate using a Bluetooth standard such as Bluetooth v1.0, Bluetooth v2.0, Bluetooth v3.0, or Bluetooth v4.0. In another embodiment, the communications network can be configured to operate using a ZigBee standard, such as the IEEE 802.15.4-2003 (ZigBee 2003), IEEE 802.15.4-2006 (ZigBee 2006), or IEEE 802.15.4-2007 (ZigBee Pro) standard. In another embodiment, the wireless data transfer scheme can be any form of data transfer associated with electric fields, magnetic fields, or electromagnetic fields that is transmitted between two or more wireless transfer elements without using physical electrical contacts.

In one embodiment, the wireless transfer station can include one or more wireless transfer elements. In one example, a wireless transfer element can be a wireless transfer coil. In one embodiment, the wireless transfer coil can be a coil used for transmitting and/or receiving energy and/or data using magnetic inductance and/or magnetic resonance.

FIG. 1 illustrates a wireless transfer station 110. FIG. 1 further illustrates that the wireless transfer station 110 can include a wireless transfer coil 120 and a power management module 130. In one example, the power management module 130 can convert energy received from an energy source, such as another wireless transfer station or an alternating current (AC) energy outlet, a selected current level, a selected voltage level, and/or a selected wattage level. In another embodiment, the wireless transfer station 110 can include one or more batteries, such as rechargeable batteries. In one embodiment, the wireless transfer coil 120 can comprise a transmitting coil and/or a receiving coil.

Figure 2:
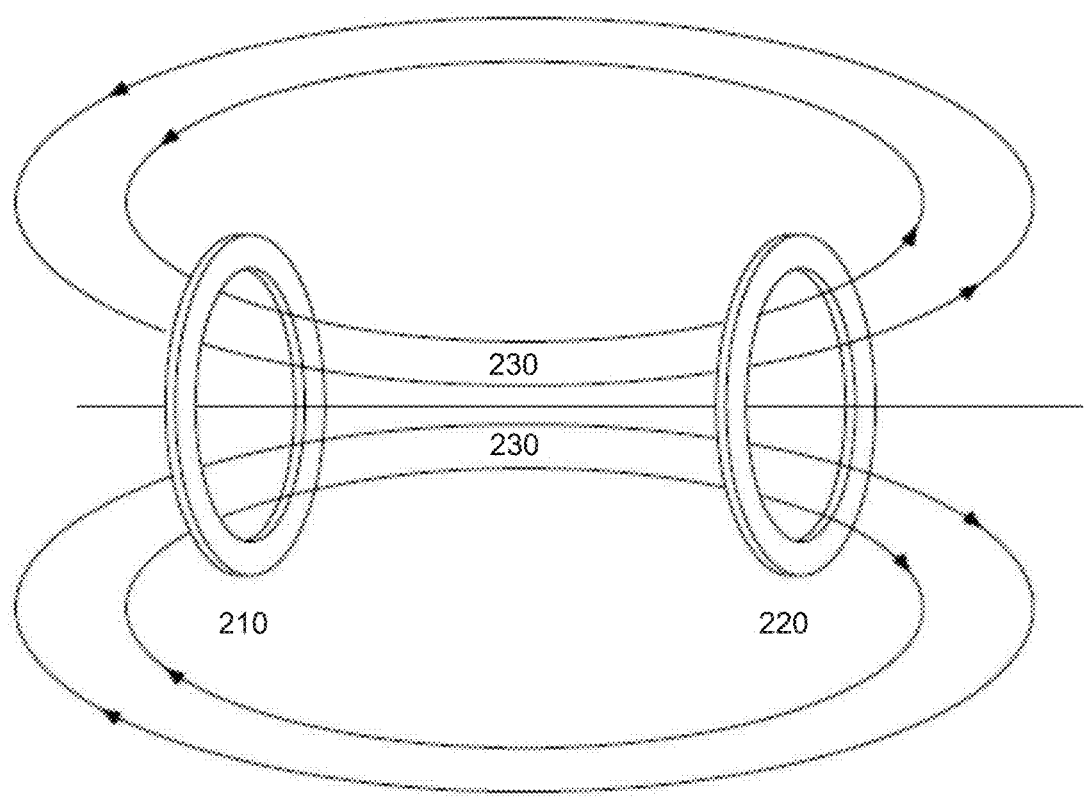
FIG. 2 depicts transferring energy or data between a plurality of wireless transfer coils in accordance with an example.

FIG. 2 illustrates an example of transferring energy or data between a plurality of wireless transfer coils 210 and 220. FIG. 2 further illustrates that one of the plurality of wireless transfer coils 210 can be a transmitting coil 210 and another one of the plurality of wireless transfer coils 220 can be a receiving coil 220. In one embodiment, energy and/or data can be transferred from the transmitting coil 210 to the receiving coil 220 by coupling the transmitting coil 210 with the receiving coil 220 to enable the energy or data to be transferred over a gap or distance. In one example, wireless energy can be transferred by generating a magnetic field 230 (such as an electromagnetic field) at the transmitting coil 210 and positioning the receiving coil 220 within the magnetic field 230 to induce a current at the receiving coil 220. The process of inducing a current at the receiving coil is referred to as coupling the receiving coil 220 to the transmitting coil 210. In one embodiment, the wireless transfer coil coupling for wireless energy or data transfer can be a magnetic induction coupling. In another embodiment, the wireless transfer coil coupling for wireless energy transfer can be a magnetic resonant coupling.

In one embodiment, the transmitting coil 210 can be a transmitting induction coil and the receiving coil 220 can be a receiving induction coil. The wireless transfer station can use a magnetic field to transfer energy between the transmitting coil 210 coupled to a first object (such as a wireless transfer station) and a receiving coil 220 of a second object (such as another wireless transfer station) without any direct contact between the transmitting coil 210 and the receiving coil 220, e.g. inductive coupling.

In one embodiment, inductive coupling can occur when the transmitting coil 210 creates a magnetic field 230 (such as an alternating electromagnetic field) using an energy source, such as an alternating current (AC) energy outlet or a direct current (DC) battery. A current can be induced at the receiving coil 220 using the magnetic field when the receiving coil 220 is located within the magnetic field 230.

In one example, when the transmitting coil 210 and the receiving coil 220 are within a threshold proximity distance, the transmitting coil 210 and the receiving coil 220 can couple to form an electric transformer. In one embodiment, current from the receiving coil 220 can be transferred to a battery or an electronic device. In another embodiment, the current can be stored in one or more energy sources of the wireless transfer station, such as a battery. In another embodiment, the current can be transferred to a device coupled to the wireless transfer station. In one embodiment, an impedance of one or more transmitting coils 210 can be substantially matched with an impedance of one or more receiving coils 220.

In one embodiment, the transmitting coil 210 can be a transmitting resonant coil and the receiving coil 220 can be a receiving resonant coil. A wireless resonant transfer can be a resonant transmission of energy or data between at least one transmitting coil 210 and at least one receiving coil 220. In another embodiment, at least one transmitting coil 210 and at least one receiving coil 220 can be tuned to resonate at a same frequency or a substantially same frequency.

In one example, resonant transmission of wireless energy can occur when the transmitting coil and the receiving coil are constructed to resonate at the same frequency or approximately the same frequency. The transmitting coil 210 can be configured to oscillate current at the resonant frequency of the coils to transfer energy and/or data. The oscillating current of the transmitting coil 210 can generate an oscillating magnetic field at the selected resonant frequency of the receiving coil. When the receiving coil 220 is positioned adjacent to the oscillating magnetic field and constructed to operate at the same frequency or substantially the same frequency as the transmitting coil 210, the receiving coil 220 can receive energy and/or data from the oscillating magnetic field.

In another embodiment, an impedance of one or more transmitting coils 210 can be substantially matched with an impedance of one or more receiving coils 220 for energy and/or data transfer. In another embodiment, the transmitting coil and the receiving coil can be positioned such that the receiving coil is within the near field of the magnetic field of the transmitting coil. The near field can be based within the Fraunhofer region, which can be approximately within $1/2\pi$ times the wavelength of the electromagnetic field.

One advantage of placing the receiving coil within the near field for wireless energy transfer is to reduce an amount of energy that may be radiated or leaked from the wireless transfer coils 210 and 220, e.g. energy not received at the receiving coil 220. In one embodiment, energy in a magnetic field falls off as the inverse squared of a distance ($1/d^2$) between the transmitting coil 210 and the receiving coil 220 within the near field. In one example, magnetic resonant coupling can be used to transfer energy at relatively high energy levels between the transmitting coil 210 and the receiving coil 220 and to minimize or reduce energy leaking away from the wireless transfer coils 210 and 220.

Another advantage of using a near field or a non-radiating field for wireless energy transfer can be that the near field or the non-radiating field can be used in areas adjacent to biological material, such as humans or other biological entities, with minimal or no effects to the biological material from the wireless energy transfer. In another embodiment, a wireless transfer station, such as in FIG. 1, can use a radio frequency (RF) signal, ultrasound, and/or laser beams to wirelessly transfer energy and/or data between a transmitting device and a receiving device.

Figure 3A:
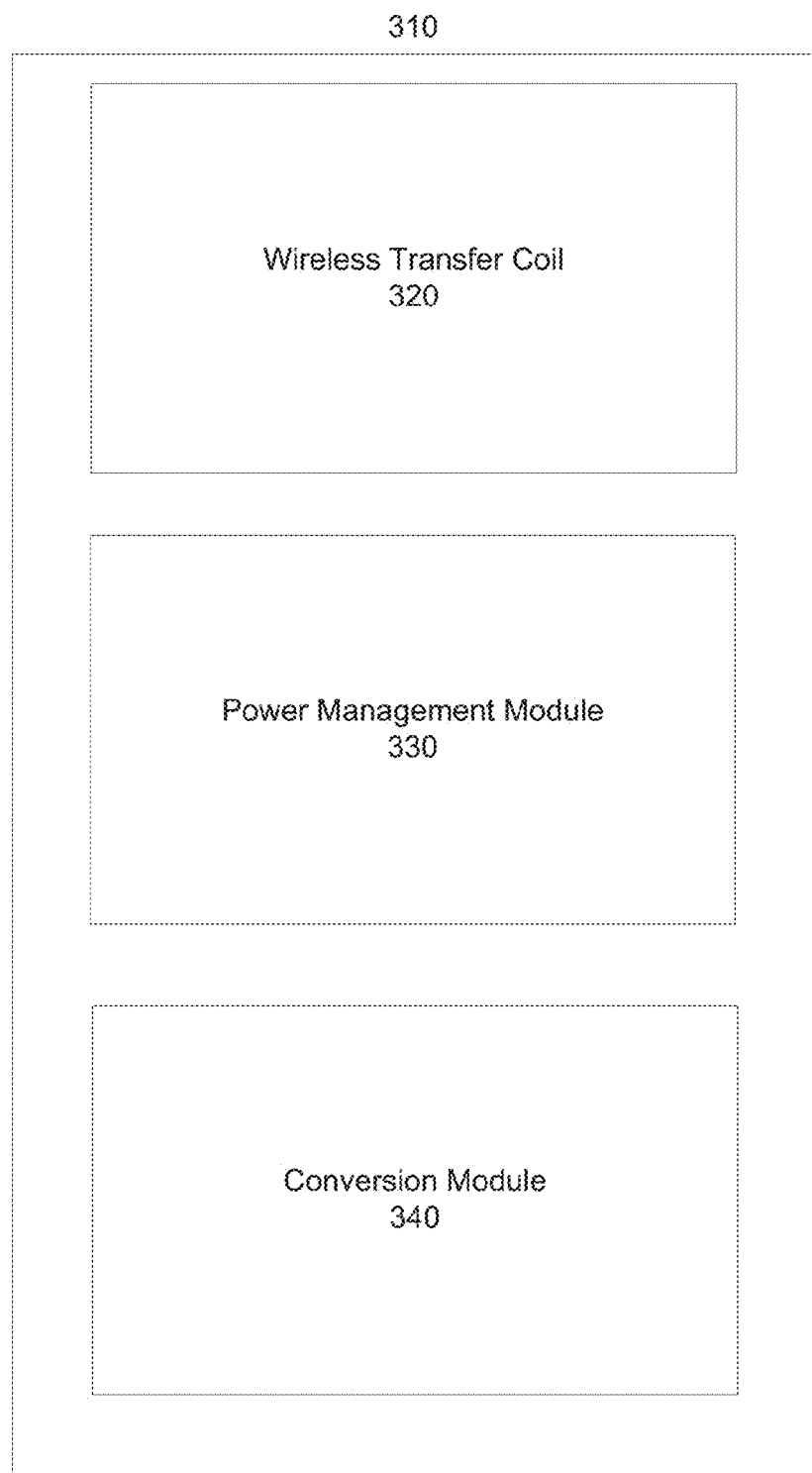
FIG. 3a depicts a wireless transfer station in accordance with an example.

FIG. 3a shows a wireless transfer station 310 that can include: a wireless transfer coil 320, a power management module 330, and a conversion module 340. In one embodiment, the wireless transfer coil 320 can be used for resonance coupling and/or induction coupling. In one example, the conversion module 340 can be coupled to the wireless transfer coil 320 and used to switch the wireless transfer coil 320 from a resonance mode (i.e. transferring wireless energy and/or data using magnetic resonance coupling) to an induction mode (i.e. transferring wireless energy and/or data using magnetic induction coupling), or vice versa.

In one embodiment, the wireless transfer coil 320 of the wireless transfer station 310 can be used for transmitting wireless energy and/or receiving wireless energy. In one example, the conversion module 340 can be coupled to the wireless transfer coil 320 and used to switch the wireless transfer coil 320 from a receiving mode (i.e. receiving wireless energy and/or data) to a transmitting mode (i.e. transmitting wireless energy and/or data), or vice versa.

In one embodiment, when the conversion module 340 of the wireless transfer station 310 is in the transmitting mode, the conversion module 340 or the power management module 330 can convert energy received from an energy source (such as a power outlet or a battery) at a selected voltage into a high frequency alternating current and transmit the high frequency alternating current to a wireless transfer coil of another wireless transfer station. The high frequency alternating current can flow through one or more loops of the wireless transfer coil 320 and create a varying magnetic field that can induce a current in the other wireless transfer coil. In another embodiment, when the conversion module 340 is switched to the receiving mode, a varying magnetic field from another wireless transfer station can induce an alternating current flowing through the one or more loops of the wireless transfer coil 320. The current flowing through the one or more loops can be converted into a direct current (DC) by the conversion module 340 or the power management module 330 and directed to a battery coupled to the wireless transfer station 310 or a device that is electrically coupled to the wireless transfer station 310.

In one embodiment, each wireless transfer coil 320 of a wireless transfer station 310 can be coupled to a separate conversion module 340. In another embodiment, one or more conversion modules 340 can be coupled to one or more selected groups of wireless transfer coils 320. One advantage of using a conversion module 340 for switching a wireless transfer coil 320 between transmitting mode and receiving mode can be to reduce a complexity of design and/or size of a wireless transfer station 310 by reducing a number of wireless transfer coils 320 used to transmit and/or receive wireless energy. Another advantage of using a conversion module 340 for switching a wireless transfer coil between a transmitting mode and receiving mode is to provide a dual functionality to a wireless transfer station of both transmitting and receiving wireless energy.

Figure 3B:
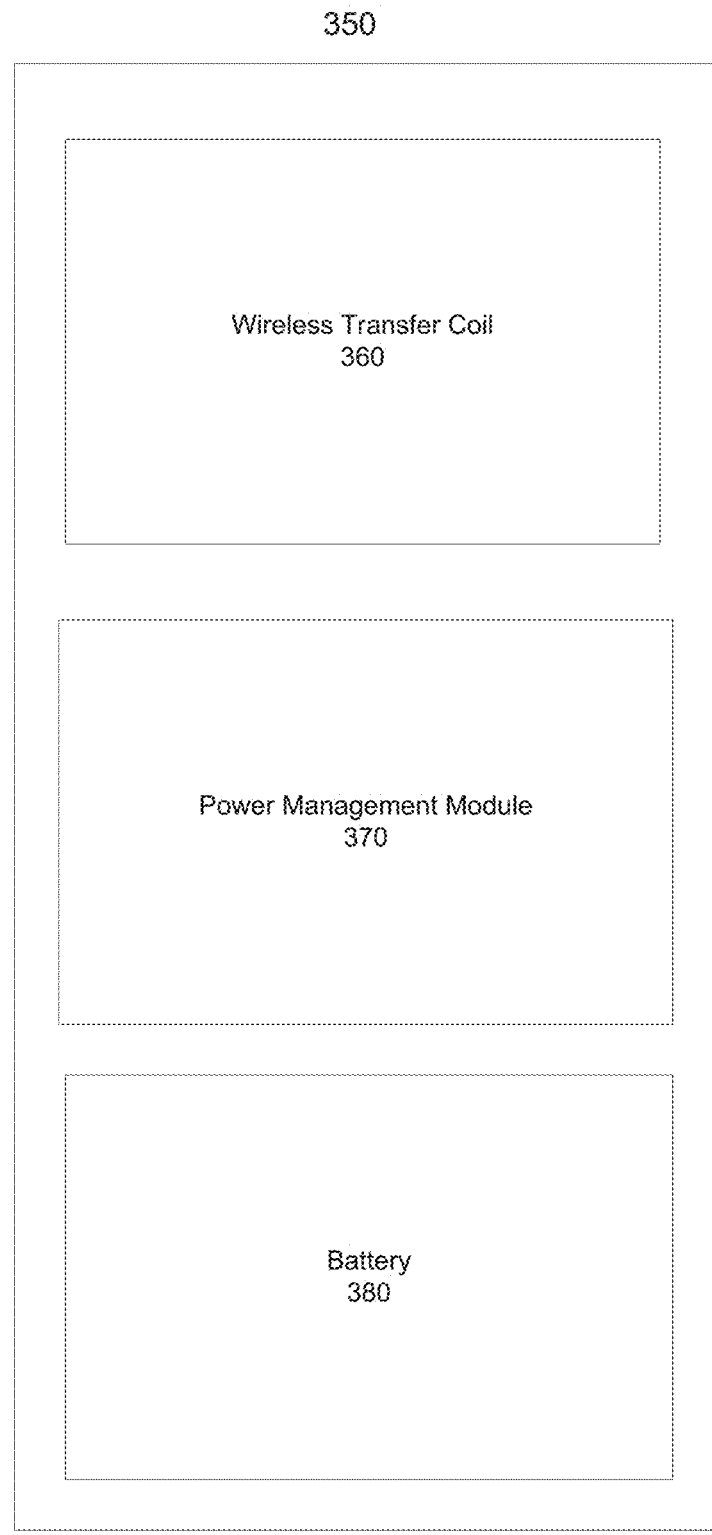
FIG. 3b depicts another wireless transfer station in accordance with an example.

FIG. 3b illustrates a wireless transfer station 350. FIG. 3b further illustrates that the wireless transfer station 350 can include: a wireless transfer coil 360; a power management module 370; and a battery 380. The battery 380 can comprise a plurality of batteries, such as rechargeable batteries. In one example, the power management module 370 can convert energy received using the wireless transfer coil 360 from an energy source, such as another wireless transfer station or an alternating current (AC) energy outlet, to a selected current level at a selected voltage level to provide a selected wattage level. In one embodiment, the power management module can transfer the converted energy to the battery 380 to store the energy.

Figure 3C:
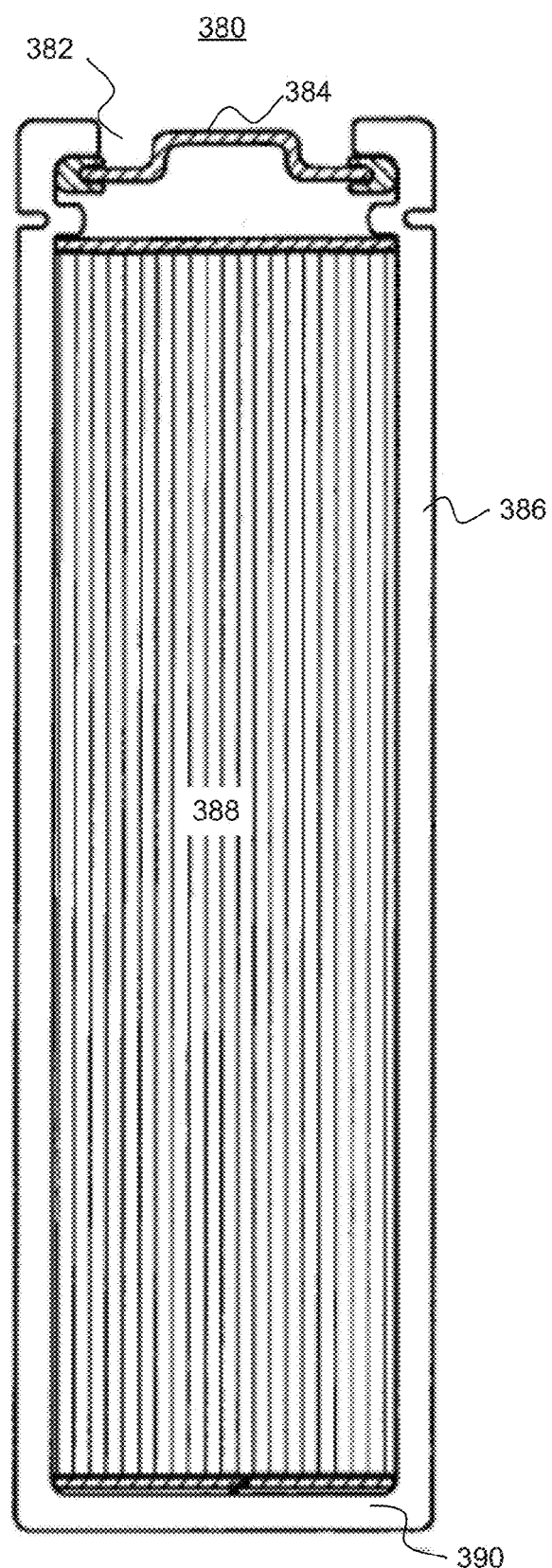
FIG. 3c depicts a cross-sectional view of a battery in accordance with an example.

FIG. 3c shows a cross-sectional view of a battery 380, for example a lithium ion battery utilizing an 18650 battery form-factor. The battery 380 can include: a case 386, such as a cylindrical case; one or more electrodes 388, and a cap 384. In one embodiment, the case 386 can be made of a metal, such as nickel-plated steel, that can be non-reactive with battery materials, such as an electrolyte or the one or more electrodes 388. In one embodiment, a bottom surface 390 of the case 386 can be seamlessly integrated with the remainder of the case 386. In one embodiment, a top end 382 of the case 386 can be open ended. In another embodiment, the cap 384 can be located at the top end 382 of the case 386. In another embodiment, the top end 382 can be a positive electrical terminal of the battery 380 and the bottom end 390 can be a negative electrical terminal. In one example, the positive electrical terminal and the negative electrical terminal of the battery 380 can be connected to a wireless transfer station to provide energy to the wireless transfer station. In another embodiment, a plurality of batteries can be connected in series and/or in parallel. In one embodiment, the battery 380 can be connected to a power management module, such as the power management modules in FIGS. 3a and 3b.

Figure 4:
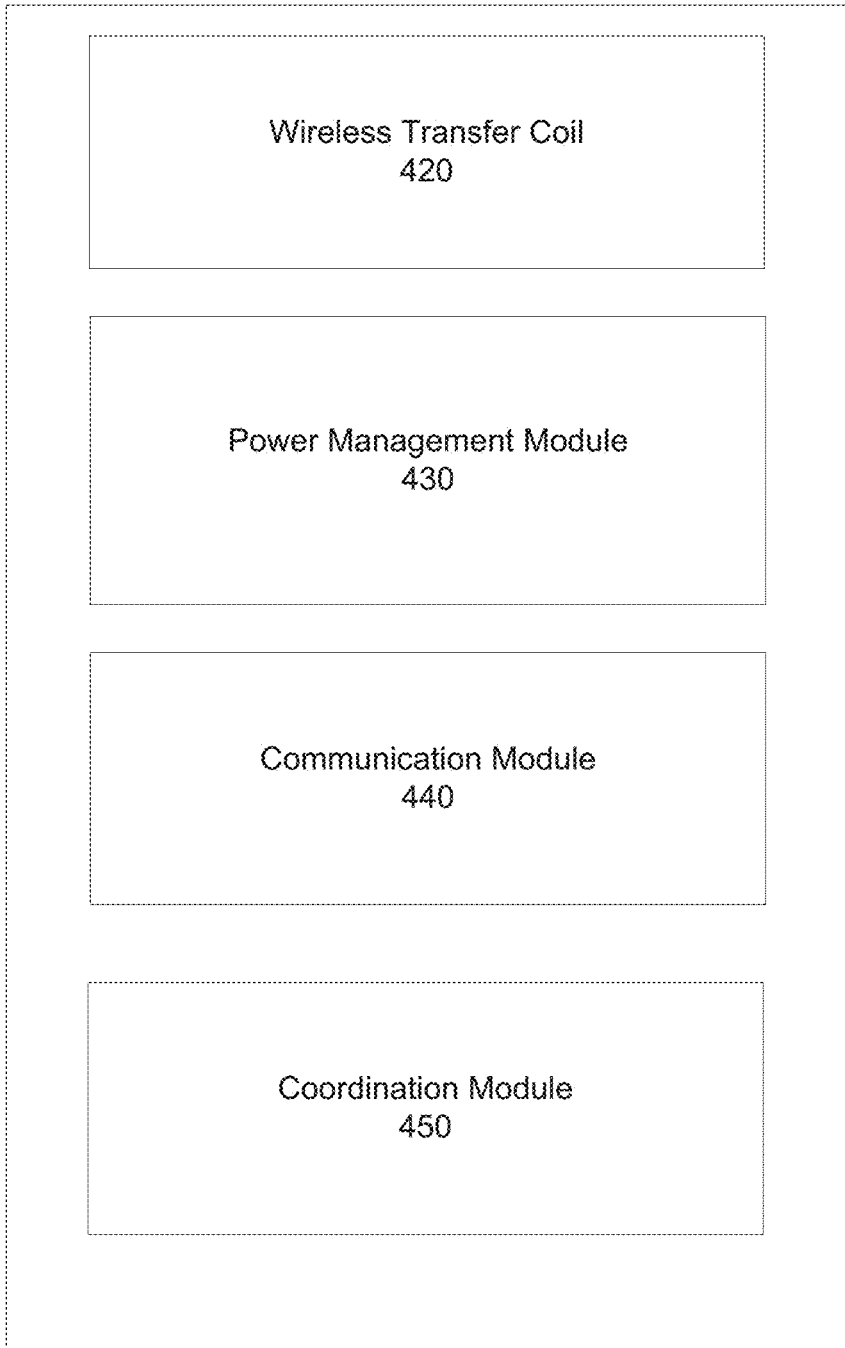
FIG. 4 depicts a wireless transfer station in accordance with an example.

FIG. 4 shows a wireless transfer station 410 that can include: a wireless transfer coil 420, a power management module 430, a communications module 440, and/or a coordination module 450. In one embodiment, the wireless transfer station 410 can communicate with one or more other wireless transfer stations or one or more devices using the communication module 440.

In one embodiment, the communication module 440 of the wireless transfer station 410 can use a communications network to communicate the data to a device and/or another wireless transfer station. In another embodiment, the communications network can be a cellular network that may be a 3GPP LTE Rel. 8, 9, 10, 11, or 12 or IEEE 802.16p, 802.16n, 802.16m-2011, 802.16h-2010, 802.16j-2009, 802.16-2009. In another embodiment, communications network can be a wireless network (such as a wireless fidelity network (Wi-Fi)) that may follow a standard such as the Institute of Electronics and Electrical Engineers (IEEE) 802.11-2012, IEEE 802.11ac, or IEEE 802.11ad standard. In another embodiment, the communications network can be a Bluetooth connection such as Bluetooth v1.0, Bluetooth v2.0, Bluetooth v3.0, or Bluetooth v4.0. In another embodiment, the communications network can be a ZigBee connection such as IEEE 802.15.4-2003 (ZigBee 2003), IEEE 802.15.4-2006 (ZigBee 2006), IEEE 802.15.4-2007 (ZigBee Pro).

In one embodiment, the wireless transfer station 410 can transfer energy to one or more other wireless transfer stations, receive energy from one or more other wireless transfer stations, and/or communicate data or information with one or more other wireless transfer stations. In another embodiment, the coordination module 450 of the wireless transfer station 410 can coordinate when energy is transferred between wireless transfer stations and/or when data is communicated between wireless transfer stations. In another embodiment, the coordination module 450 can use the communications module 440 to communicate with one or more other wireless transfer stations to coordinate energy and/or data transfer between the wireless transfer station 410 and the one or more other wireless transfer stations.

One advantage of transferring energy and/or data using a wireless transfer station 410 is to provide a single connection point between the wireless transfer station 410 and other wireless transfer stations and/or other devices. Another advantage of transferring energy and/or data using the wireless transfer station 410 can be to enable a single step for both transferring energy between the wireless transfer station 410 and other wireless transfer stations and communicating or synchronizing data communicated between the wireless transfer station 410 and other wireless transfer stations. In one example, when a first wireless transfer station (such as a wireless transfer station integrated into a medical cart) is located adjacent to a second wireless transfer station (such as a wireless transfer station integrated into a plate mounted to a wall or a floor mat), the first wireless transfer station can both receive energy from the second wireless transfer station and synchronize information with the second wireless transfer station.

In one embodiment, the coordination module 450 can communicate with a conversion module, as in FIG. 3*a*, to coordinate when one or more wireless transfer coils 420 of the wireless transfer station 410 can transmit and/or receive wireless energy and/or data. In one example, the coordination module 450 communicates with a conversion module, as in FIG. 3*a*, to coordinate transmitting and/or receiving wireless energy and/or data by coordinating when one or more wireless transfer coils 420 are in a transmitting mode or a receiving mode, as discussed in the preceding paragraphs.

Figure 5A:
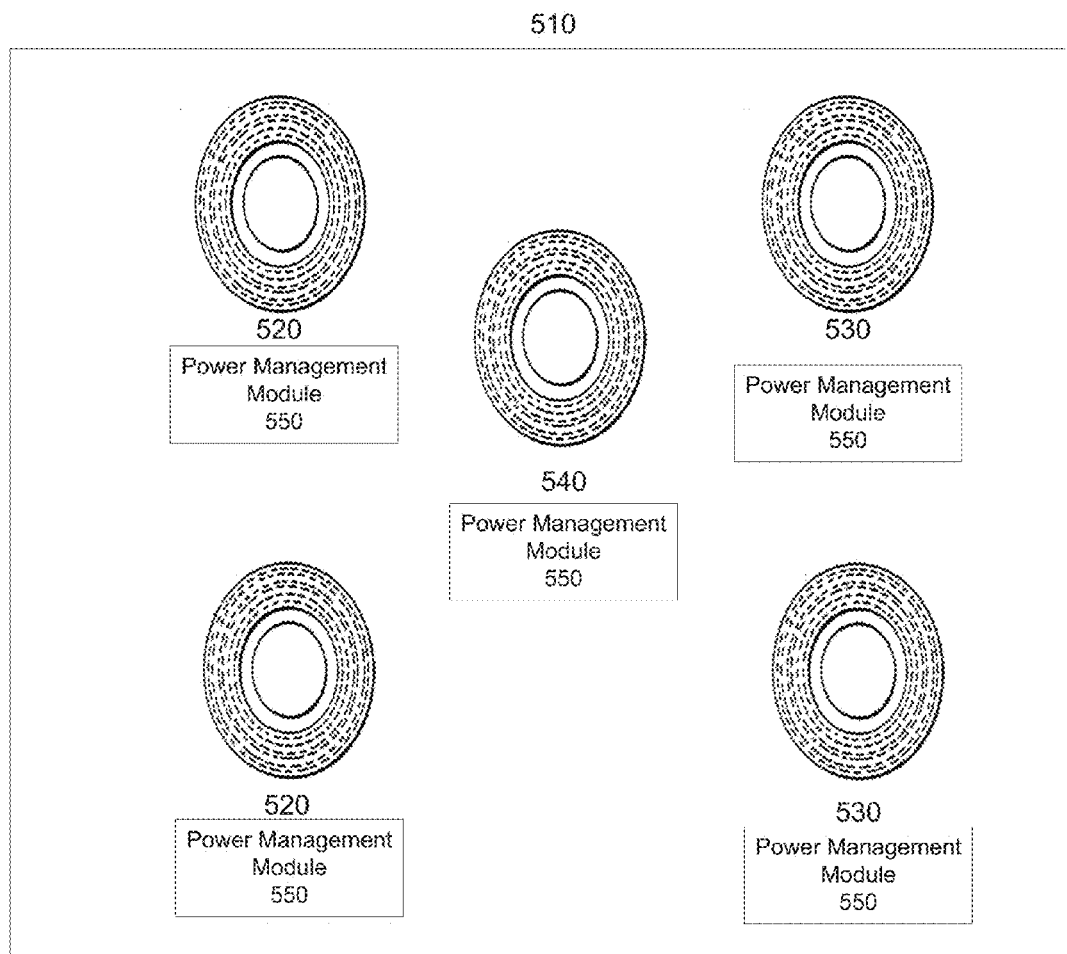
FIG. 5a depicts a wireless transfer station that includes one or more resonant wireless transfer coils and/or one or more induction wireless transfer coils in accordance with an example.

FIG. 5*a* shows a wireless transfer station 510 that includes one or more resonant wireless transfer coils 520 and/or one or more induction wireless transfer coils 530. In one example, the wireless transfer station 510 can have a resonant wireless transfer coil 520 and can transfer energy to a resonant wireless transfer coil of a first wireless transfer station and can have an induction wireless transfer coil 530 and can transfer energy to an induction wireless transfer coil of a second wireless transfer station. One advantage of the wireless transfer station having both resonant wireless transfer coils 520 and induction wireless transfer coils 530 can be to provide energy and/or data to wireless transfer stations and/or devices with only one of the resonant wireless transfer coils or the induction wireless transfer coils, thereby enabling more devices to transfer energy to the wireless transfer station.

In one embodiment, a device or another wireless transfer station can include one or more resonant wireless transfer coils and/or one or more induction wireless transfer coils. In one embodiment, the device or the other wireless transfer station receiving energy from the wireless transfer station 510 can select whether to receive wireless energy from the one or more resonant wireless transfer coils 520 or the one or more induction wireless transfer coils 530 of the wireless transfer station 510. In another embodiment, the wireless transfer station 510 can be configured to select whether to transmit wireless energy using the one or more resonant wireless transfer coils 520 or the one or more induction wireless transfer coils 530. In one example, a resonant transmitting coil and a resonant receiving coil pair can have a higher energy transfer efficiency than an induction transmitting coil and an induction receiving coil pair. In this example, when the device or the other wireless transfer station includes a resonant receiving coil, the other wireless transfer station and/or the device or the wireless transfer station 510 can be configured to use one or more resonant wireless transfer coils to perform an energy transfer.

In one embodiment, the one or more resonant wireless transfer coils 520 and/or the one or more induction wireless transfer coils 530 can be transmitting coils and/or receiving coils. In another embodiment, the wireless transfer station 510 can include one or more repeater coils 540. In one example, the repeater coil 540 can enhance wirelessly transmitted energy of a transmitting coil, e.g. providing additional transmission energy. In another example, the repeater coil 540 can receive the wireless energy from a transmitting coil and relay or retransmit the received energy to another repeater coil 540 or to a receiving coil. The repeater coils can be configured as inductive repeater coils or resonant repeater coils, and associated with transmit coils and receive coils of the same kind.

In one embodiment, the one or more resonant wireless transfer coils 520, the one or more induction wireless transfer coils 530, and/or the repeater coil 540 can include a power management module 550 configured to covert energy from an energy source to a varying magnetic field. In another embodiment, the one or more resonant wireless transfer coils 520, the one or more induction wireless transfer coils 530, and/or the repeater coil 540 can be coupled to a power management module 550 configured to convert a magnetic field into energy, such as energy at a selected current level, a voltage level, a wattage level, and/or an amperage level, and transfer the energy to a battery of the wireless transfer station 510 or a device coupled to the wireless transfer station 510.

Figure 5B:
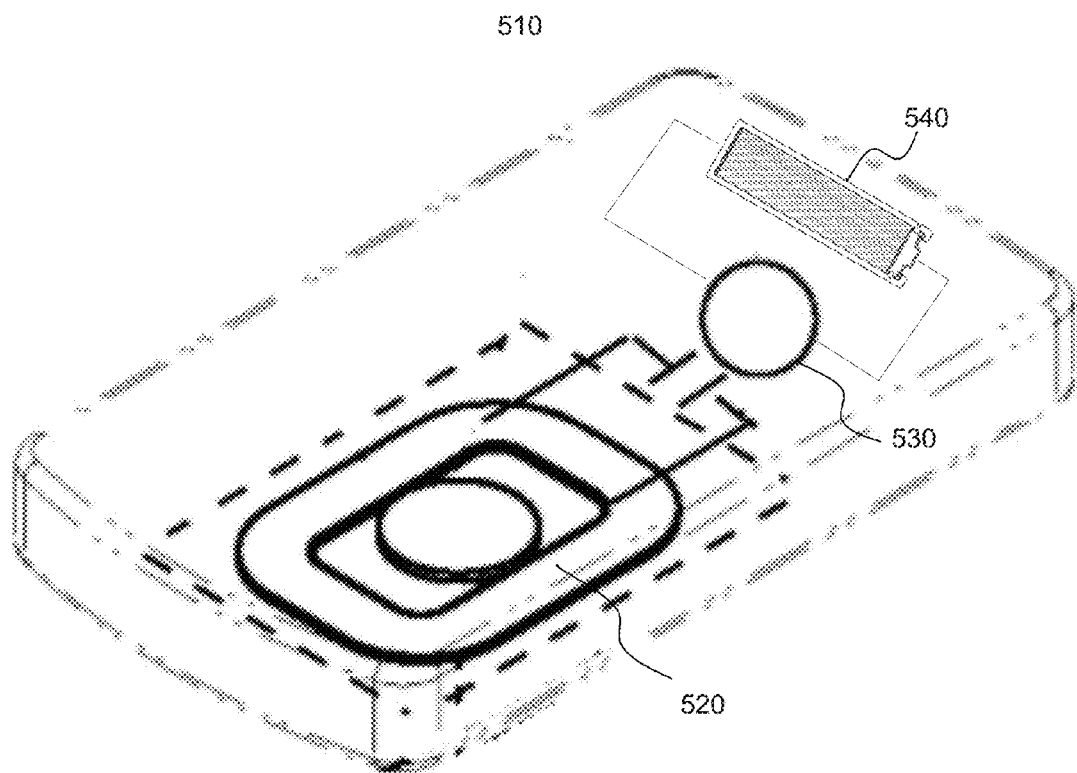
FIG. 5b depicts a wireless transfer station in accordance with an example.

FIG. 5*b* illustrates one exemplary embodiment of the wireless transfer station 510. In one embodiment, the wireless transfer station 510 can be a stand-alone device used to transfer wireless energy to other devices. In another embodiment, the wireless transfer station 510 can include a wireless transfer coil 520 and a power management module 530. In another embodiment, the wireless transfer station 510 can direct energy received at the wireless transfer coil 520 using the power management module 530 to a device coupled to the wireless transfer station 510.

In another embodiment, the wireless transfer station 510 can transfer the energy received at the wireless transfer coil 520 to the coupled device using physical electrical contacts. In another embodiment, the wireless transfer station 510 can transfer the energy to the coupled device using the wireless transfer coil 520. In one embodiment, the wireless transfer station 510 can store received energy at a battery 540.

Figure 5C:
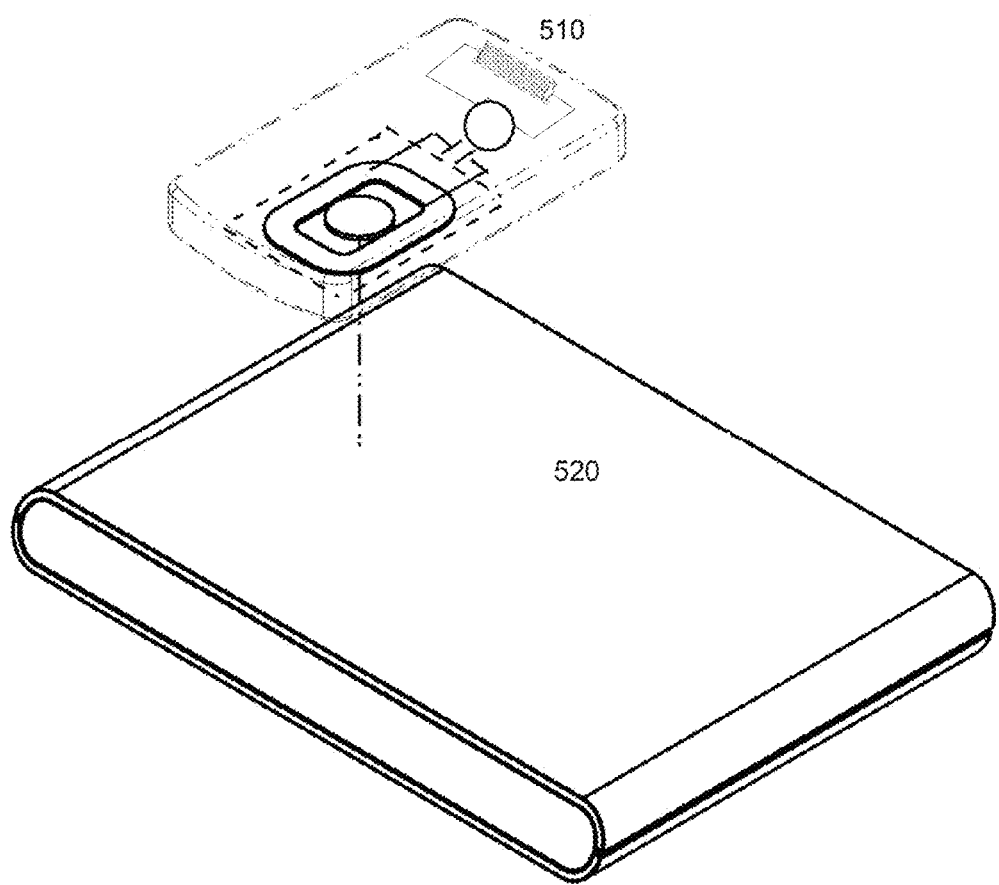
FIG. 5c depicts a wireless transfer station integrated into an object in accordance with an example.
Figure 5D:
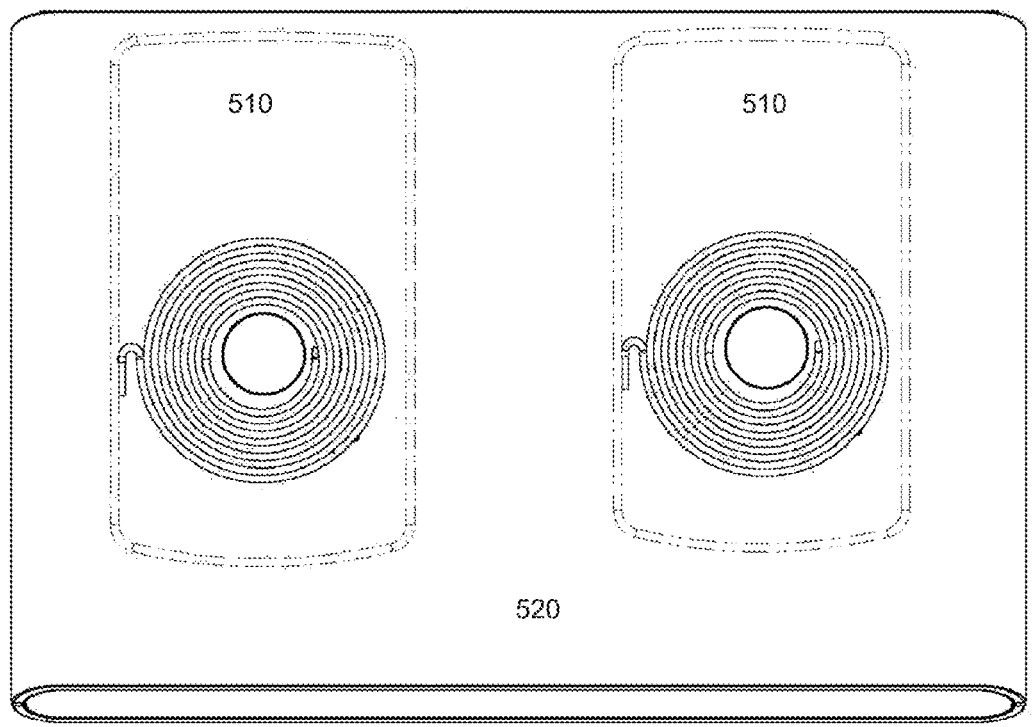
FIG. 5d depicts a plurality of wireless transfer stations integrated into an object in accordance with an example.

FIG. 5c illustrates one exemplary embodiment of the wireless transfer station 510 integrated into an object 520. In one embodiment, the object 520 that the wireless transfer station 510 can be integrated into can be an electronic device, such as a medical device or a wireless energy battery pack. In one example, the wireless transfer station 510 can be integrated into a medical infusion pump and provide energy to the medical infusion pump. In another embodiment, the object 520 can be integrated into a medical cart (such as a work surface of the medical cart), a floor mat, a floor surface, a plate mounted to a wall, a wall surface, chair railing, a room railing, a ceiling tile, a ceiling surface, and so forth. FIG. 5d illustrates that a plurality of wireless transfer stations 510 can be integrated into an object 520. FIG. 5d is the same as FIG. 5c in all other aspects.

Figure 6:
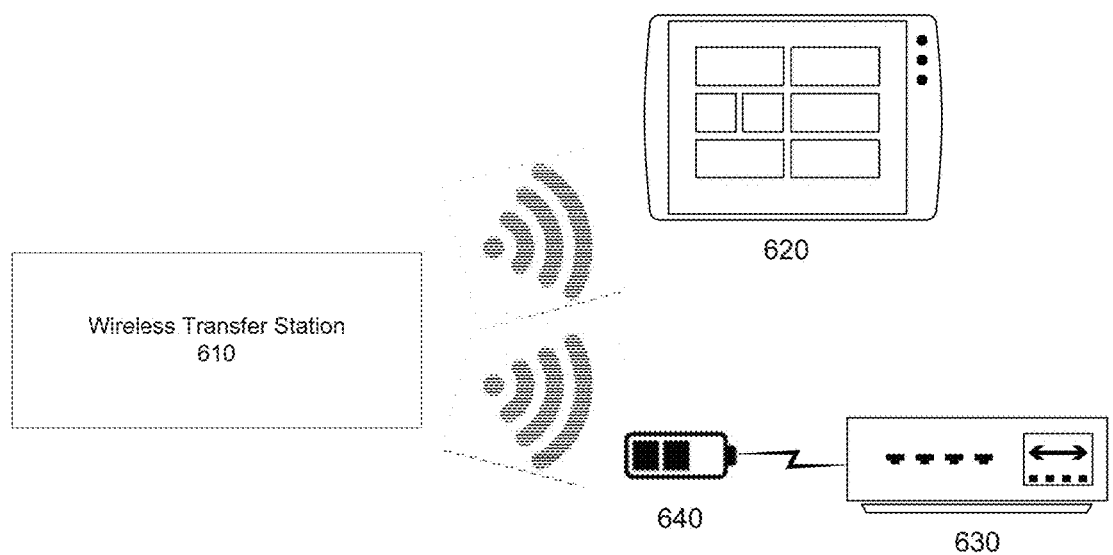
FIG. 6 depicts a wireless transfer station that can provide energy to one or more non-wire powered electronic devices and/or one or more recharge batteries coupled to a device in accordance with an example.

FIG. 6 shows a wireless transfer station 610 that can provide energy to one or more non-wire powered electronic devices 620 and/or one or more rechargeable batteries 640 coupled to a device 630. In another embodiment, the wireless transfer station 610 can provide energy to different types of non-wire powered electronic devices, such as a monitoring device, a computing device, a medical device, and so forth. In one example, the wireless transfer station 610 can provide a unified energy source for the devices 620 and 630 and/or the one or more rechargeable batteries 640 coupled to the device 630. In one embodiment, a unified energy source can be a power source that can provide power to a device, a wireless transfer station, and/or a battery without using different power connectors to provide the power to the device, the wireless transfer station, and/or the battery. In one embodiment, the wireless transfer stations can include an integrated wireless energy coil and a physical electrical energy connection terminal. In another embodiment, the wireless transfer station 610 can transfer energy via an electrical energy connection terminal and/or an integrated wireless transfer coil.

Figure 7A:
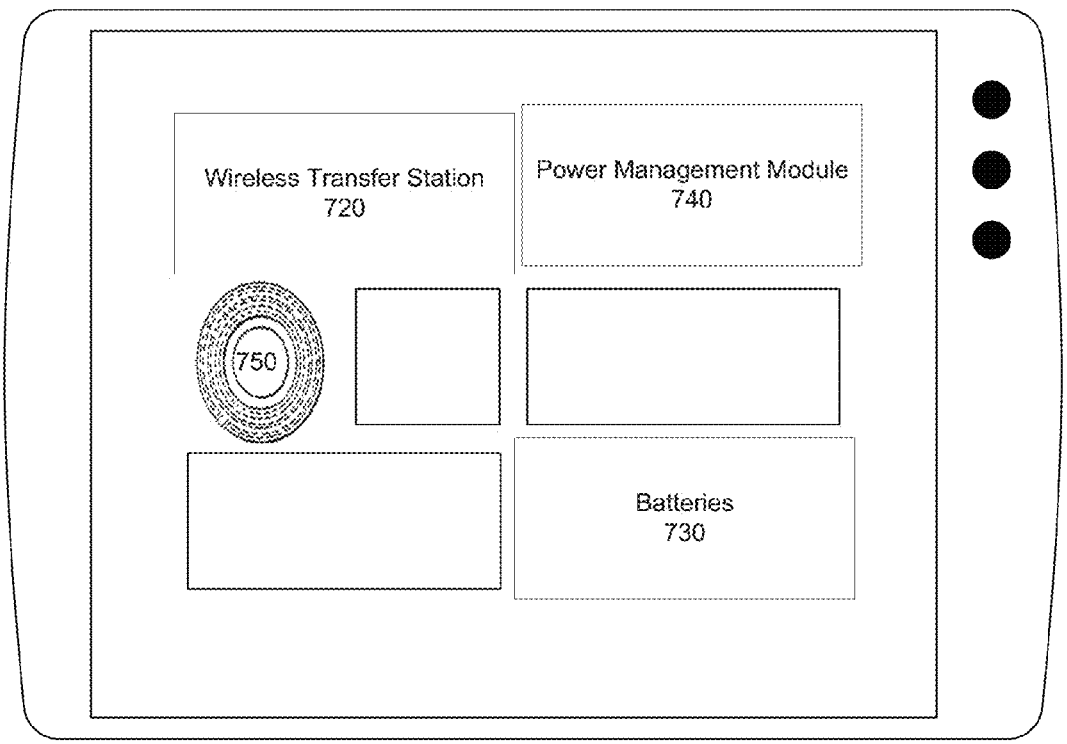
FIG. 7a depicts a device with a wireless transfer station coupled to a device or integrated into the device in accordance with an example.

FIG. 7a shows a device 710 with a wireless transfer station 720 coupled to the device 710 or integrated into the device 710. In one embodiment, the wireless transfer station 720 can be configured to provide energy to batteries 730 of the device 710 and the batteries 730 can provide energy to the device 710. In another embodiment, the wireless transfer station 720 can be configured to provide energy directly to the device 710, e.g. without using batteries. In one example, a power management module 740 can provide energy directly to the device 710 by receiving energy at a wireless transfer coil 750 of the wireless transfer station 710 from a wireless transfer coil of another wireless transfer station and direct the energy via the power management module 740 to the device 710 and/or the batteries 730.

Figure 7B:
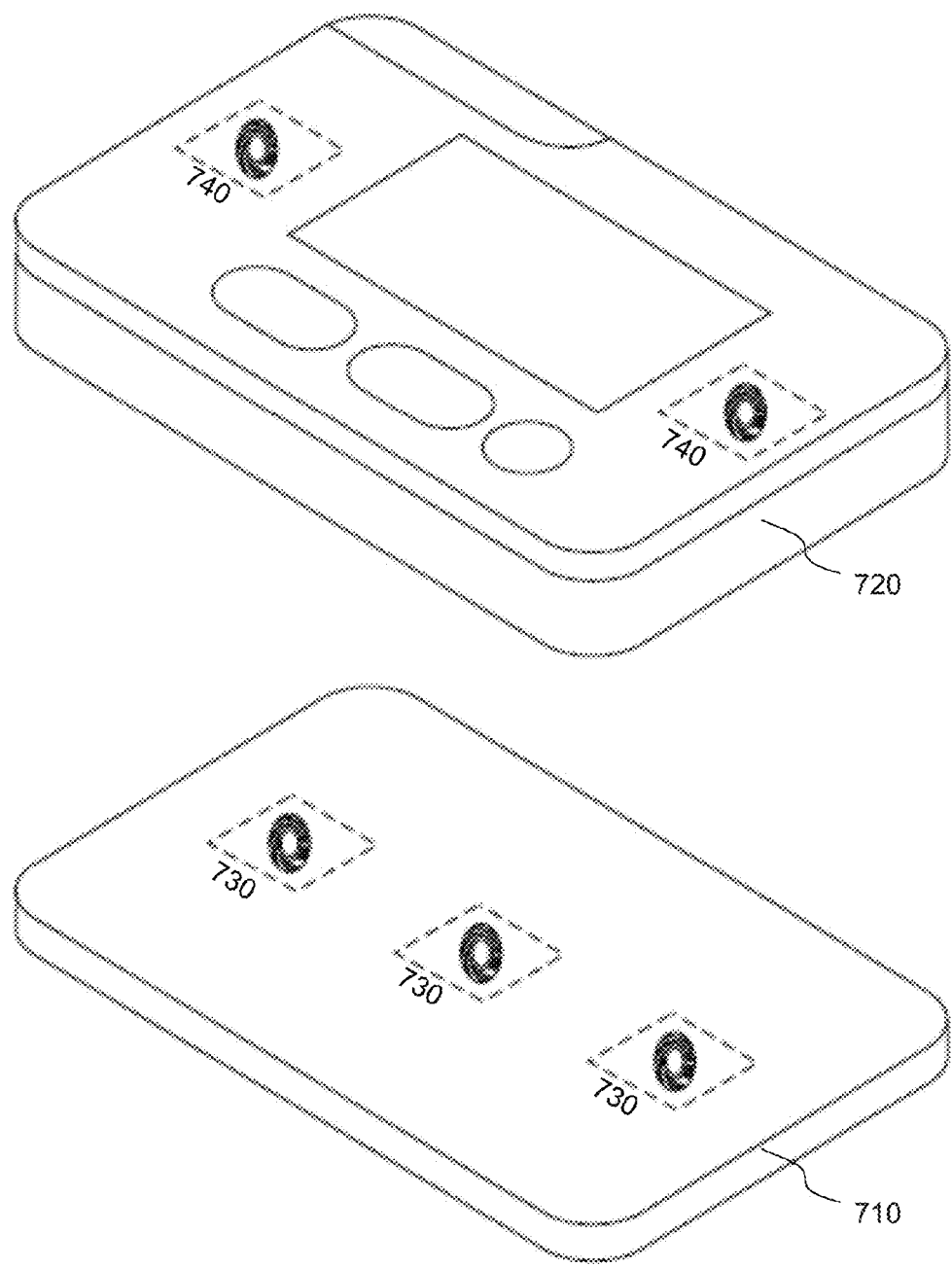
FIG. 7b depicts a wireless transfer station with a plurality of wireless transfer coils configured to transfer energy and/or data to an electronic device in accordance with an example.

FIG. 7b illustrates a wireless transfer station 710 with a plurality of wireless transfer coils 730 configured to transfer energy and/or data to an electronic device 720, such as a medical device. The medical device can include one or more integrated wireless transfer stations 740. In one embodiment, the electronic device 720 can be located adjacent to the wireless transfer station 710. For example, a bottom surface of the electronic device 720 can abut a top surface of the wireless transfer station 710.

In one embodiment, the wireless transfer station or one or more components of the wireless transfer station can be incorporated into a device. The device can be: a wheeled medical cart; a platform coupled the wheeled medical cart; a platform integrated into the wheeled medical cart; and/or a device coupled the wheeled medical cart.

FIGS. 8a, 8b, and 8c show a wheeled medical cart 810 with different configurations of integrated wireless transfer stations 820, 830, and 840, respectively. FIG. 8a shows a wheeled medical cart 810 with a plurality of wireless transfer stations 820 integrated into a selected area 852 of a work surface 850 of the wheeled medical cart 810. FIG. 8b shows a wheeled medical cart 810 with a plurality of wireless transfer stations 830 integrated into a work surface 860 of the wheeled medical cart 810. The wheeled medical cart 810 of FIG. 8b is the same as the wheeled medical cart 810 in FIG. 8a in all other regards. FIG. 8c shows a wheeled medical cart 810 with one or more of wireless transfer stations 840 integrated into a device holder 870 of the wheeled medical cart 810. The wheeled medical cart 810 of FIG. 8c is the same as the wheeled medical carts 810 in FIGS. 8a and 8b in all other regards.

In one embodiment, the wheeled medical cart 810 can have one or more attached work surfaces 850 or 860. In one example, the one or more work surfaces 850 or 860 and/or device holder 870 of the wheeled medical cart can include one or more integrated or coupled wireless transfer coils, such as one or more transmitting coils, one or more repeater coils, and/or one or more receiving coils. In another embodiment, the one or more work surfaces 850 or 860 and/or device holder 870 can have one or more selected areas for other devices, such as medical devices and/or mobile devices, to be placed on the one or more work surfaces 850 or 860 and/or device holder 870 and receive wireless energy.

In one embodiment, the device holder 870 can be designed to hold one or more devices at selected alignments to orient the one or more devices to receive energy from one or more of wireless transfer stations 840. In one example, the device holder 870 can be integrated into the wheeled medical cart 810 and the device holder 870 can hold and orient one or more medical devices to receive wireless energy using wireless transfer stations coupled to the medical devices and/or wireless transfer stations integrated into the medical devices.

In one embodiment, the wheeled medical cart 810 can include one or more electrical systems and/or one or more devices coupled to the wheeled medical cart 810. In another embodiment, the wheeled medical cart 810 can use one or more wireless transfer stations 880 to power the one or more electrical systems and/or the one or more devices. In another embodiment, the one or more wireless transfer stations 880 can receive wireless energy while attached to the wheeled medical cart. In another embodiment, the one or more wireless transfer stations 880 can be removed from the wheeled medical cart and can be attached to another wireless transfer station or be located adjacent to the wireless transfer station and receive wireless energy.

Figure 9:
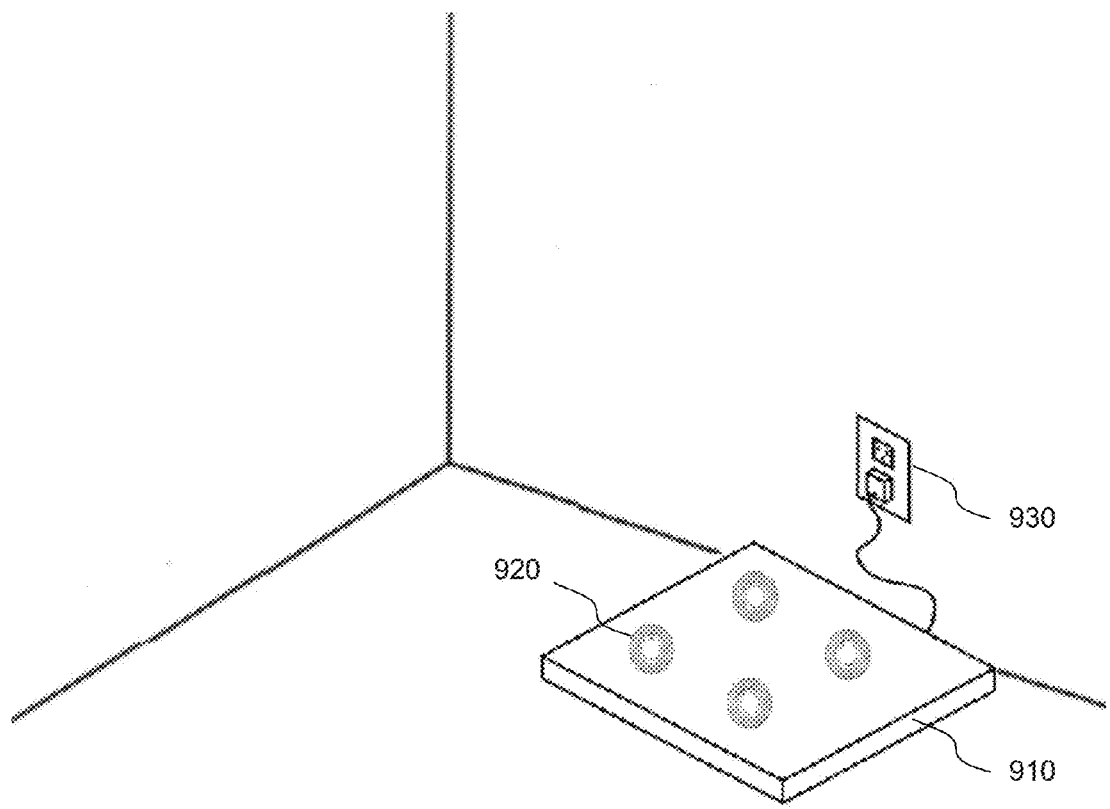
FIG. 9 depicts a floor mat with one or more integrated wireless transfer stations in accordance with an example.

FIG. 9 shows one exemplary embodiment of floor mat 910 with one or more integrated wireless transfer stations 920. In one embodiment, the integrated wireless transfer stations 920 can receive energy and/or data from an outlet 930. In one embodiment, the outlet 930 can be a wall outlet and the integrated wireless transfer stations 920 can receive alternating current (AC) from the outlet 930. In another embodiment, the outlet 930 can be a data outlet, such as an Ethernet outlet, and the integrated wireless transfer stations 920 can receive data from the outlet 930.

In another embodiment, the one or more integrated wireless transfer stations 920 can include one or more wireless transfer coils to transfer energy from the wireless transfer station 920 to another wireless transfer station. In one example, a wireless transfer station coupled to a wheeled medical cart can be moved into a location in proximity or adjacent to the wireless transfer station integrated 920 into the floor mat 910 and receive energy from the one or more wireless transfer stations 920 integrated into the floor mat 910.

Figure 10:
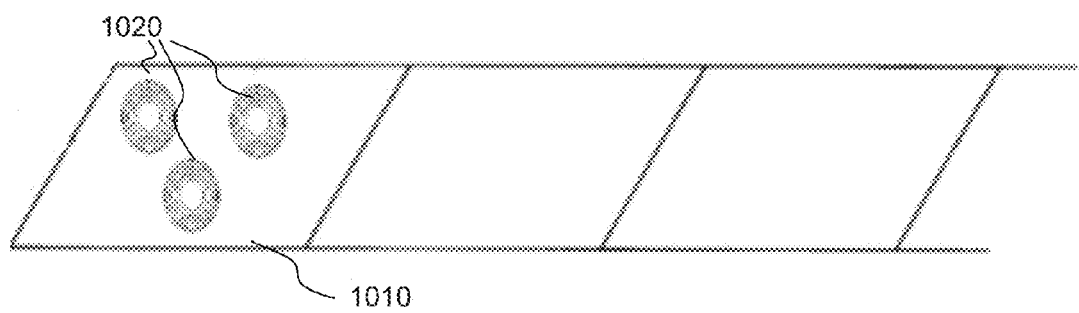
FIG. 10 depicts a flooring surface with one or more integrated wireless transfer stations in accordance with an example.

FIG. 10 shows one exemplary embodiment of a flooring surface 1010 with one or more integrated wireless transfer stations 1020. In another embodiment, the one or more integrated wireless transfer stations 1020 can include one or more wireless transfer coils. In another embodiment, the flooring surface 1010 can be a flooring tile with the one or more integrated wireless transfer stations 1020 integrated into the flooring tile. In another embodiment, the one or more integrated wireless transfer stations 1020 can be coupled to the flooring surface, such as attached to an outer surface of a flooring tile.

Figure 11:
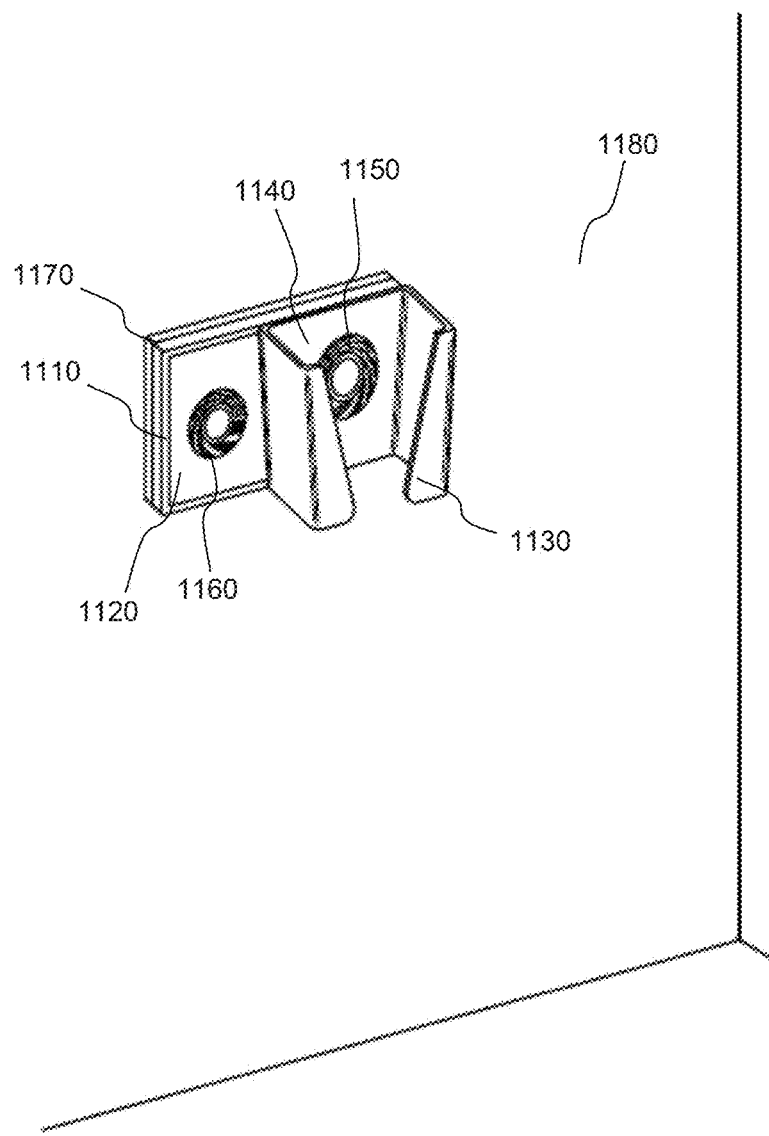
FIG. 11 depicts a plate mounted to a wall with one or more integrated wireless transfer stations in accordance with an example.

FIG. 11 shows one exemplary embodiment of a plate 1110 mounted to a wall 1180 with one or more integrated wireless transfer stations 1120. In another embodiment, the one or more integrated wireless transfer stations 1120 can include one or more wireless transfer coils 1160. In another embodiment, the plate 1110 can be integrated into the wall 1180. In another embodiment, the one or more integrated wireless transfer stations 1120 can be coupled to the wall 1180, such as attached to an inner surface of the wall 1180. In another embodiment, a receptacle 1130 can be attached to the plate 1110. In another embodiment, the receptacle 1130 can receive a device, such as a medical device, or another wireless transfer station. In another embodiment, one or more wireless transfer stations 1140 can be coupled to the receptacle 1130 and the one or more wireless transfer stations 1140 can be used to transfer energy and/or data with the device or the other wireless transfer station, such as by using a wireless transfer coil 1150.

In another embodiment, a plate 1110 can be attached to a mounting plate 1170 that is attached to the wall 1180. One advantage of attaching the plate 1110 to the mounting plate 1190 can be that the plate 1110 can be easily and/or quickly removed from the mounting plate 1170 for maintenance, upgrades, replacement, and so forth. In one embodiment, the plate 1110 can be attached to the mounting plate 1170 using one or more fasteners or connectors, such as hooks, quick connectors, screws, bolts, and so forth.

In one embodiment, the wireless transfer station can regulate an amount of energy received by one or more other wireless transfer stations. In one example, when a first wireless transfer station uses a wireless transfer coil to transfer energy, the first wireless transfer station can control the amount of energy received at a second wireless transfer station by detuning a frequency of the wireless transfer coil of the first wireless transfer station by a selected amount. In another example, the first wireless transfer station can control the amount of energy received from the second wireless transfer station by detuning a frequency of the wireless transfer coil of the first wireless transfer station by selected amount.

Figure 12:
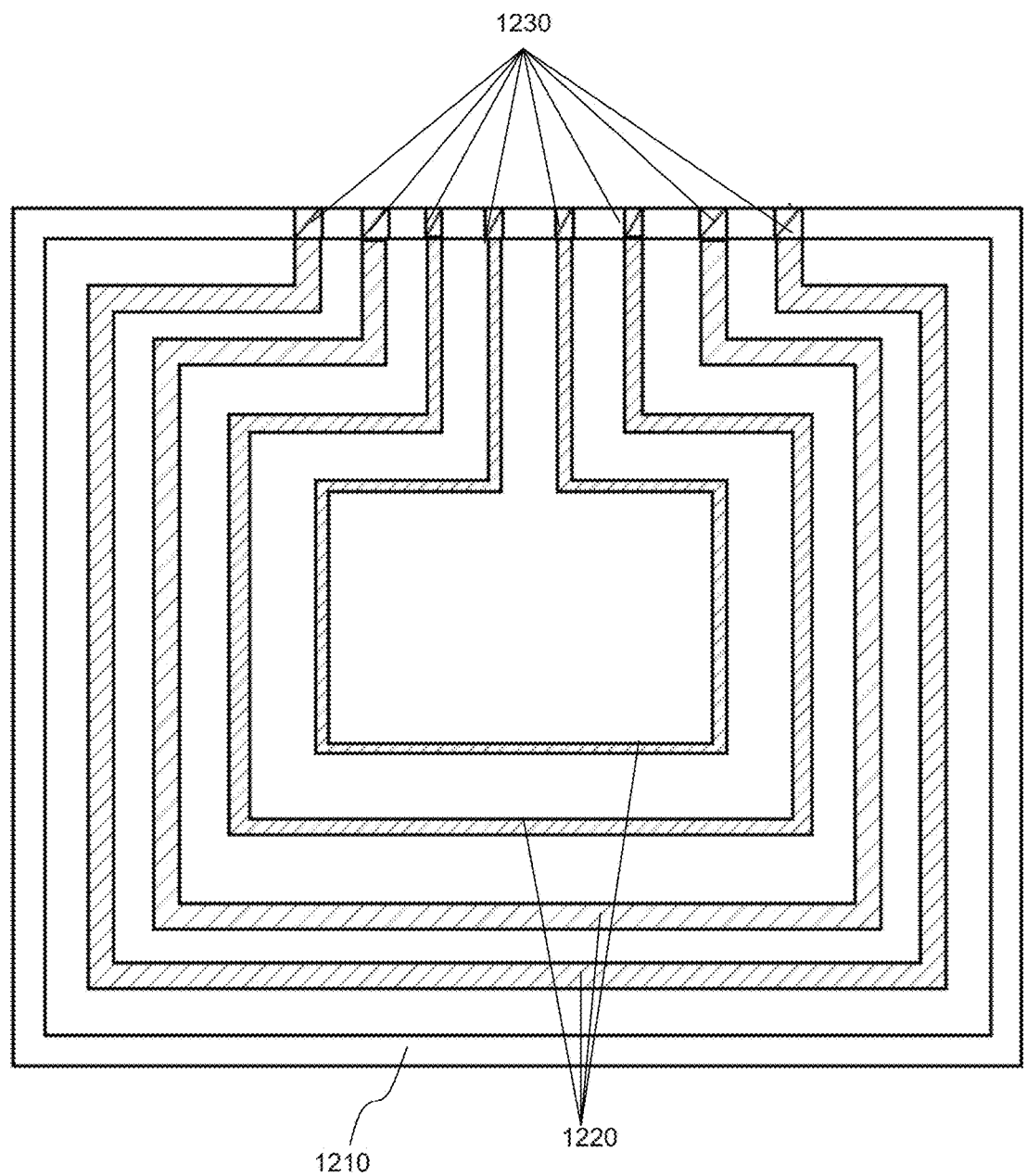
FIG. 12 depicts a wireless transfer coil with a plurality of loops or winds in accordance with an example.

FIG. 12 shows a wireless transfer coil 1210 with a plurality of loops or winds 1220. In one embodiment, an amount of energy transmitted and/or received by the wireless transfer coil 1210 can be adjusted using one or more adjustment modules 1230. In one embodiment, the one or more adjustment modules 1230 can engage or disengage one or more of the plurality of loops 1220 to: effectively vary a size of the wireless transfer coil 1210; change a number of active loops of the wireless transfer coil 1210; change a shape of a magnetic field of the wireless transfer coil 1210; change an amount of energy transferred using the wireless transfer coil 1210; or enable or disable selected devices from receiving energy and/or data from the wireless transfer coil 1210.

In one embodiment, the one or more adjustment modules 1230 can be one or more switches, such as an impedance matching switch or an on/off switch. In one example, a selected number of the plurality of loops 1220 can be engaged by turning on one or more of the corresponding switches and a selected number of the plurality of loops 1220 can be disengaged by turning off one or more of the corresponding switches.

In one embodiment, a resonant frequency between of the wireless transfer coil 1210 can be dynamically adjusted using the one or more adjustment modules 1230. In one embodiment, the one or more adjustment modules 1230 can be adjustable energy oscillators. In another embodiment, the one or more adjustment modules 1230 can be variable capacitors, variable inductors, and/or variable inductors and the respective capacitance, resistance, and/or inductance can be changed to tune or detune the wireless transfer coil 1210.

In one embodiment, a wireless transfer coil of a first wireless transfer station can have a fixed impedance and/or resonant frequency and an impedance and/or resonant frequency of a second wireless transfer coil of a second wireless transfer station can be adjustable. In another embodiment, the impedance and/or resonant frequency of the wireless transfer coil of the first wireless transfer station and the impedance and/or resonant frequency of the wireless transfer coil of the second wireless transfer station can each be adjustable.

In one embodiment, each wireless transfer station can have a unique station ID associated with the wireless transfer station. In another embodiment, each station ID can be used to associate selected information with each wireless transfer station. In another embodiment, each wireless transfer station and/or each type of wireless transfer station can be configured to have a plurality of different characteristics, such as different form factors, different voltage inputs and/or outputs, different current inputs and/or outputs, and so forth.

In one embodiment, each rechargeable battery or battery cell in a wireless transfer station can have a different battery ID. In another embodiment, one or more types of rechargeable batteries or battery cells in a wireless transfer station can each have different battery IDs. In another embodiment, a wireless transfer station can be coupled to a plurality of different types of devices and/or other wireless transfer stations. In one example, the different types of devices and/or other wireless transfer stations can include: devices and/or other wireless transfer stations used for selected applications, devices and/or other wireless transfer stations with different voltage inputs or outputs, devices and/or other wireless transfer stations with different current inputs or outputs, and so forth. In another embodiment, the different types of devices can use different types of wireless transfer stations. In another embodiment, different station IDs for different wireless transfer stations can be associated with selected types of devices. In one example, each device and/or wireless transfer station can determine when a wireless transfer station coupled to the device is a wireless transfer station that is compatible with the device using the station ID of the wireless transfer station and/or the device ID of the device. In one embodiment, a device ID, a station ID, and/or a battery ID can include: serial number information of the device, the station, or the battery; a manufacturing date of the device, the station, or the battery; a manufacturing location of the device, the station, or the battery; and/or a version number of the device, battery, or wireless transfer station, respectively.

Traditionally, energy sources such as battery packs have different energy connectors for coupling the battery packs to different devices. Additionally, traditional battery packs have different energy connectors for different energy transfer levels. In one example, a battery coupled to a wheeled medical cart has one energy connector for transferring energy to the wheeled medical cart and a battery coupled to a medical fusion pump has a different energy connector for transferring energy to the medical fusion pump. Additionally, traditional battery packs for each type of device have different energy transfer levels corresponding to the device receiving the energy and require different battery pack configurations for each type of device. In one example, a wheeled medical cart may use a battery configured to transfer 20 volts and 5 amps of energy while a medical fusion pump may use a battery configured to transfer 10 volts and 3 amps. In one embodiment, a wireless transfer station can select the amount of energy, such as a voltage level or a current level, to wirelessly transfer to a device or other wireless transfer station based on a power configuration, such as a voltage or a current input requirement, of the device or other wireless transfer station. In one embodiment, the wireless transfer station can adjust or change an amount of energy transferred from the wireless transfer station to the device or other wireless transfer station by selecting different sizes of coils and/or tuning or detuning of coils (as discussed in the preceding paragraphs). In one example, the wireless transfer station can select a wireless transfer coil size or frequency to transfer 5 volts of energy to a 5-volt device and select a different wireless transfer coil size or frequency to transfer 10 volts of energy to a 10-volt device.

In one embodiment, the wireless transfer station can communicate with a device or another wireless transfer station and receive an energy requirement information of the device or the other wireless transfer station. The wireless energy battery pack can use the energy requirement information to determine the amount of energy to transfer to the device or the other wireless transfer station. In another embodiment, the wireless transfer station can receive a device ID or a station ID from the device or the other wireless transfer station, respectively, receiving energy from the wireless transfer station. The device ID or station ID can be associated with an energy requirement of the device or the other wireless transfer station and the wireless transfer station can adjust an energy level transfer based on the associated energy requirement.

One advantage of the wireless transfer station selecting the amount of energy to wirelessly transfer to a device or other wireless transfer station is that the wireless transfer station can be used with a plurality of different devices and/or other wireless transfer stations with different energy requirements. Another advantage of wireless transfer station having an adjustable energy level transfer capability can be to enable the wireless transfer station to be used with different devices and/or other wireless transfer stations with different energy level requirements without needing different energy connection adapters. In one example, the wireless transfer station can be connected to the wheeled medical cart, determine that the wheeled medical cart requires 20 volts and 5 amps of energy, and transfer the required energy. The wireless transfer station can later be swapped to a medical fusion pump, the wireless transfer station can determine the medical fusion pump requires 10 volts and 3 amps, and transfer the required energy.

Figure 13A:
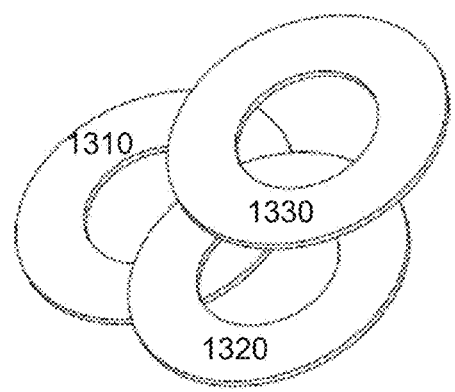
FIG. 13a depicts a wireless transfer coil with overlapping wireless transfer coils in accordance with an example.
Figure 13B:
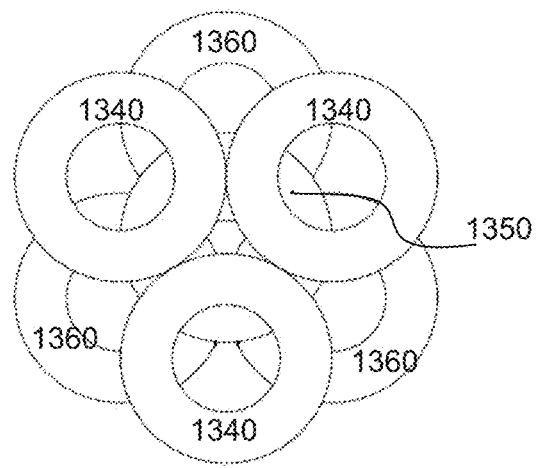
FIG. 13b depicts a layers of wireless transfer coils in accordance with an example.
Figure 13C:
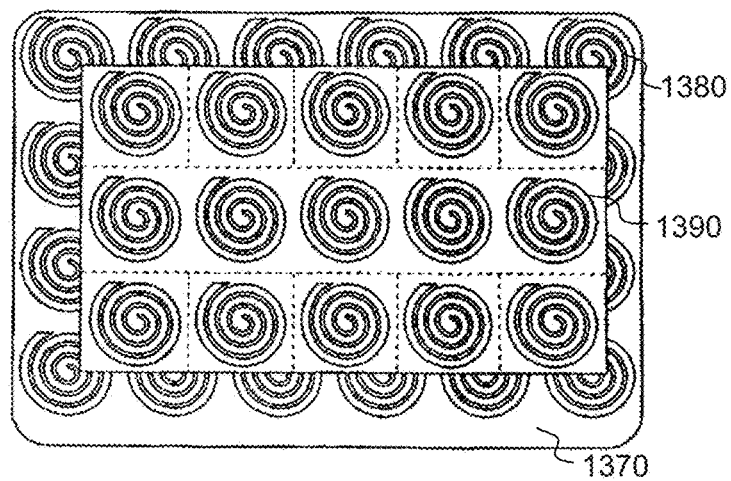
FIG. 13c depicts a wireless transfer station with overlapping wireless transfer coil arrays in accordance with an example.

FIGS. 13a, 13b, and 13c provide examples of wireless transfer coils in overlapping patterns. FIG. 13a shows a wireless transfer coil 1330 with overlapping wireless transfer coils 1310 and 1320. FIG. 13a further shows wireless transfer coil 1320 overlapping wireless transfer coil 1310. FIG. 13b shows layers of wireless transfer coils 1340, 1350, and 1360. FIG. 13b further shows one exemplary embodiment of layers of wireless transfer coils with a bottom layer of wireless transfer coils 1360, a middle layer of wireless transfer coils 1350, and a top layer of wireless transfer coils 1340. FIG. 13c shows a show a wireless transfer station 1370 with overlapping wireless transfer coil arrays 1380 and 1390, as further discussed in the proceeding paragraphs. One advantage of overlapping the wireless transfer coils can be to shape an overall magnetic field from a plurality of wireless transfer coils.

Figure 14:
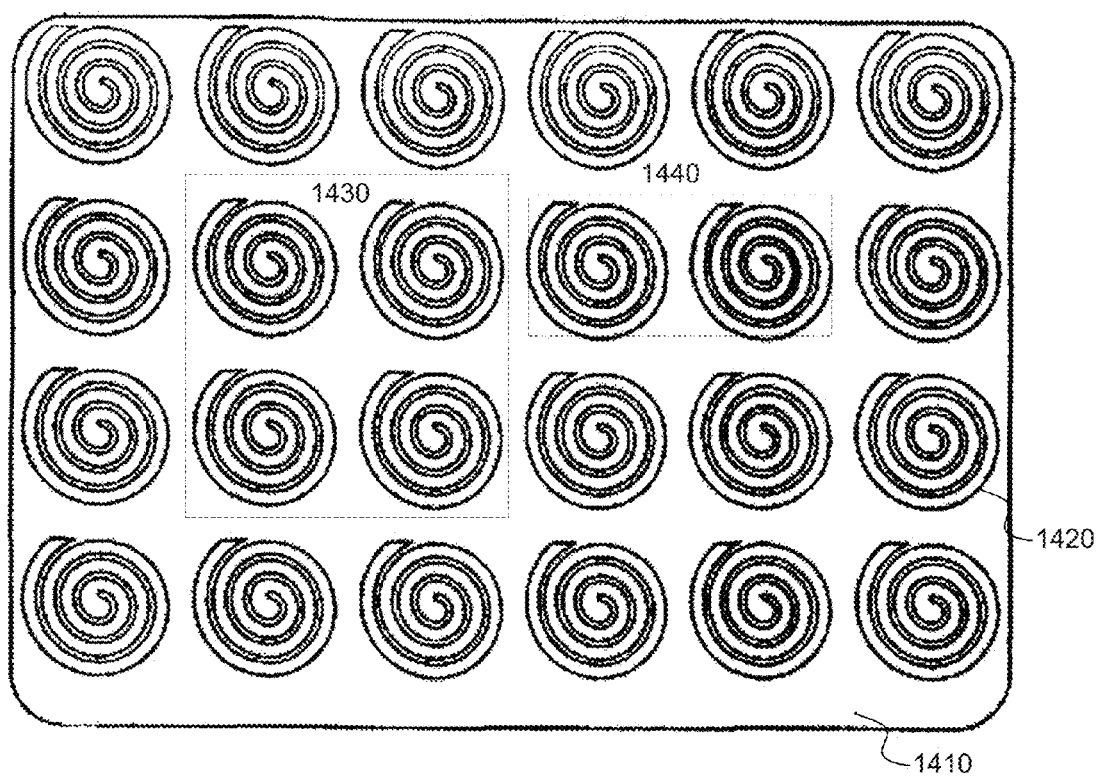
FIG. 14 depicts a wireless transfer station with an array of wireless transfer coils in accordance with an example.

In one embodiment, to increase a coupling distance range between a transmitting coil and a receiving coil and/or to increase a range of alignment positions between a transmitting coil and a receiving coil, a transmitting coil array and/or a receiving coil array can be used. FIG. 14 show a wireless transfer station 1410 with an array of wireless transfer coils 1420. In one embodiment, the wireless transfer coils of the array 1420 can be arranged in a selected pattern, i.e. a coil array pattern. In one example, the wireless transfer coils of the array 1420 can be arranged in a rectangular pattern (such as in FIG. 14), a circular pattern, an elliptical pattern, and so forth. FIG. 14 shows a wireless transfer station 1410 with a non-overlapping wireless transfer coil array pattern. In one embodiment, the wireless transfer coil array can include an array of transmitting coils, receiving coils, repeater coils, or a combination thereof. One advantage of non-overlapping wireless energy coils can be to create separate electromagnetic fields.

In one embodiment, the wireless transfer station can select a number of wireless transfer coils in the coil array, e.g. a wireless transfer coil array subset, to provide energy for wireless energy transfer. FIG. 14 further shows the wireless transfer station 1410 with wireless transfer coil subsets 1430 and 1440 within the wireless coil array 1420. In one embodiment, the wireless transfer station 1410 can select a number of wireless transfer coils, e.g. a wireless transfer coil subset. In one example, the wireless transfer station 1410 can receive or transmit energy using one or more wireless transfer coil subsets 1430 and 1440 within the wireless coil array 1420 and not receive or transmit energy using the other wireless transfer coils in the wireless coil array 1420. FIG. 14 shows a wireless transfer coil subset 1430 with four selected wireless transfer coils in the wireless transfer coil subset 1430 and wireless transfer coil subset 1440 with two selected wireless transfer coils in the wireless transfer coil subset 1440. Subsets 1430 and 1440 are exemplary embodiments of different numbers of selected wireless transfer coils in a wireless transfer coil subsets. The number of selected wireless transfer coils in a wireless transfer coil subset is not limited to the number of coils in subsets 1430 and 1440 of FIG. 14.

In another embodiment, the wireless transfer station 1410 can detect a location of one or more receiving coils relative to one or more transmitting coils in the wireless coil array 1420. When the location of the one or more receiving coils is determined relative to the one or more transmitting coils, the wireless coil array 1420 array provide can energy to the one or more wireless transfer coils or a wireless transfer coil array subset, such as wireless transfer coil subset 1430 or 1440, corresponding to the location of the one or more receiving coils. One advantage of providing power to the one or more the one or more wireless transfer coils or the wireless transfer coil array subset corresponding to the location of the one or more receiving coils can be to increase or optimize an amount of energy received at the one or more receiving coils.

In one embodiment, to detect the location of the one or more receiving coils of a device or another wireless transfer station relative to one or more transmitting coils of the wireless transfer station 1410, the wireless transfer station 1410 can be in communication with the device or the other wireless transfer station. In one example, the other wireless transfer station can send a beacon to the wireless transfer station 1410 indicating a location of the other wireless transfer station or one or more receiving coil of the other wireless transfer station relative to the one or more wireless transfer coils or the wireless transfer coil array subset. In another embodiment, the wireless transfer station 1410 can determine alignment information based on the beacon and indicate to a user alignment directions.

In one embodiment, to determine a number of transmitting coils in the array subset 1430 or 1440 to provide energy to, the wireless transfer station 1410 can serially or sequentially applying energy to one or more wireless transfer coils in the wireless coil array 1420. Another wireless transfer station with one or more receiving coils can communicate energy information to the wireless transfer station 1410 when different transmitting coils are active and transferring energy. The wireless transfer station 1410 can use the energy information to determine an optimal number and/or subset of the transmitting coils to provide energy to for optimal or increased energy transfer to the receiving coil of the other wireless transfer station.

In another embodiment, the wireless coil array 1420 can be an array of receiving coils. The wireless coil array 1420 can sequentially or serially connect a selected subset of receiving coils to a receiving energy source and determine an arrangement of a selected subset of receiving coils, such as subsets 1430 or 1440, to receive an increased or optimal amount of energy from one or more transmitting coils. In one embodiment, an energy management system can determine an optimal number of selected transmitting coils or selected receiving coils to activate for coupling or pairing to provide a device or a wireless transfer station with a selected level of energy.

In one embodiment, a wireless transfer station can use a location of a transmitting coil and/or the location of a receiving coil to determine alignment information, such as the alignment of a receiving coil relative to a transmitting coil. In one example, the wireless transfer station can use the alignment information to determine a direction to move a transmitting coil and/or a receiving coil to increase or optimize the energy received at the receiving coil from the transmitting coil. In one example, when a receiving coil of a device is located left of center of a transmitting coil of a wireless transfer station, the wireless transfer station or the device can determine that to increase the energy transfer to the receiving coil, the receiving coil can be moved to the right and/or the transmitting coil can be moved to the left.

In one embodiment, the wireless transfer station can indicate to a user of a device and/or another wireless transfer station with the a wireless transfer coil the direction to move the wireless transfer coil to increase an alignment and/or energy transfer between a wireless transfer coil of the wireless transfer station and the wireless transfer coil of the device or the other wireless transfer station. In one embodiment, the wireless transfer station can determine the direction to move a wireless transfer coil by monitoring an energy level received at the wireless transfer coil of the wireless transfer station. In one example, if a receiving coil of a wireless transfer station is moved to the left and an energy received from a transmitting coil of another wireless transfer station decreases, the wireless transfer station can determine that the receiving coil can be moved to the right relative to the transmitting coil of the other wireless transfer station to increase the received energy.

In one embodiment, the wireless transfer station can determine a direction for a wireless transfer coil to move by monitoring an energy load on one or more wireless transfer coils, such as transmitting coils, of the wireless transfer station. In one example, when a transmitting coil is moved to the left and an energy load on the transmitting coil decreases, the wireless transfer station can determine that the transmitting coil can be moved to the right to increase the energy received at a receiving coil of another wireless transfer station. In another embodiment, a device and/or the other wireless transfer station can communicate energy information to the wireless transfer station. The wireless transfer station can use the energy information to determine the location of a wireless transfer coil of the wireless transfer station relative to a wireless transfer coil of the other wireless transfer station and provide alignment information to the user.

In one embodiment, a wireless transfer station can include a display or other sensory indicator for providing alignment directions to a user via a graphical user interface. In another example, the wireless transfer station can communicate the alignment directions to another device with a display or other sensory indicator for providing the alignment directions to the user.

Figure 15:
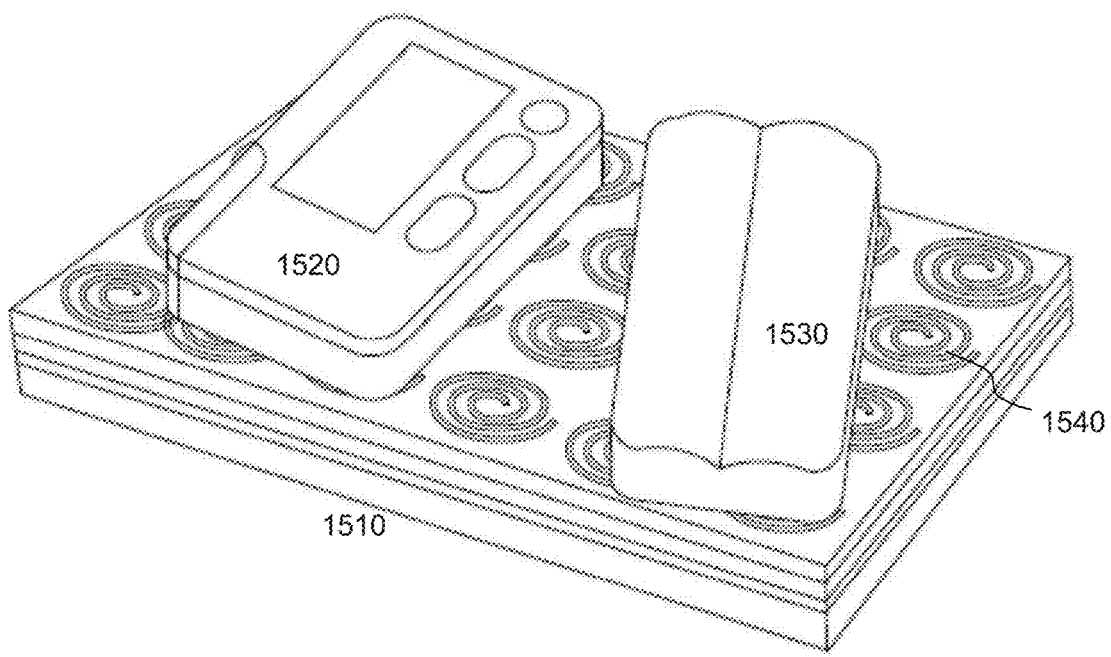
FIG. 15 depicts a wireless transfer hub transferring energy and/or information with an electronic device and/or another wireless transfer station using wireless transfer coils in accordance with an example.

In one embodiment, a wireless transfer station can be a wireless transfer hub (e.g. energy and/or data transfer) for a plurality of selected devices and/or other wireless transfer stations. FIG. 15 illustrates a wireless transfer hub 1510 transferring energy and/or information with an electronic device 1520, such as a medical device, and/or another wireless transfer station 1530 using wireless transfer coils 1540. In one embodiment, the electronic device 1520 and the other wireless transfer station 1530 can exchange energy and/or information with the wireless transfer station 1510 at the same time or at different times. In another embodiment, the electronic device 1520 and the other wireless transfer station 1530 can transfer energy and/or information with the wireless transfer hub 1510 using different wireless transfer coils 1540.

In one example, the wireless transfer hub 1510 coupled to a medical cart can wirelessly provide selected levels of energy to systems and subsystems of the medical cart and/or other devices coupled to the medical cart. In one embodiment, the wireless transfer hub 1510 coupled to the medical cart can receive energy and/or data from a wireless transfer station and relay the energy and/or data to systems and subsystems of the medical cart and/or other devices using one or more repeater coils.

In one embodiment, a medical cart or a device can have an integrated wireless transfer station to provide energy to systems and/or subsystems of the medical cart or the device when one or more external wireless transfer stations (e.g. non-integrated wireless transfer stations) are being recharged. In one embodiment, the integrated wireless transfer station can include one or more wireless transfer coils to receive energy and/or data from another wireless transfer station. In one example, the medical cart or the device can receive energy from the one or more external wireless transfer stations until an energy level of the one or more external wireless transfer stations is depleted or decreases below a threshold energy level. In this example, when the energy level of the one or more external wireless transfer stations is depleted or decreases below a threshold energy level, the medical cart or the device can be positioned adjacent a transmitter coil of another wireless transfer station and the one or more external wireless transfer stations can receive energy for recharging. In one embodiment, while the one or more external wireless transfer stations receive energy for recharging, the integrated wireless transfer station can provide energy to the medical cart or the device.

In one embodiment, the integrated wireless transfer station can receive energy from the other wireless transfer station to recharge one or more batteries of the integrated wireless transfer station. In another embodiment, the integrated wireless transfer station can receive energy from the one or more external wireless transfer stations to recharge the one or more batteries of the integrated wireless transfer station. In another embodiment, when the one or more external wireless transfer stations receive energy from another wireless transfer station, the one or more external wireless transfer stations can provide partial or full energy to the medical cart or the device.

In one embodiment, when the energy level of the one or more external wireless transfer stations is depleted or decreases below a threshold energy level, the one or more external wireless transfer stations can be removed from the medical cart or the device and placed adjacent a transmitter coil of another wireless transfer station to receive energy to recharge the external wireless transfer station. In one embodiment, while the one or more external wireless transfer stations are removed for recharging and/or until one or more other external wireless transfer stations are attached to the medical cart or the device, the integrated wireless transfer station can provide energy to one or more system or subsystem of the medical cart or the device. In one embodiment, when the medical cart or the device is placed adjacent to a transmitter coil of a wireless transfer station, the integrated wireless transfer station can receive energy from the wireless transfer station to recharge the integrated wireless transfer station.

In one embodiment, the medical cart or a device can include a wireless transfer coil to transfer energy and/or data with another wireless transfer station. In one example, the medical cart or a device can use the wireless transfer coil to receive energy and provide energy directly to one or more systems and/or subsystems of the medical cart or the device and/or provide energy to an energy source, such as a battery, of the medical cart or the device. In one example, the medical cart or the device with the wireless transfer coil can be placed near a transmitter coil of a wireless transfer station and the wireless transfer coil can relay energy to one or more systems and/or subsystems of the medical cart or the device.

Figure 16:
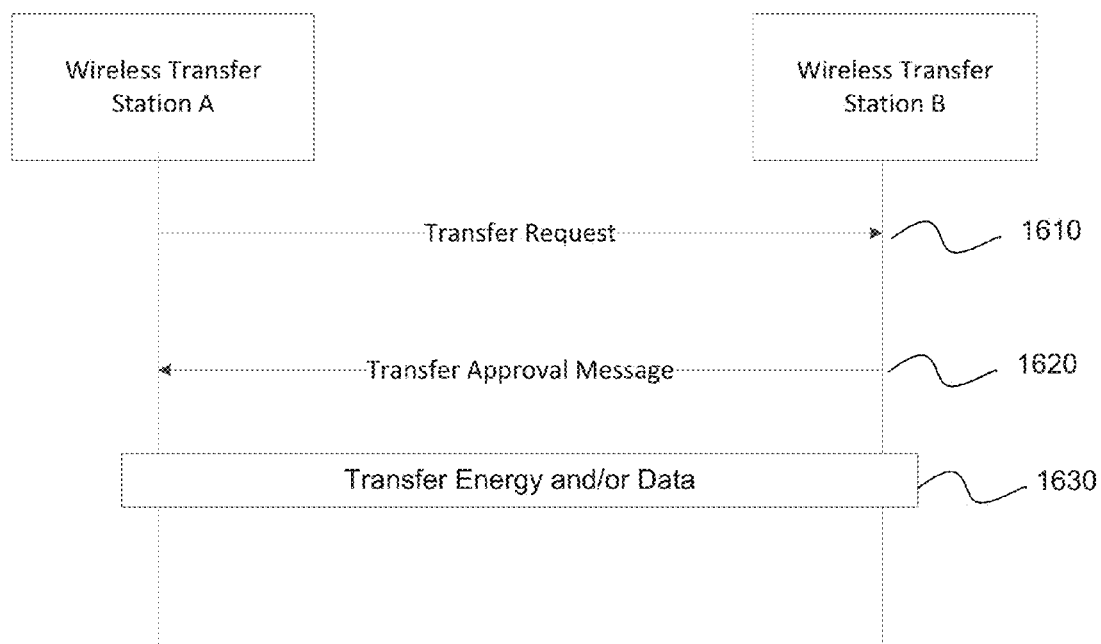
FIG. 16 shows a framework for a wireless transfer station A in communication with wireless transfer station B to determine when to transfer wireless energy and/or data between wireless transfer station A and wireless transfer station B in accordance with an example.

FIG. 16 shows a wireless transfer station A in communication with wireless transfer station B to determine when to transfer wireless energy and/or data between wireless transfer station A and wireless transfer station B. In one embodiment, wireless transfer station A can send a transfer request message to a wireless transfer station B, as in block 1610. In one embodiment, the transfer request message can include a frequency capability of the wireless transfer station A. The transfer request message can also include additional information, such as the voltage and current level at which the energy is desired to be transferred, a charge level of a battery, and an amount of time until a battery is full and the energy is to be turned off. In another embodiment, the wireless transfer station B can send a transfer approval message with a frequency for transferring energy and/or data to the wireless transfer station A, as in block 1620. In the transfer approval message, the wireless transfer station B can send an acknowledgment of the messages received, and actions to be taken, such as changing the frequency, voltage, or current. In another embodiment, the wireless transfer station A and the wireless transfer station B can transfer energy and/or data between wireless transfer station A and wireless transfer station B using the frequency, voltage, current, and time indicated in the transfer approval message, as in block 1630.

Figure 17:
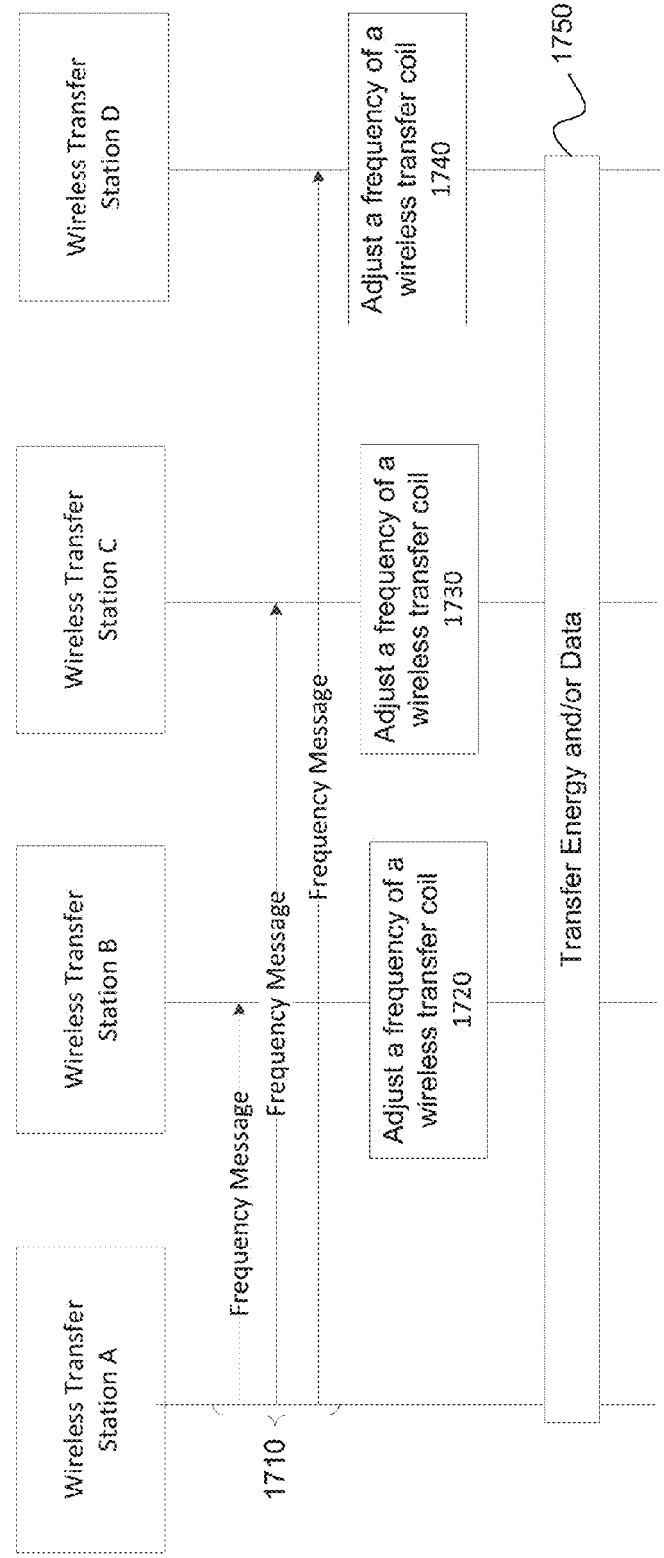
FIG. 17 shows a framework for a wireless transfer station in communication with a plurality of wireless transfer stations to determine when to transfer wireless energy and/or data between the wireless transfer station and one or more of the plurality of wireless transfer stations in accordance with an example.

FIG. 17 shows a wireless transfer station A in communication with a plurality of wireless transfer stations (e.g. wireless transfer station B, wireless transfer station C, and wireless transfer station D) to determine when to transfer wireless energy and/or data between wireless transfer station A and one or more of the plurality of wireless transfer stations. In one embodiment, the wireless transfer station A can broadcast or unicast to the wireless transfer station B, the wireless transfer station C, and/or the wireless transfer station D a frequency message that includes one or more frequencies to the wireless transfer station B, the wireless transfer station C, and/or the wireless transfer station D to use to receive energy and/or data, as in block 1710. In one embodiment, when the wireless transfer station B, the wireless transfer station C, and/or the wireless transfer station D receive the frequency message, each of the wireless transfer stations B, C, and/or D can adjust a frequency of a wireless transfer coil coupled each of the wireless transfer stations B, C, and/or D for transferring energy and/or data, as in blocks 1720, 1730, and 1740. In another embodiment, the wireless transfer stations A, B, C, and/or D can dynamically adjust the frequency for transferring energy and/or data using an active crystal array to produce different frequency signals. In another embodiment, the wireless transfer station A and the wireless transfer station B, the wireless transfer station C, and/or the wireless transfer station D can transfer energy and/or data between the wireless transfer station A and the wireless transfer station B, the wireless transfer station C, and/or the wireless transfer station D using the one or more frequencies in the frequency message, as in block 1750.

Figure 18:
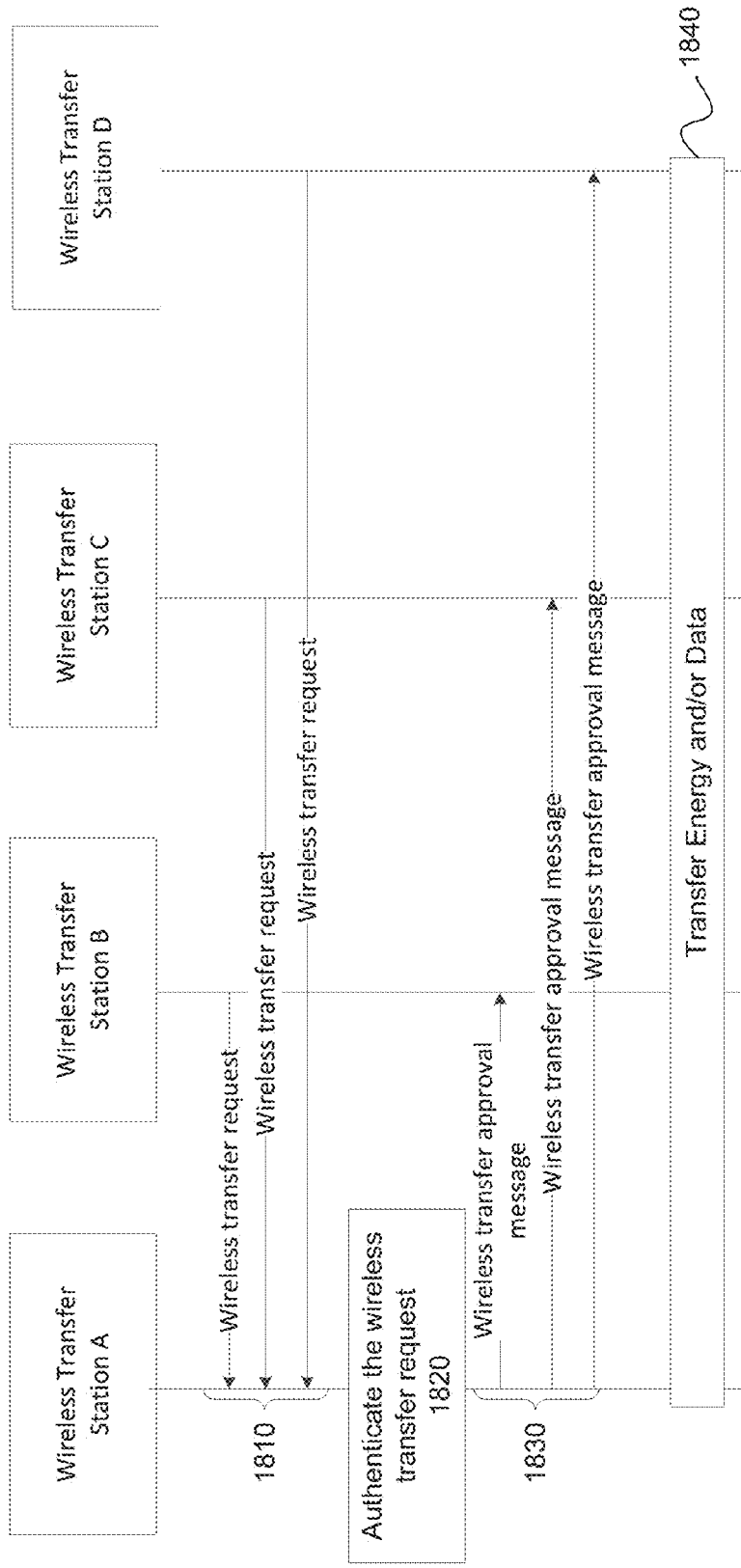
FIG. 18 shows a framework for a wireless transfer station restricting or limiting access of one or more other wireless transfer stations to transfer wireless energy and/or data from the wireless transfer station in accordance with an example.

FIG. 18 illustrates that a wireless transfer station A can restrict or limit access of one or more other wireless transfer stations (such as wireless transfer station B, wireless transfer station C, and wireless transfer station D) to transfer wireless energy and/or data from wireless transfer station A. In one embodiment, the wireless transfer station A can receive a wireless transfer request from the wireless transfer station B, the wireless transfer station C, and/or the wireless transfer station D, as in block 1810. In another embodiment, the wireless transfer station A can authenticate the wireless transfer requests from the wireless transfer station B, the wireless transfer station C, and/or the wireless transfer station D, as in block 1820. In another embodiment, when the wireless transfer request is authenticated, the wireless transfer station A can communicate a wireless transfer approval message to the wireless transfer station B, the wireless transfer station C, and/or the wireless transfer station D, as in block 1830. In one embodiment, the wireless transfer approval message can include a frequency for the wireless transfer station B, the wireless transfer station C, and/or the wireless transfer station D to transfer wireless energy and/or data with the wireless transfer station A. In another embodiment, the wireless transfer station A and the wireless transfer station B, the wireless transfer station C, and/or the wireless transfer station D can transfer energy and/or data between the wireless transfer station A and the wireless transfer station B, the wireless transfer station C, and/or the wireless transfer station D, as in block 1840.

Figure 19:
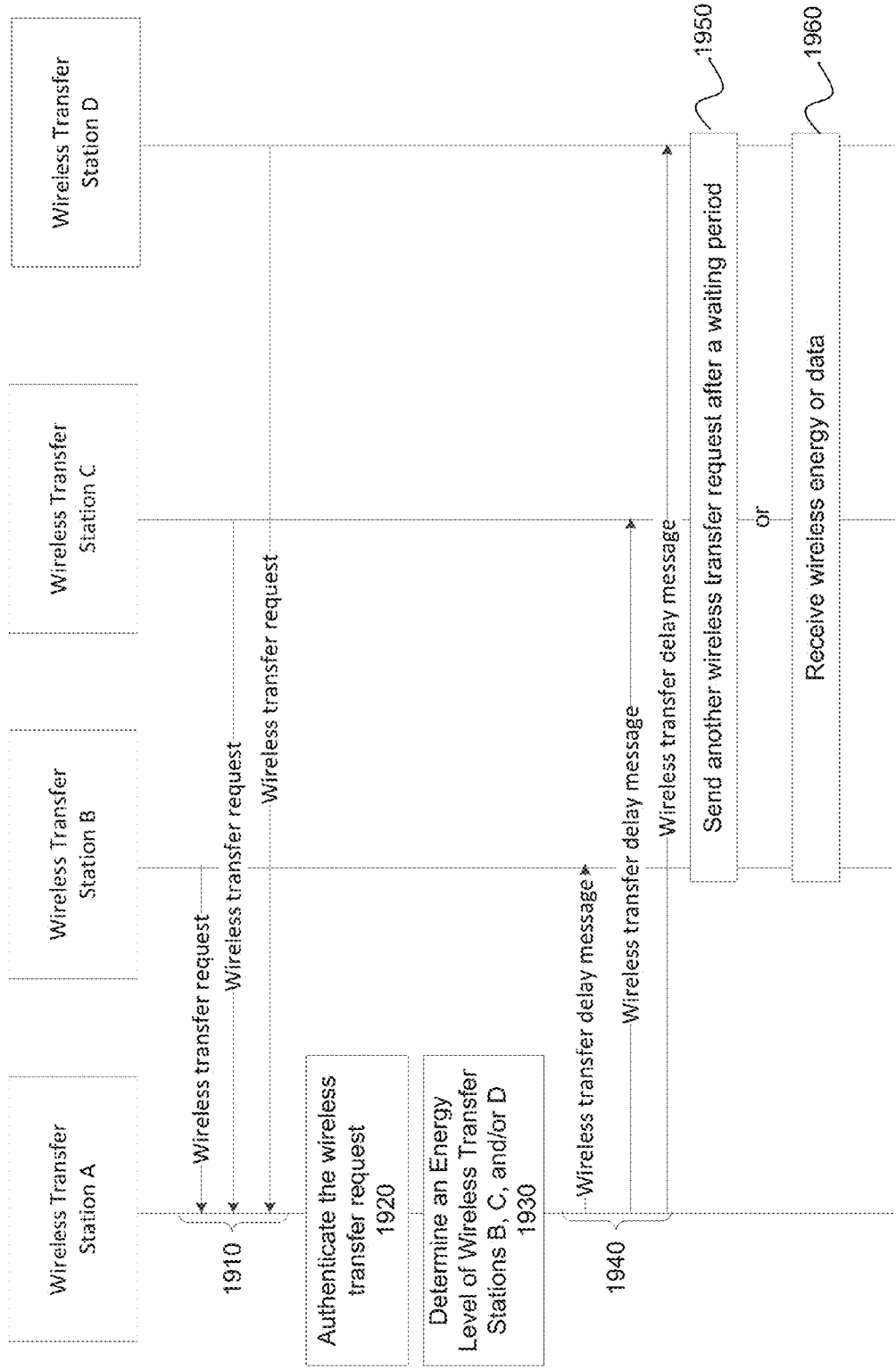
FIG. 19 shows a framework for a wireless transfer station that can delay access of one or more other wireless transfer stations to transfer wireless energy and/or data with the wireless transfer station in accordance with an example.

FIG. 19 illustrates that a wireless transfer station A can delay access of one or more other wireless transfer stations (such as wireless transfer station B, wireless transfer station C, and wireless transfer station D) to transfer wireless energy and/or data with wireless transfer station A. In one embodiment, the wireless transfer station A can receive a wireless transfer request from the wireless transfer station B, the wireless transfer station C, and/or the wireless transfer station D, as in block 1910. In another embodiment, the wireless transfer station A can authenticate the wireless transfer requests from the wireless transfer station B, the wireless transfer station C, and/or the wireless transfer station D, as in block 1920. In another embodiment, when the wireless transfer request is authenticated by wireless transfer station A, the wireless transfer station A can determine an energy level of the wireless transfer station B, the wireless transfer station C, and/or the wireless transfer station D, as in block 1930.

When the energy level of the wireless transfer station B, the wireless transfer station C, and/or the wireless transfer station D is above a selected threshold value and/or the energy level of the device is above a selected threshold value, the wireless transfer station can send the wireless transfer station B, the wireless transfer station C, and/or the wireless transfer station D a wireless transfer delay message, as in block 1940. In another embodiment, the wireless transfer delay message can include a waiting time period for the wireless transfer station B, the wireless transfer station C, and/or the wireless transfer station D to wait before sending a wireless transfer request. In another embodiment, the wireless transfer delay message can include a waiting time period before the wireless transfer station B, the wireless transfer station C, and/or the wireless transfer station D can receive wireless energy and/or data from the wireless transfer station A. In another embodiment, when the wireless transfer station B, the wireless transfer station C, and/or the wireless transfer station D receives the wireless energy transfer delay message, the wireless transfer station B, the wireless transfer station C, and/or the wireless transfer station D can wait for the waiting time period and then send another wireless transfer request (as in block 1950) or receive wireless energy and/or data (as in block 1960).

Figure 20:
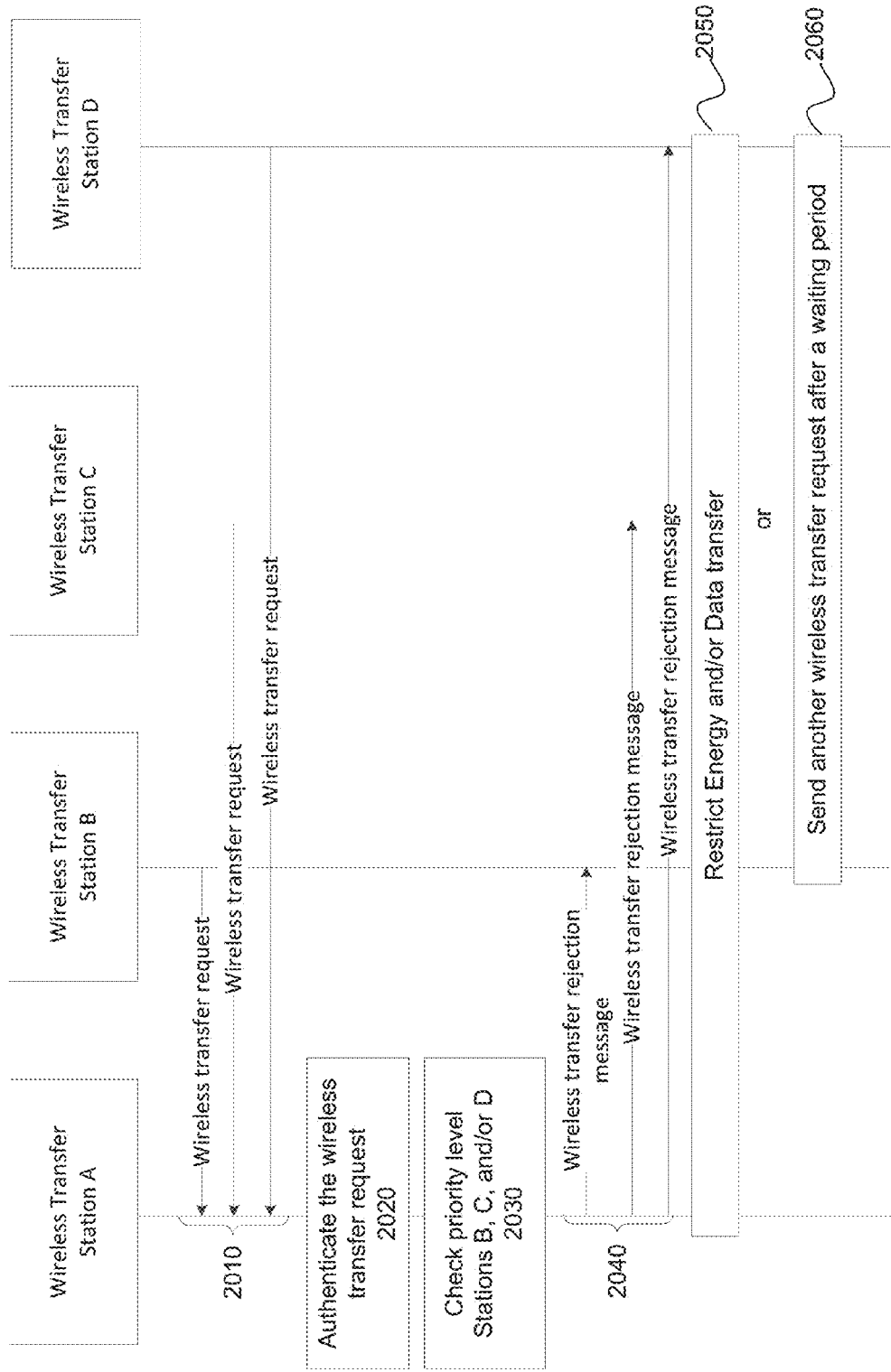
FIG. 20 shows a framework for a wireless transfer station to control access of one or more other wireless transfer stations to transfer wireless energy and/or data with the wireless transfer station based on a priority level of the one or more other wireless transfer stations in accordance with an example.

FIG. 20 illustrates that a wireless transfer station A can control access of one or more other wireless transfer stations (such as wireless transfer station B, wireless transfer station C, and wireless transfer station D) to transfer wireless energy and/or data with wireless transfer station A based on a priority level of the one or more other wireless transfer stations. In one embodiment, the wireless transfer station A can receive a wireless transfer request from the wireless transfer station B, the wireless transfer station C, and/or the wireless transfer station D, as in block 2010. In another embodiment, the wireless transfer station A can authenticate the wireless transfer requests from the wireless transfer station B, the wireless transfer station C, and/or the wireless transfer station D, as in block 2020. In one embodiment, when the wireless transfer request is authenticated, the wireless transfer station A can check a priority level of the wireless transfer station B, the wireless transfer station C, and/or the wireless transfer station D, as in block 2030. When a priority level of the wireless transfer station B, the wireless transfer station C, and/or the wireless transfer station D is below a selected threshold value, the wireless transfer station A can send the wireless transfer station B, the wireless transfer station C, and/or the wireless transfer station D a wireless transfer rejection message, as in block 2040. In another embodiment, when the wireless transfer station A rejects a wireless transfer request, the wireless transfer station B, the wireless transfer station C, and/or the wireless transfer station D can be restricted or prohibited from receiving energy and/or data from wireless transfer station A, as in block 2050. In another embodiment, the wireless transfer rejection message can include a waiting time period for the device to wait before sending another wireless energy transfer request, as in block 2060. In another embodiment, when the wireless transfer request is not authenticated, the wireless transfer station can reject the wireless energy transfer request.

Figure 21:
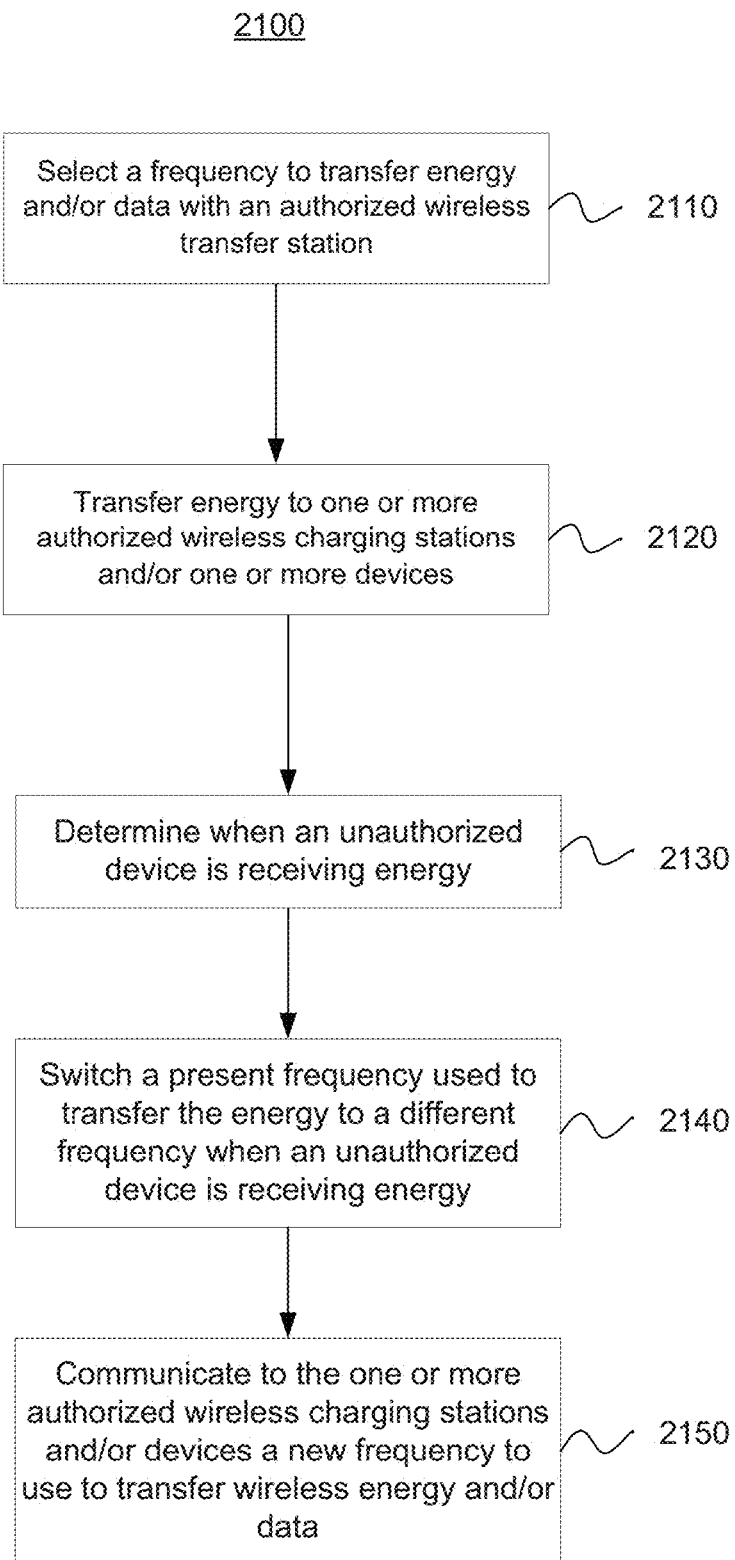
FIG. 21 illustrates a method for determine when an unauthorized device may be receiving energy from a wireless transfer station in accordance with an example.

FIG. 21 uses a flow chart 2100 to illustrate the functionality of one embodiment of the computer circuitry with a wireless transfer station operable to determine when an unauthorized device may be receiving energy from the wireless transfer station. The functionality may be implemented as a method or the functionality may be executed as instructions on a machine, where the instructions are included on at least one computer readable medium or one non-transitory machine readable storage medium. In one embodiment, the computer circuitry can be configured to select a frequency to transfer energy and/or data with one or more authorized wireless transfer station, as in block 2110. In one embodiment, the computer circuitry can be configured to transfer energy to one or more authorized wireless transfer stations and/or one or more devices, as in block 2120. In another embodiment, the computer circuitry can be configured to determine when an unauthorized device may be receiving energy from the wireless transfer station, as in block 2130. In one example, the wireless transfer station determines when an unauthorized device may be receiving energy from the wireless transfer station by comparing an amount energy received by authorized devices with the amount of energy transmitted by the wireless transfer station. In this example, when the difference between the amount of energy received by authorized devices and the amount of energy transmitted by the wireless transfer station exceeds a selected threshold, one or more unauthorized devices may be receiving energy from the wireless transfer station.

In one embodiment, when the wireless transfer station detects one or more unauthorized devices receiving energy from the wireless transfer station, the wireless transfer station can switch a present frequency used to transfer the energy to a different frequency, as in block 2140. In one embodiment, the wireless transfer station and the one or more authorized wireless transfer station can have a predetermined resonant frequency list to determine the next frequency that the wireless transfer station can use to transfer energy and/or data with the one or more authorized wireless transfer stations. In another embodiment, the wireless transfer station can iterate through the predetermined resonant frequency list sequentially to transfer energy and/or data with the one or more authorized wireless transfer stations. In another embodiment, the wireless transfer station can iterate through the predetermined resonant frequency list using a predetermined pattern or algorithm. In another embodiment, when the wireless transfer station switches the frequency, the wireless transfer station can communicate to the one or more authorized wireless transfer stations and/or devices a new frequency to use to transfer wireless energy and/or data, as in block 2150.

In one embodiment, when the wireless transfer station detects one or more unauthorized devices receiving energy from the wireless transfer station, the wireless transfer station can deactivate one or more wireless transfer coils. In one example, when the wireless transfer station detects one or more unauthorized devices receiving energy from the wireless transfer station the wireless transfer station can sequentially deactivate wireless transfer coils to determine which wireless transfer coil the unauthorized device is receiving energy from. In one embodiment, the wireless transfer station, the other wireless transfer stations, and/or the authorized devices can tolerate a wider range of frequency variations for transferring wireless energy.

Figure 22:
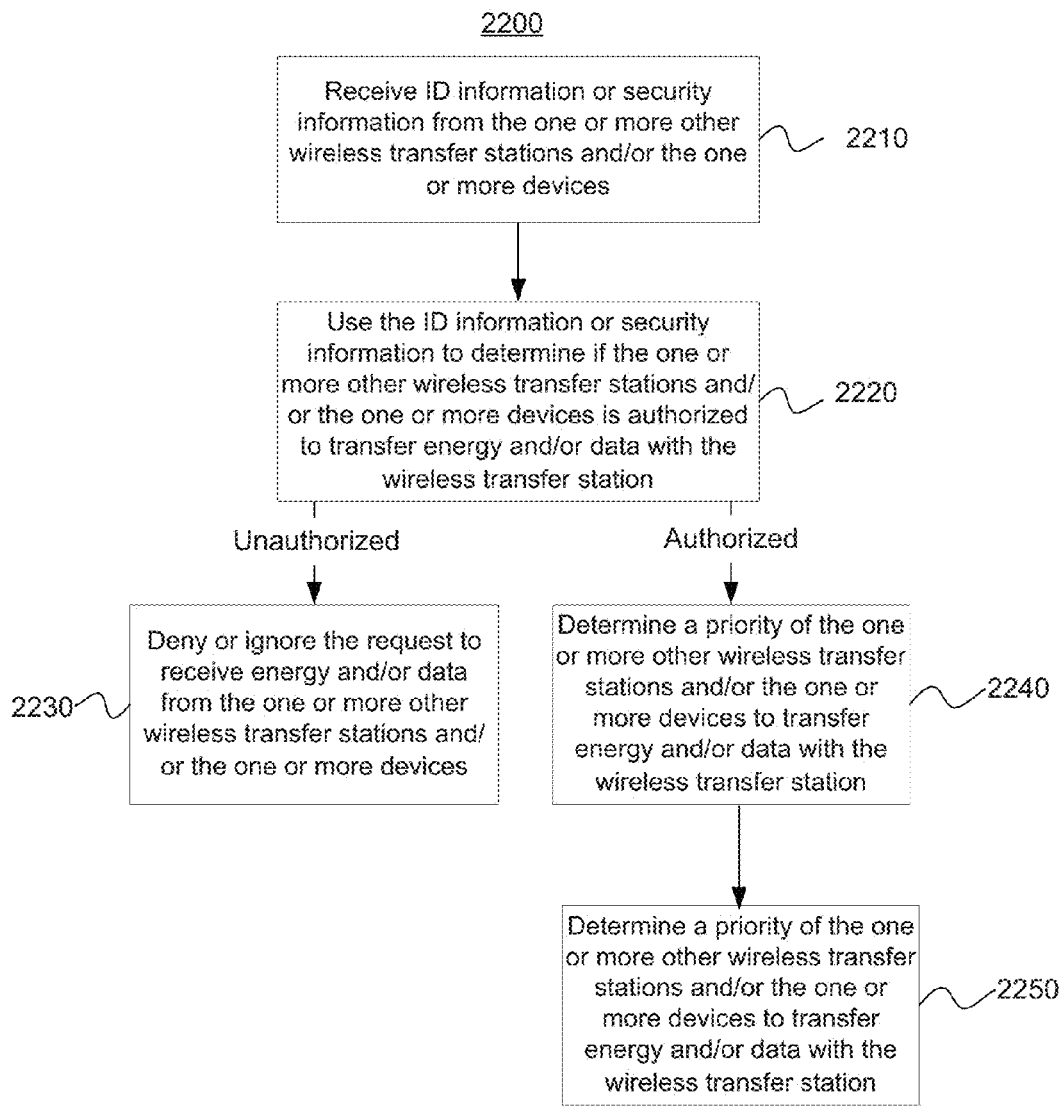
FIG. 22 illustrates a method for determine when one or more other wireless transfer stations and/or one or more devices is authorized to transfer energy and/or data with the wireless transfer station in accordance with an example.

FIG. 22 uses a flow chart 2200 to illustrate the functionality of one embodiment of the computer circuitry with a wireless transfer station operable to determine when one or more other wireless transfer stations and/or one or more devices is authorized to transfer energy and/or data with the wireless transfer station. The functionality may be implemented as a method or the functionality may be executed as instructions on a machine, where the instructions are included on at least one computer readable medium or one non-transitory machine readable storage medium. In one embodiment, the computer circuitry can be configured to receive ID information or security information from the one or more other wireless transfer stations and/or the one or more devices, as in block 2210. In another embodiment, the computer circuitry can be configured to use the ID information or security information to determine if the one or more other wireless transfer stations and/or the one or more devices are authorized to transfer energy and/or data with the wireless transfer station, as in block 2220. In another embodiment, when the one or more other wireless transfer stations and/or the one or more devices are not authorized to receive energy from the wireless transfer station, the computer circuitry can be configured to deny or ignore the request to receive energy and/or data from the one or more other wireless transfer stations and/or the one or more devices, as in block 2230. In another embodiment, when from the one or more other wireless transfer stations and/or the one or more devices are authorized to receive energy from the wireless transfer station, the computer circuitry can be configured to determine a priority of the one or more other wireless transfer stations and/or the one or more devices to transfer energy and/or data with the wireless transfer station, as in block 2240. In another embodiment, the computer circuitry can be configured to transfer energy and/or data with the one or more other wireless transfer stations and/or the one or more devices based on the determined priority, as in block 2250.

In one embodiment, when the one or more other wireless transfer stations and/or the one or more devices are unable to provide security information, the wireless transfer station can deny the request for a transfer of energy and/or data. In another embodiment, when the one or more other wireless transfer stations and/or the one or more devices are unable to provide security information, the wireless transfer station can place the transfer request at the bottom of a transfer queue.

Figure 23:
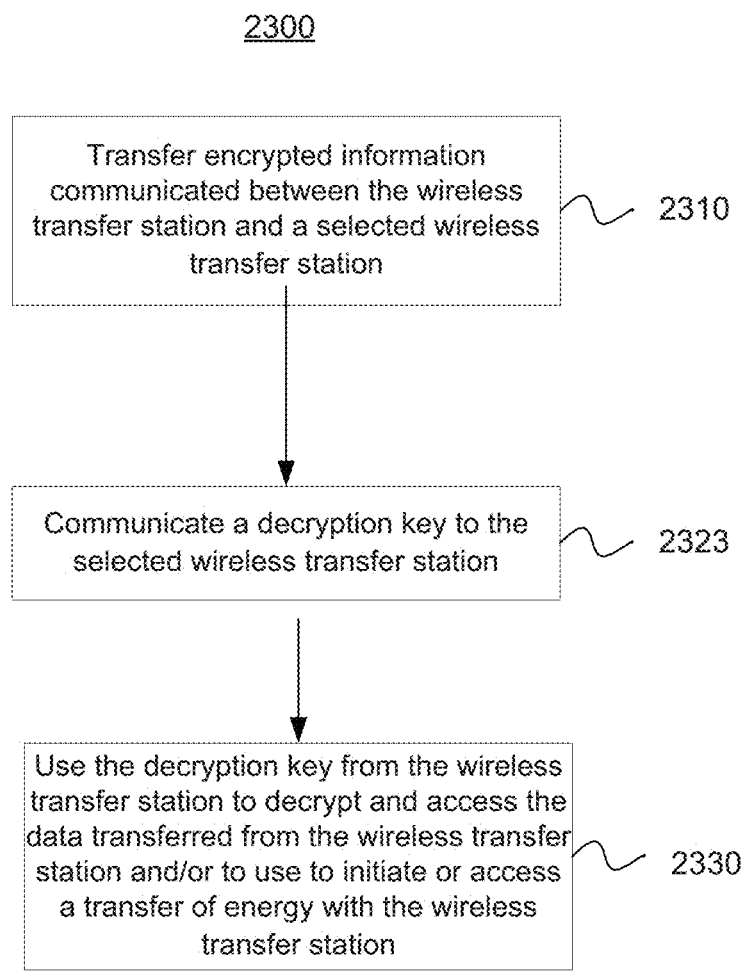
FIG. 23 illustrates a method for communicating data with one or more other wireless transfer stations and/or one or more devices using a communications module in accordance with an example.

FIG. 23 uses a flow chart 2300 to illustrate the functionality of one embodiment of the computer circuitry with a wireless transfer station operable to communicate data with one or more other wireless transfer stations and/or one or more devices using a communications module (as shown in FIG. 4). The functionality may be implemented as a method or the functionality may be executed as instructions on a machine, where the instructions are included on at least one computer readable medium or one non-transitory machine readable storage medium. In one embodiment, the computer circuitry can be configured to transfer encrypted information communicated between the wireless transfer station and a selected wireless transfer station, as in block 2310. In another embodiment, the computer circuitry can be configured to communicate a decryption key to the selected wireless transfer station, as in block 2323. In another embodiment, the selected wireless transfer station can be configured use the decryption key from the wireless transfer station to decrypt and access the data transferred from the wireless transfer station and/or to use to initiate or access a transfer of energy with the wireless transfer station, as in block 2330. In another embodiment, when the selected wireless transfer station is authorized to transfer energy and/or data with the wireless transfer station, the selected wireless transfer station can use a predetermined authentication key. In another embodiment, the selected wireless transfer station can request the wireless transfer station send an authentication key for the selected wireless transfer station to use for authentication.

In one embodiment, the wireless transfer station can determine when an authorized wireless transfer station is in a coverage area of the wireless transfer station before transferring the energy and/or data. In another embodiment, the authorized wireless transfer station transferring energy and/or information with the wireless transfer station can provide a user with an alert to not remove the authorized wireless transfer station from a coverage area of the wireless transfer station until an energy transfer and/or a data transfer is complete between the wireless transfer station and the authorized wireless transfer station. In one embodiment, when the wireless transfer station detects one or more unauthorized wireless transfer stations receiving wireless energy and/or data, the wireless transfer station can alert a third party of the unauthorized wireless transfer stations.

In another embodiment, another wireless transfer station or a device can have an authentication dongle coupled to the other wireless transfer station or the device to transfer wireless energy and/or data from the wireless transfer station. In one embodiment, the authentication dongle can include a wireless transfer coil to transfer energy and/or data with the wireless transfer station. In another embodiment, the wireless transfer station can communicate with the authentication dongle to verify the other wireless transfer station or the device is authorized to transfer energy and/or data with the wireless transfer station.

In one example, when a device requests to receive energy from the wireless transfer station, the wireless transfer station can authenticate the device using a coupled authentication dongle. In this example, when the wireless transfer station authenticates that the device has an authorization dongle coupled to the device, the wireless transfer station can communicate a frequency to the device for the device to use to transfer energy and/or data with the wireless transfer station. In one embodiment, when the wireless transfer station verifies that the other wireless transfer station or the device has an attached authorization dongle, the wireless transfer station can communicate a frequency to the other wireless transfer station or the device via the authentication dongle. In another embodiment, the authentication dongle can receive a key from wireless transfer station to activate a wireless transfer coil attached to the device or integrated into the device.

Figure 24:
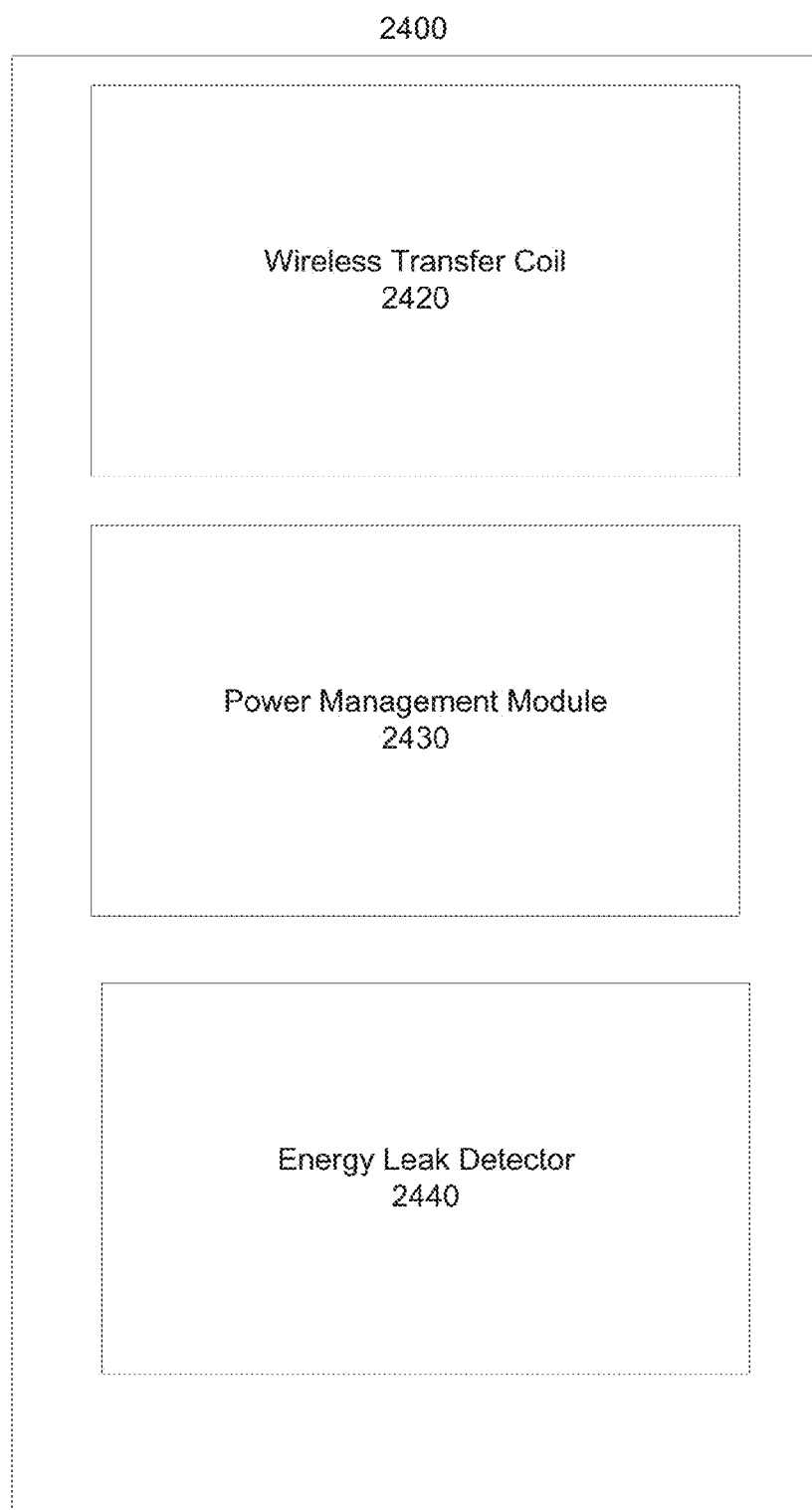
FIG. 24 depicts a wireless transfer station in accordance with an example.

FIG. 24 illustrates a wireless transfer station 2410. FIG. 24 further illustrates that the wireless transfer station 2410 can include a wireless transfer coil 2420, a power management module 2430, and an energy leak detector 2440. In one embodiment, the energy leak detector 2440 can determine when an unauthorized device is absorbing or receiving energy from a coverage area of the wireless transfer station 2410. In another embodiment, the energy leak detector 2440 can detect when foreign materials and/or unauthorized devices are interfering with an energy transfer between the wireless transfer station 2410 and an authorized device or an authorized wireless transfer station. In another embodiment, the energy leak detector can determine if there is an energy leak by comparing the expected energy received by the authorized device and/or the authorized wireless transfer station with the actual amount of energy transmitted by the wireless transfer station 2410.

Figure 25:
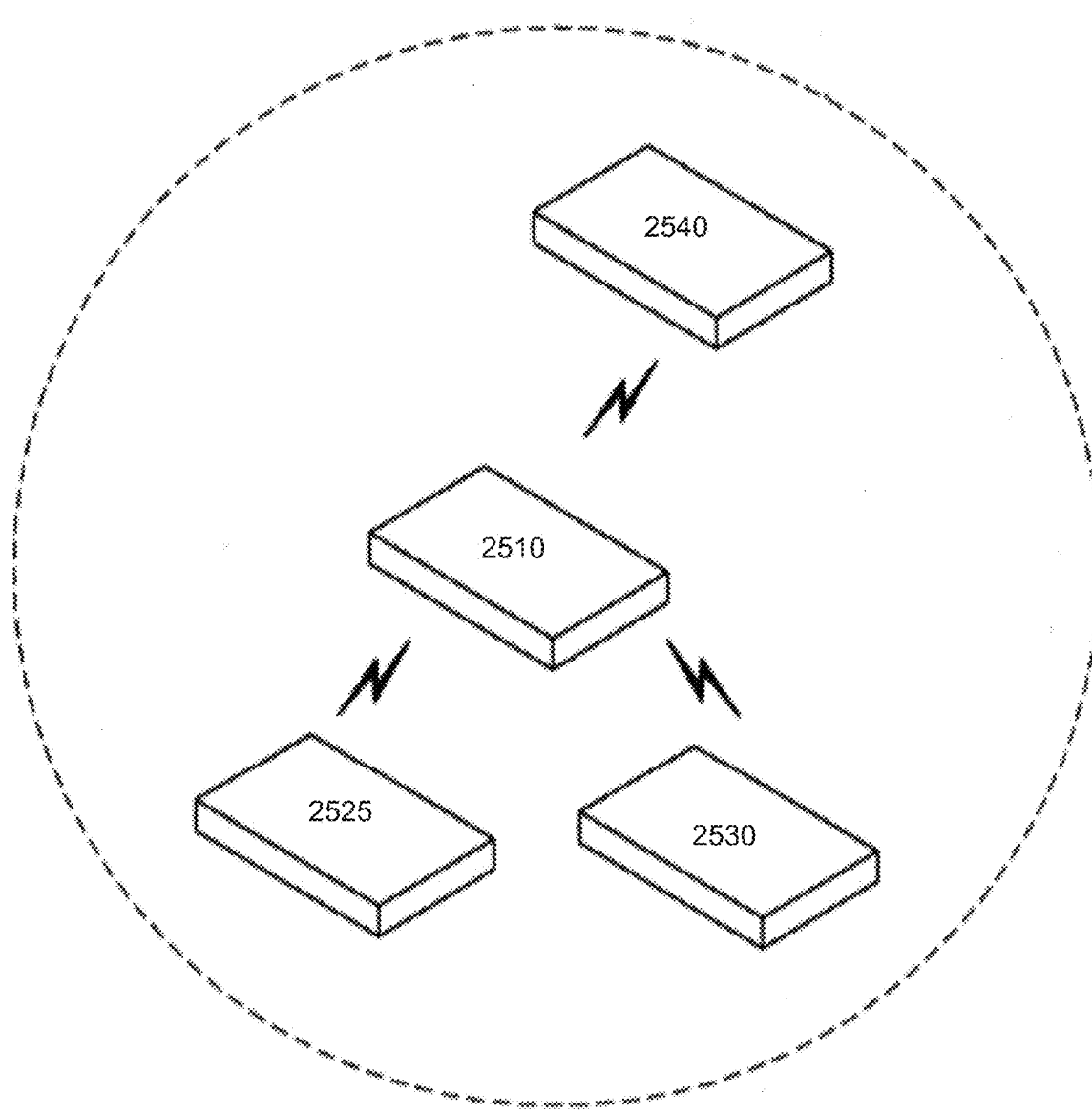
FIG. 25 depicts a wireless transfer station configured to communicate with other wireless transfer stations in accordance with an example.

FIG. 25 shows a wireless transfer station 2510 configured to communicate with other wireless transfer stations 2525, 2530, and/or 2540 and determine which of the one or more other wireless transfer stations 2525, 2530, and/or 2540 is capable and/or available to provide energy to a selected device and/or a selected wireless transfer station. In one example, the selected device or the selected wireless transfer station can send a wireless transfer request to the wireless transfer station. When the wireless transfer station 2510 is not compatible with the selected device or the wireless transfer station 2510 is not available to provide energy to the selected device, the wireless transfer station 2510 can communicate with the one or more other wireless transfer stations 2525, 2530, and/or 2540 to locate an available wireless transfer station of the one or more other wireless transfer stations 2525, 2530, and/or 2540 for the selected device or the selected wireless transfer station to receive wireless energy. When the wireless transfer station 2510 determines that available wireless transfer station can provide energy to the selected device or the selected wireless transfer station, the wireless transfer station 2510 can provide the selected device or the selected wireless transfer station with transfer station information for the available wireless transfer station.

In one embodiment, the transfer station information can include: directions to one of the other wireless transfer stations 2525, 2530, or 2540; authentication information to receive energy from the other wireless transfer stations 2525, 2530, or 2540; a number of available wireless transfer coils at the other wireless transfer stations 2525, 2530, or 2540; a type of wireless transfer coils available at the other wireless transfer stations 2525, 2530, or 2540; an energy capabilities of the other wireless transfer stations 2525, 2530, or 2540; and so forth. In one embodiment, when more than one of the other wireless transfer stations 2525, 2530, or 2540 are available to provide energy to the selected wireless transfer station or the selected device, the selected wireless transfer station or the selected device can select which one of the one or more other wireless transfer stations 2525, 2530, or 2540 to receive energy from based on charging criteria. The charging criteria can include: an energy output capability of each of the one or more available other wireless transfer stations 2525, 2530, or 2540; a location of each of the one or more available other wireless transfer stations 2525, 2530, or 2540; a distance from the selected device or the selected wireless transfer station to each of the one or more available other wireless transfer stations 2525, 2530, or 2540; a number of other devices or other wireless transfer stations receiving energy from each of the one or more available other wireless transfer stations 2525, 2530, or 2540, and so forth.

In one example, the wireless transfer station 2510 is not compatible with the selected device or the selected wireless transfer station when a wireless transfer coil of the selected device or wireless transfer coils of the selected wireless transfer station are a different shape or size than a wireless transfer coil of the wireless transfer station 2510. In another example, the wireless transfer station 2510 is not compatible with the selected device or the selected wireless transfer station when a wireless transfer coil of the selected device or a wireless transfer coil of the selected wireless transfer station receives data and/or wireless energy at a different resonant frequency range than a resonant frequency range of a wireless transfer coil of the wireless transfer station 2510.

Figure 26A:
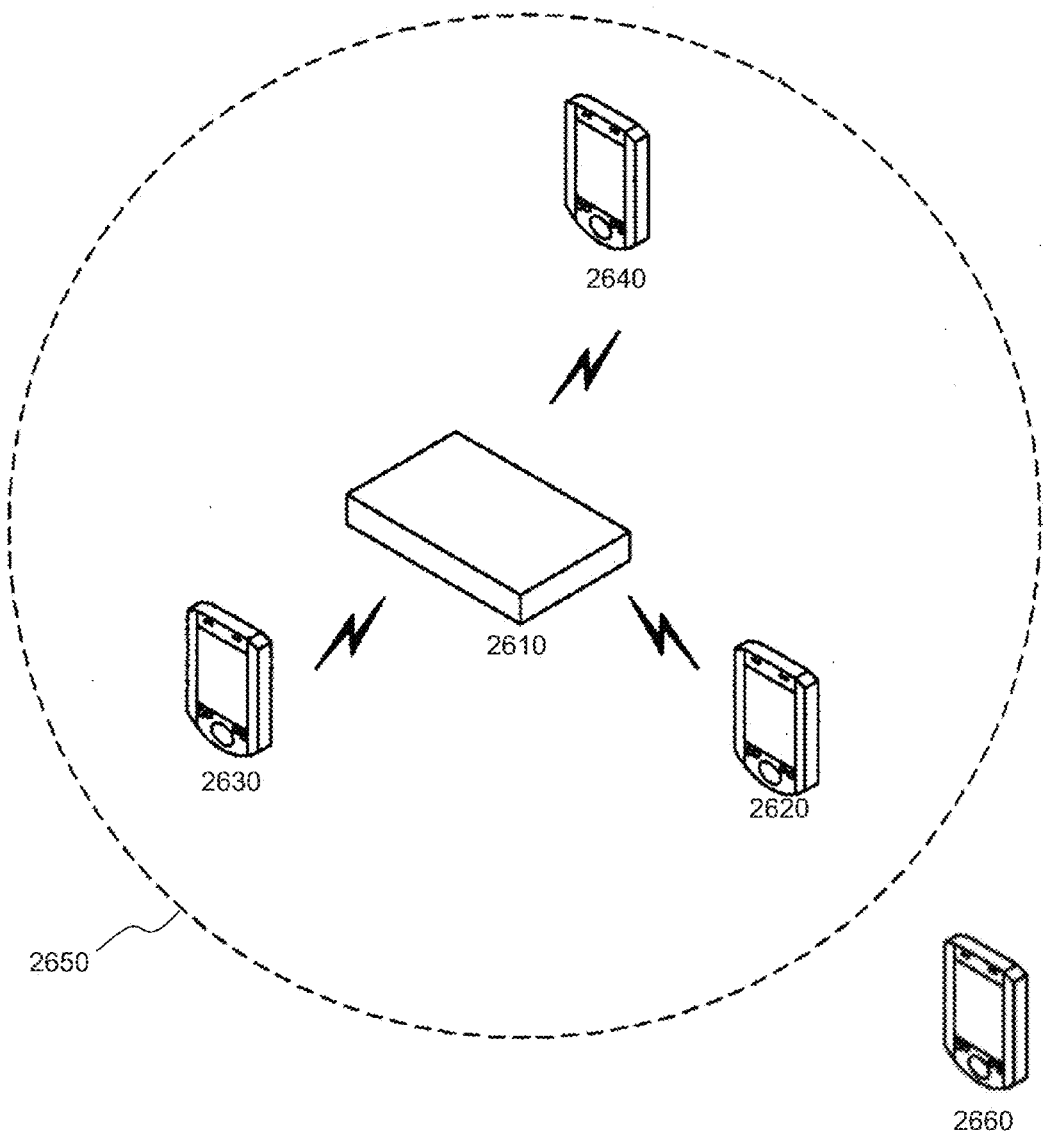
FIG. 26a depicts a wireless transfer station transferring energy and/or data with one or more wireless transfer stations and/or devices within a selected range in accordance with an example.

FIG. 26a shows a wireless transfer station 2610 transferring energy and/or data with one or more wireless transfer stations and/or devices 2620, 2630, and 2640 within a selected range 2650. In one embodiment, the wireless transfer station 2610 can adjust the selected range 2650 based on selected criteria, such as a number of wireless transfer stations and/or devices within a threshold range of the wireless transfer station 2610, a number of devices or other wireless transfer stations the wireless transfer station 2610 can support transferring energy and/or data to, and so forth. In one example, the wireless transfer station 2610 can transfer energy and/or data with wireless transfer stations and/or devices 2620, 2630, and 2640 that are within the selected range 2650 and not transfer energy and/or data with wireless transfer station and/or device 2660.

In one embodiment, a wireless transfer station can use a plurality of resonant frequencies to transfer energy to one or more devices or one or more other wireless transfer stations. In another embodiment, the wireless transfer station can provide different amounts of energy to different devices or other wireless transfer stations at different resonant frequencies. In one example, a first wireless transfer station can receive wireless energy from a primary wireless transfer station at a first resonant frequency and a second wireless transfer station can receive wireless energy from the primary wireless transfer station at a second resonant frequency.

In one embodiment, the primary wireless transfer station can set priority levels for the different devices or other wireless transfer stations receiving wireless energy at different resonant frequencies. In one example, a first wireless transfer station with a highest priority can receive wireless energy from the primary wireless transfer station at a first selected resonant frequency and a second wireless transfer station with a lower priority can receive wireless energy from the primary wireless transfer station at a second selected resonant frequency.

In one embodiment, the primary wireless transfer station may not have the capability to provide wireless energy to all the devices and/or other wireless transfer stations requesting wireless energy transfer. When the primary wireless transfer station does not have the capability to support all of the and/or other wireless transfer stations requesting wireless transfer requesting wireless energy transfer, the primary wireless transfer station can transfer energy to selected devices based on an energy transfer priority. In one embodiment, the primary wireless transfer station can select different resonant frequencies to transfer energy to different devices based on the energy transfer priority of the device.

In one example, the primary wireless transfer station can be capable of supporting energy transfer for a combination of up to 5 devices and/or other wireless transfer stations and 10 devices and other wireless transfer stations can request wireless energy transfer. In this example, the primary wireless transfer station can determine the priority of the 10 devices and/or other wireless transfer stations and select 5 devices and/or other wireless transfer stations to transfer energy to. The primary wireless transfer station can select one or more resonant frequencies to transfer energy to the 5 devices. The remaining devices can be de-selected (e.g. not selected) for charging by not tuning transmitting coils to frequencies of the remaining devices. In one embodiment, the remaining devices can be selected and charged after the first 5 have been charged.

In one embodiment, a transmission frequency of a wireless transfer coil of a wireless transfer station for transferring wireless energy can be based on a natural frequency of the wireless transfer station, a device, and/or a wireless transfer coil wireless of another wireless transfer station.

Figure 26B:
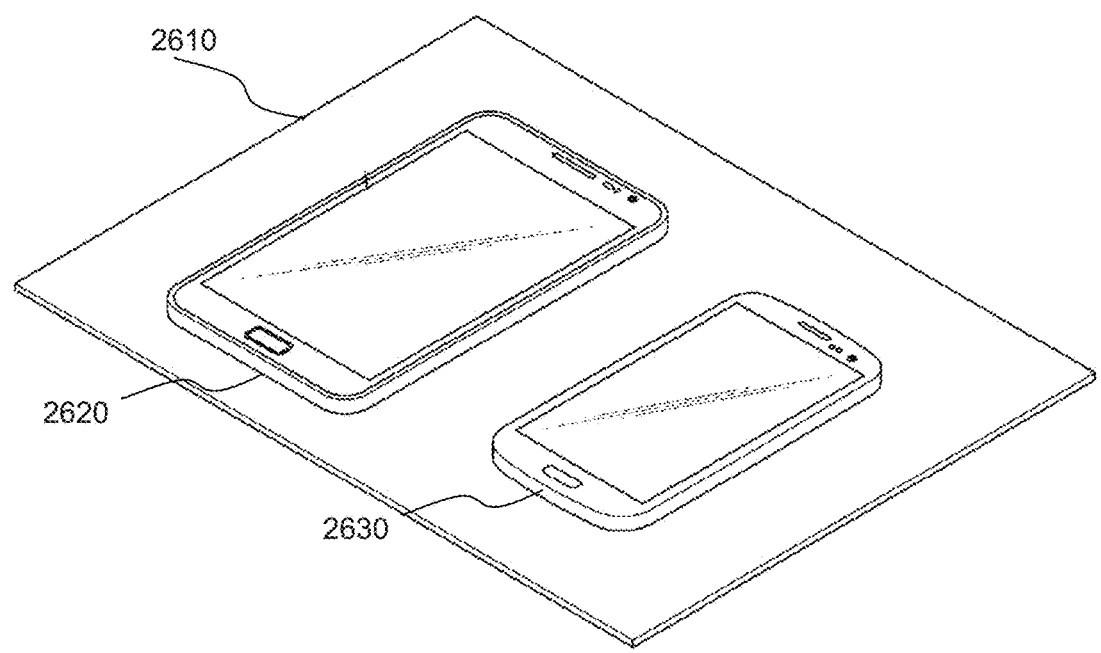
FIG. 26b depicts a wireless transfer station with authorized devices and unauthorized devices in accordance with an example.

FIG. 26b shows a wireless transfer station 2610 with devices 2620 and 2630 abutting a surface of the wireless transfer station 2610 with one or more wireless transfer coils for transferring energy and/or data. In one embodiment, the wireless transfer station 2610 can transfer energy and/or data with authorized device 2620 and/or unauthorized device 2630 and/or other wireless transfer stations. In one embodiment, only an authorized wireless transfer station and/or authorized device 2620 can transfer energy and/or data with the wireless transfer station 2610. In another embodiment, an unauthorized wireless transfer station and/or an unauthorized device 2630 can transfer energy and/or data with the wireless transfer station. In one example, when the wireless transfer station 2610 is integrated into a work surface of a wheeled medical cart, a doctor may place an unauthorized device 2630 (such as a personal cellphone) on the work surface of wheeled medical cart to receive energy and/or data. In one embodiment, when the unauthorized device 2630 is placed within a coverage range of the wireless transfer station 2610, the wireless transfer station 2610 can provide temporary access to the unauthorized device 2630. In one example, the unauthorized device 2630 can have a wireless transfer computer application on the unauthorized device 2630 to verify an identity of a user of the unauthorized device 2630 and a wireless transfer computer application can provide temporary access information to the wireless transfer station 2610. In this example, when the wireless transfer station 2610 receives the temporary access information, the wireless transfer station 2610 can transfer energy and/or data with the unauthorized device 2630.

In one embodiment, the wireless transfer computer application can provide a graphical interface for the user of the unauthorized device 2630 to input security information, such as a pin code or biometric authentication. In another embodiment, when the wireless energy computer application verifies input security information, the wireless energy computer application can communicate the temporary authorization to the wireless transfer station 2610. In another embodiment, when the temporary authorization is granted, the wireless transfer station 2610 can communicate connection information to the temporarily authorized device 2630, such as a decryption code to transfer data with the wireless transfer station 2610 or a frequency to transfer energy with the wireless transfer station 2610. In another embodiment, the temporary authorization can be for a selected period of time. In one example, when the wireless transfer station is part of a wheeled medical cart, a doctor may desire to use his smartphone (an unauthorized device 2630) to transfer data and/or energy with the wireless transfer station 2610 during the doctor's shift. When the smartphone is temporarily authorized, the smartphone can transfer energy and/or data with the wireless transfer station 2610 while the doctor is on duty for work, such as for a selected number of minutes or hours, and so forth.

In one embodiment, the temporary authorization can be valid while the temporarily authorized device 2630 is within the coverage range of the wireless transfer station 2610. In one example, when the wireless transfer station 2610 is part of a wheeled medical cart, a doctor may use his smartphone (an unauthorized device 2630) to transfer data and/or energy with the wireless transfer station 2610 while the doctor is adjacent to the wheeled medical cart. In another embodiment, when the temporarily authorized device 2630 leaves the coverage area of the wireless transfer station 2610, the temporary authorization can end. In another embodiment, when the temporarily authorized device 2630 returns to the wireless transfer station coverage area, to transfer data or energy again, the user ID of the temporarily authorized device 2630 can be verified again. In another embodiment, the temporarily authorized device 2630 can leave the coverage area for a selected period of time and re-enter the coverage area while maintaining the temporary authorization. In one example, a doctor can be using his smartphone to transfer data and/or energy with the wireless transfer station and then receive a phone call on his smartphone. In this example, the doctor can remove the smartphone from the coverage area to take the phone call and then replace the smartphone in the coverage area while maintaining the temporary authorization.

Traditionally, energy sources such as battery packs have different energy connectors for coupling the battery packs to different devices. Additionally, traditional battery packs have different energy connectors for different energy transfer levels. In one example, a battery coupled to a wheeled medical cart has one energy connector for transferring energy to the wheeled medical cart and a battery coupled to a medical fusion pump has a different energy connector for transferring energy to the medical fusion pump. Additionally, traditional battery packs for each type of device have different energy transfer levels corresponding to the device receiving the energy and require different battery pack configurations for each type of device. In one example, a wheeled medical cart may use a battery configured to transfer 20 volts and 5 amps of energy while a medical fusion pump may use a battery configured to transfer 10 volts and 3 amps. In one embodiment, a wireless transfer station can select the amount of energy, such as a voltage level or a current level, to wirelessly transfer to a device or other wireless transfer station based on a power configuration, such as a voltage or a current input requirement, of the device or other wireless transfer station. In one embodiment, the wireless transfer station can adjust or change an amount of energy transferred from the wireless transfer station to the device or other wireless transfer station by selecting different sizes of coils and/or tuning or detuning of coils (as discussed in the preceding paragraphs). In one example, the wireless transfer station can select a wireless transfer coil size or frequency to transfer 5 volts of energy to a 5-volt device and select a different wireless transfer coil size or frequency to transfer 10 volts of energy to a 10-volt device.

In one embodiment, the wireless transfer station can communicate with a device or another wireless transfer station and receive an energy requirement information of the device or the other wireless transfer station. The wireless energy battery pack can use the energy requirement information to determine the amount of energy to transfer to the device or the other wireless transfer station. In another embodiment, the wireless transfer station can receive a device ID or a station ID from the device or the other wireless transfer station, respectively, receiving energy from the wireless transfer station. The device ID or station ID can be associated with an energy requirement of the device or the other wireless transfer station and the wireless transfer station can adjust an energy level transfer based on the associated energy requirement.

One advantage of the wireless transfer station selecting the amount of energy to wirelessly transfer to a device or other wireless transfer station is that the wireless transfer station can be used with a plurality of different devices and/or other wireless transfer stations with different energy requirements. Another advantage of wireless transfer station having an adjustable energy level transfer capability can be to enable the wireless transfer station to be used with different devices and/or other wireless transfer stations with different energy level requirements without needing different energy connection adapters. In one example, the wireless transfer station can be connected to the wheeled medical cart, determine that the wheeled medical cart requires 20 volts and 5 amps of energy, and transfer the required energy. The wireless transfer station can later be swapped to a medical fusion pump, the wireless transfer station can determine the medical fusion pump requires 10 volts and 3 amps, and transfer the required energy.

In one embodiment, a wireless transfer station can communicate with one or more wireless transfer stations transferring energy data with the wireless transfer station to determine transfer information of the device and/or the other wireless transfer stations. The transfer information of the device and/or the wireless transfer station can include: a battery capacity level of the device or the other wireless transfer station, a priority level of the device and/or the wireless transfer station, a rate the device or the other wireless transfer station is consuming energy, a number of times the device or the other wireless transfer station has been charged, an estimation of the number of charges remaining for the device or the other wireless transfer station, an operational temperature of the device or the other wireless transfer station, an internal temperature of the device or the other wireless transfer station, a device identification (device ID) information, a wireless transfer station identification (station ID) information, and so forth. In one embodiment, the wireless transfer station can record and/or track the transfer information of the device and/or the other wireless transfer station. In one example, a plurality of devices and/or a plurality of other wireless transfer stations can each be assigned a device ID or station ID, respectively. The wireless transfer station can receive the transfer information for each device and/or for each other wireless transfer station in the coverage area of the wireless transfer station and associate the energy information with the device ID or station ID.

In one embodiment, the wireless transfer station can regulate an amount of wireless energy the device or the other wireless transfer station can receive. In one example, the wireless transfer station can communicate to a device a selected energy level limit that is a maximum energy that the device can receive from the wireless transfer station. In another embodiment, the device or the other wireless transfer station transferring energy and/or data with the wireless transfer station can include an energy control module to limit an amount of energy that the device or the other wireless transfer station can receive from the wireless transfer station. In one embodiment, the energy control module can be an operating system on the device or the other wireless transfer station. In another embodiment, the energy control module can be an energy regulator.

In one embodiment, the wireless transfer station can transfer different amounts of energy with different devices and/or other wireless transfer stations using different resonant frequencies. In another embodiment, the wireless transfer station can assign different devices or different other wireless transfer stations to receive energy and/or data using different frequencies and can adjust the amount of energy and/or data is transferred to each device or wireless transfer stations at the different frequencies.

In one embodiment, a wireless transfer station can receive identification information or security information from a device or another wireless transfer station requesting a wireless energy transfer. In another embodiment, the security information can include a pin code, a biometric authentication, and so forth. In another embodiment, the identification information can include a user identity (ID), a device ID, and/or a station ID.

In another embodiment, the wireless transfer station can use the identification information or security information to determine if the requesting device or the requesting other wireless transfer station is authorized to receive energy from the wireless transfer station. In another embodiment, when the device of the other wireless transfer station is not authorized to receive energy from the wireless transfer station, the wireless transfer station can deny or ignore the request to receive energy. In another embodiment, when the device of the other wireless transfer station is authorized to receive energy from the wireless transfer station, the wireless transfer station can then determine a priority that the requesting device or the other requesting wireless transfer station can receive energy relative to other devices and/or additional wireless transfer station.

In one embodiment, when the device or the other wireless transfer station is unable to provide security information and/or the wireless transfer station does not receive the security information, the wireless transfer station can deny the request to provide the wireless energy transfer. In another embodiment, when the device or the other wireless transfer station is unable to provide security information, the wireless transfer station can place the request to provide energy at the bottom of an energy-receiving queue.

In one embodiment, the wireless transfer station can assign different priority levels to different devices or other wireless transfer stations. The wireless transfer station can determine an amount of energy that the wireless transfer station has available to transfer to one or more devices and/or one or more other wireless transfer stations and prioritize the one or more devices and/or the one or more other wireless transfer stations that can receive energy and/or the amount of energy that the one or more devices and/or the one or more other wireless transfer stations can receive.

In one embodiment, the wireless transfer station can prioritize the amount of energy transferred to the one or more devices and the one or more other wireless transfer stations based on selected priority criteria. In one example, when 5 devices and 7 other wireless transfer stations each request to receive energy from a wireless transfer station and/or to continue to receive energy from the wireless transfer station, the wireless transfer station can prioritize the devices and other wireless transfer stations based on selected priority criteria. In one embodiment, the selected priority criteria can include: a type of the device, the wireless transfer station, and/or the other wireless transfer station; a present energy level of the device or the other wireless transfer station; a present energy level of the wireless transfer station; a number of devices or other wireless transfer stations that are requesting energy from the wireless transfer station, and so forth.

In one example, when a plurality of devices and/or other wireless transfer stations request to receive energy from the wireless transfer station, the wireless transfer station can determine a present energy level of one or more of the devices and/or the other wireless transfer stations and populate a priority list based on the present energy level of the one or more of the devices and/or the other wireless transfer stations. In one example, a device or other wireless transfer station with a lowest present energy level can be placed at the top of the list to receive an energy transfer, a device or other wireless transfer station with a second lowest present energy level can be placed second from the top of the list to receive an energy transfer, and so forth.

In another example, a first device can request energy and a second device can request energy from the wireless transfer station. The first device can be a smartphone and the second device can be a medical surgical tool. The wireless transfer station can determine that the medical surgical tool, based on the type of device, has a higher priority to receive energy than the smartphone and populate a priority list based on the type of device, the type of wireless transfer station, and/or the type of device coupled to the wireless transfer station. In one embodiment, the wireless transfer station can provide energy to the device, the wireless transfer station, and/or the device coupled to the wireless transfer station based on the priority list (such as providing energy to the medical surgical tool before the smartphone).

In one embodiment, the wireless transfer station can communicate to the one or more devices and/or the one or more wireless transfer stations a frequency on which each device or each wireless transfer station can receive energy, an amount of energy each device or each other wireless transfer station can receive, a period of time that each device or each wireless transfer station can receive the wireless energy, and so forth. In one embodiment, the wireless transfer station can coordinate transferring energy to different devices and other wireless transfer stations at different times using the coordination module, as discussed in the preceding paragraphs. In another embodiment, the wireless transfer station can determine the amount of energy the wireless transfer station transfers to each device and wireless transfer station. In one embodiment, the wireless transfer station can dynamically adjust the frequency that the energy is transferred on and/or the amount of energy transferred to each device or wireless transfer station.

In one embodiment, the wireless transfer station can assign different frequencies to the one or more devices and/or the one or more other wireless transfer stations to enable the wireless transfer station to differentiate the amount of energy each device or other wireless transfer station is receiving, e.g. enabling unique usage metering for each device or other wireless transfer station.

In one embodiment, the wireless transfer station can adjusts an amount of energy and/or number of transmitting coils transmitting energy based on a number of devices and/or other wireless transfer stations requesting energy and/or receiving energy.

In one embodiment, the wireless transfer station can adjust an amount of energy and/or number of wireless transfer coils transferring energy based on a number of devices and/or other wireless transfer stations requesting energy and/or receiving energy. In another embodiment, the wireless transfer station can alternate providing energy to one or more devices and/or other wireless transfer stations. In one example, the wireless transfer station can receive requests from multiple devices and other wireless transfer stations for an energy transfer. When the wireless transfer station does not have the capability to provide energy to all of the devices and the other wireless transfer stations requesting energy simultaneously, the wireless transfer station can provide energy to selected devices and/or other wireless transfer stations for a selected period of time and then switch to providing energy to different selected devices and other wireless transfer stations for a selected period of time.

One advantage of alternating providing energy to different devices and other wireless transfer stations can be to enable the wireless transfer station to provide energy to multiple devices and/or other wireless transfer stations while conserving energy. For example, if the wireless transfer station has 25 percent energy remaining and a plurality of the devices and the other wireless transfer stations are requesting to receive energy, the wireless transfer station can alternate providing energy to the devices and the other wireless transfer stations to enable the devices and the other wireless transfer stations to avoid becoming completely drained of energy, while conserving energy of the wireless transfer station until the wireless transfer station can be recharged.

In one embodiment, the wireless transfer station can charge a first device or other wireless transfer station or a first group of devices and/or other wireless transfer stations first for a selected period of time or until a full charge level is reach, and then charge a second device or other wireless transfer station or a second group of devices and/or other wireless transfer stations second for a selected period of time or until a full charge level is reach, and so forth.

In one embodiment, the wireless transfer station can select the first device or other wireless transfer station or a first group of devices and/or other wireless transfer stations to charge based on the rate that the each device, other wireless transfer station, or group of devices and/or other wireless transfer stations can receive a charge. In one example, a first device or other wireless transfer station or a first group of devices and/or other wireless transfer stations can receive a charge from the wireless transfer station faster than a second device or other wireless transfer station or a second group of devices and/or other wireless transfer stations. One advantage of charging a device, other wireless transfer station, or group of devices and/or other wireless transfer stations that can receive a charge faster is that the devices or wireless transfer stations can be charged more quickly than other slower charging device and can more quickly be ready for use.

In one embodiment, the wireless transfer station can charge the device and/or the other wireless transfer station based on warranty characteristics. In another embodiment, the warranty characteristics can include: a state of health of the device and/or the other wireless transfer station, an age of the device and/or the other wireless transfer station, a number of times the device and/or the other wireless transfer station has been charged, a number of uses of the device and/or the other wireless transfer station, and so forth. In one example, a first wireless transfer station can be manufactured or purchased more recently than a second wireless transfer station. In this example, a primary wireless transfer station can transfer energy to the second wireless transfer station before transferring energy to the first wireless transfer station. One advantage of charging an older wireless transfer station or device before a newer wireless transfer station or device is that the primary wireless transfer station can manage a usage of the older wireless transfer station or device and the newer wireless transfer station or device. In one example, when a newer wireless transfer station is purchased, a user may tend to use the newer wireless transfer station before using the older wireless transfer station, thereby wearing out the newer wireless transfer station more quickly than the older wireless transfer station. In this example, when the newer wireless transfer station is worn out more quickly than the older wireless transfer station, the newer wireless transfer station may default on a manufacture warranty based on the heavier usage. When the older wireless transfer station is charged first, a user may use the older wireless transfer station before the newer wireless transfer station and balance the usage of the wireless transfer stations.

In one embodiment, a wireless transfer station can include a display to indicate to a user which device and/or wireless transfer station to use first. In one example, when two wireless transfer stations are both fully charged and ready for use, a display can indicate one of the wireless transfer stations to use first. In one example, a wireless transfer stations can communicate with one or more other wireless transfer stations to determine which wireless transfer station will indicate to be selected first for use from a plurality of wireless transfer stations. In one example, when a plurality of wireless transfer stations are fully charged, the one wireless transfer station that is oldest can indicate to a user to use the oldest wireless transfer station first.

In one embodiment, the wireless transfer station can receive usage information from one or more devices and/or one or more other wireless transfer stations and prioritize a transfer of energy and/or data to the one or more devices and/or the one or more other wireless transfer stations based on the usage information. In another embodiment, the usage information can include: a location of the wireless transfer station; a location of the one or more devices and/or the one or more other wireless transfer stations; a voltage capacity of the wireless transfer station, the one or more devices, and/or the one or more other wireless transfer stations; a current capacity of the wireless transfer station, the one or more devices, and/or the one or more other wireless transfer stations; a charge level of the wireless transfer station, the one or more devices, and/or the one or more other wireless transfer stations; an internal temperature or an operating temperature of the wireless transfer station, the one or more devices, and/or the one or more other wireless transfer stations; a state of health of the wireless transfer station, the one or more devices, and/or the one or more other wireless transfer stations; a state of charge of the wireless transfer station, the one or more devices, and/or the one or more other wireless transfer stations; a type of the wireless transfer station, the one or more devices, and/or the one or more other wireless transfer stations; a number of charging cycles of one or more batteries of the wireless transfer station, the one or more devices, and/or the one or more other wireless transfer stations; a number of charging cycles of the wireless transfer station, the one or more devices, and/or the one or more other wireless transfer stations; a warranty period of the wireless transfer station, the one or more devices, and/or the one or more other wireless transfer stations; an energy transfer threshold of the wireless transfer station, the one or more devices, and/or the one or more other wireless transfer stations; a number of the one or more devices and/or the one or more other wireless transfer stations receiving wireless energy from the wireless transfer station; an age of the wireless transfer station, the one or more devices, and/or the one or more other wireless transfer stations; an operational level of the wireless transfer station, the one or more devices, and/or the one or more other wireless transfer stations; a warranty time period of the wireless transfer station, the one or more devices, and/or the one or more other wireless transfer stations; a time since a last recharge of the wireless transfer station, the one or more devices, and/or the one or more other wireless transfer stations; a capacity level of a plurality of batteries in the wireless transfer station, the one or more devices, and/or the one or more other wireless transfer stations; a battery capacity level of a battery in the wireless transfer station, the one or more devices, and/or the one or more other wireless transfer stations; and/or a usage demand rate of the wireless transfer station, the one or more devices, and/or the one or more other wireless transfer stations.

In one example, the wireless transfer station can use the usage information of the one or more devices and/or the one or more other wireless transfer stations to balance out an amount of times a battery is charged for a selected period of time. In this example, the wireless transfer station may cease charging a device or other wireless transfer station that has been recharged a number of times that exceeds a threshold number of times for recharge in a selected time period.

In one embodiment, the wireless transfer station can determine a demand for one or more devices and/or other wireless transfer stations and adjust a charging rate of the one or more devices and/or other wireless transfer stations based on the demand. In one example, when the demand is relatively low for one or more other wireless transfer stations, the wireless transfer station can charge the one or more other wireless transfer stations at a slower rate than when demand is relatively high. In another example, when the demand is relatively high for one or more other wireless transfer stations, the wireless transfer station can charge the one or more other wireless transfer stations at a faster rate then when the demand is relatively low.

In one embodiment, demand can be determined based on a number of devices and/or other wireless transfer stations that are removed from receiving a charge from the wireless transfer station (i.e. removed for use) and/or a number of devices and/or other wireless transfer stations that are requesting an energy transfer from the wireless transfer station. In one example, when the rate of devices and/or other wireless transfer stations removed from charging and/or requesting energy transfer increases, the demand may be increasing or high. In another example, when the rate of devices and/or other wireless transfer stations removed from charging and/or requesting energy transfer decreases, the demand may be decreasing or low. In another embodiment, the wireless transfer station can include a graphical user interface and receive a demand input from a graphical user interface indicating a demand level.

One advantage of adjusting the charging rate based on demand can be to preserve battery life of a device or wireless transfer station when demand is low while providing wireless transfer stations or devices more quickly to users when a demand is high. In one example, when a battery of a device or a battery of wireless transfer station is charged at a slower rate, an amount of oxidation from chemicals in the battery will be reduce compared to charging a battery at a faster rate, thereby preserving the battery life and maintaining an overall health of the battery.

In one embodiment, the wireless transfer station can determine a coil alignment between a wireless transfer coil of the wireless transfer station and a wireless transfer coil of a device or another wireless transfer station. In one embodiment, the wireless transfer station can prioritize an energy transfer to one or more devices and/or other wireless transfer stations based on the coil alignment. In one example, when a coil alignment between a first wireless transfer station and a primary wireless transfer station is fully aligned and a coil alignment between a second wireless transfer station and the primary wireless transfer station is partially aligned, the primary wireless transfer station can transfer energy to the first wireless transfer station before transferring energy to the second wireless transfer station.

Figure 27:
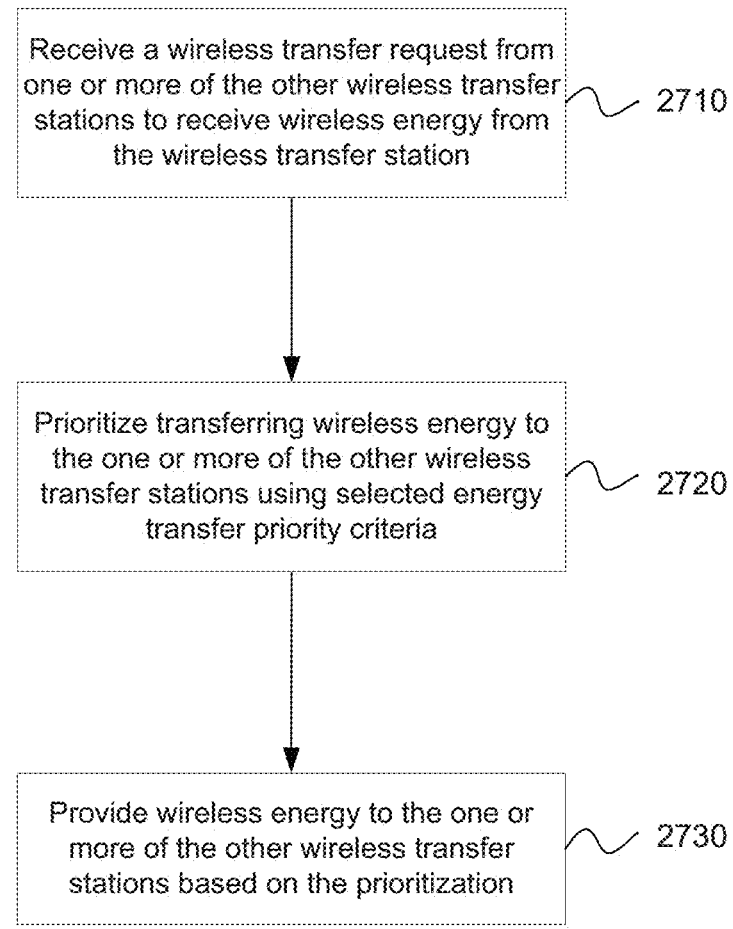
FIG. 27 depicts the functionality of computer circuitry with a wireless transfer station that is operable to wirelessly provide energy to other wireless transfer stations in accordance with an example.

FIG. 27 uses a flow chart 2270 to illustrate the functionality of one embodiment of computer circuitry of the wireless transfer station operable to wirelessly provide energy to other wireless transfer stations. The functionality may be implemented as a method or the functionality may be executed as instructions on a machine, where the instructions are included on at least one computer readable medium or one non-transitory machine readable storage medium. The computer circuitry can be configured to receive a wireless transfer request from one or more of the other wireless transfer stations to receive wireless energy from the wireless transfer station, as in block 2710. The computer circuitry can be further configured to prioritize transferring wireless energy to the one or more of the other wireless transfer stations using selected energy transfer priority criteria, as in block 2727. The computer circuitry can be further configured to provide wireless energy to the one or more of the other wireless transfer stations based on the prioritization, as in block 2730.

In one embodiment, the energy transfer priority criteria can include: a location of the wireless transfer station; a voltage capacity of the wireless transfer station; a current capacity of the wireless transfer station; a charge level of the wireless transfer station; a temperature of the wireless transfer station; a state of health of the wireless transfer station; a state of charge of the wireless transfer station; a type of the wireless transfer station; a number of charging cycles of one or more batteries of the wireless transfer station; a number of charging cycles of the wireless transfer station; a warranty period of the wireless transfer station; an energy transfer threshold of the wireless transfer station; a number of other wireless transfer stations receiving wireless energy from the product; an age of the wireless transfer station; an operational level of the wireless transfer station; a warranty time period of the wireless transfer station; a time since a last recharge of the wireless transfer station; a capacity level of a plurality of batteries in the wireless transfer station; a battery capacity level of a battery in the wireless transfer station; a usage demand rate of the wireless transfer station; or a usage demand rate of the other wireless transfers stations.

In one embodiment, the computer circuitry can be configured to determine a state of health of the other wireless transfer stations and prioritize transferring wireless energy to one or more of the other wireless transfer stations based on the state of health of each of the one or more other wireless transfer stations. In another embodiment, the state of health can include: an age of a selected wireless transfer station of the other wireless transfer stations; an age of a battery of the selected wireless transfer station; a number of charging cycles of the selected wireless transfer station; a number of charging cycles of the battery of the selected wireless transfer station; an operational level of the selected wireless transfer station; an operational level of the battery of the selected wireless transfer station; a warranty time period of the selected wireless transfer station; or a warranty time period of the battery of the selected wireless transfer station.

In one embodiment, the computer circuitry can be configured to determine energy transfer rate information for one or more of the other wireless transfer stations, wherein the energy transfer rate information includes: a type of a selected wireless transfer station of the other wireless transfer stations; a warranty period of the selected wireless transfer station; an energy transfer threshold of the selected wireless transfer station; a number of other wireless transfer stations receiving wireless energy from the wireless transfer station; or a usage demand rate of the other wireless transfer stations. In another embodiment, the computer circuitry can be further configured to prioritize the wireless energy transfer to the one or more of the other wireless transfer stations based on the energy transfer rate information. In another embodiment, the computer circuitry can be further configured to provide wireless energy to the one or more of the other wireless transfer stations at an energy transfer rate that is based on the energy transfer rate information. In another embodiment, the computer circuitry can be further configured to prioritize the wireless energy transfer to the one or more of the other wireless transfer stations based on: an energy receive rate capability of a selected wireless transfer station of the one or more of the other wireless transfer stations or a charge level of the selected wireless transfer station.

In one embodiment, the computer circuitry can be configured to sequentially provide wireless energy to the one or more wireless transfer stations based on the prioritization or provide wireless energy to a plurality of the other wireless transfer stations at a substantially same time based on the prioritization. In another embodiment, the computer circuitry can be further configured to determine an energy transfer efficiency rate between the wireless transfer station and the one or more of the other wireless transfer stations and prioritize the wireless energy transfer to the one or more of the other wireless transfer stations based on the energy transfer efficiency rate. In another embodiment, the energy transfer efficiency rate is determined based on: a distance between a wireless transfer coil of the wireless transfer station and a wireless transfer coil of the one or more of the other wireless transfer stations or an alignment between the wireless transfer coil of the wireless transfer station and the wireless transfer coil of the one or more of the other wireless transfer stations.

In one embodiment, the computer circuitry can be configured to determine one or more selected wireless transfer stations not to transfer wireless energy to or to delay transferring wireless energy to and communicate a wireless transfer request denial to the selected wireless transfer stations requesting a wireless energy transfer request. In another embodiment, the computer circuitry can be further configured to determine the selected wireless transfer stations not to transfer wireless energy to or to delay transferring wireless energy to based on: warranty information of the selected wireless transfer stations; an error event of the selected wireless transfer stations; an operating temperature of the selected wireless transfer stations; or a number of charging cycles of the selected wireless transfer stations. In another embodiment, the wireless transfer request denial can include: an estimated wait time indicating when one or more of the selected wireless transfer stations will receive wireless energy or an event message indicating when the one or more of the selected wireless transfer stations will receive energy based on the selected energy transfer priority criteria for prioritization.

In another embodiment, the energy transfer priority criteria can include: a location of the wireless transfer station; a voltage capacity of the wireless transfer station; a current capacity of the wireless transfer station; a charge level of the wireless transfer station; a temperature of the wireless transfer station; a state of health of the wireless transfer station; a state of charge of the wireless transfer station; a type of the wireless transfer station; a number of charging cycles of one or more batteries of the wireless transfer station; a number of charging cycles of the wireless transfer station; a warranty period of the wireless transfer station; an energy transfer threshold of the wireless transfer station; a number of other wireless transfer stations receiving wireless energy from the product; an age of the wireless transfer station; an operational level of the wireless transfer station; a warranty time period of the wireless transfer station; a time since a last recharge of the wireless transfer station; a capacity level of a plurality of batteries in the wireless transfer station; a battery capacity level of a battery in the wireless transfer station; a usage demand rate of the wireless transfer station; or a usage demand rate of the other wireless transfers stations.

Figure 28:
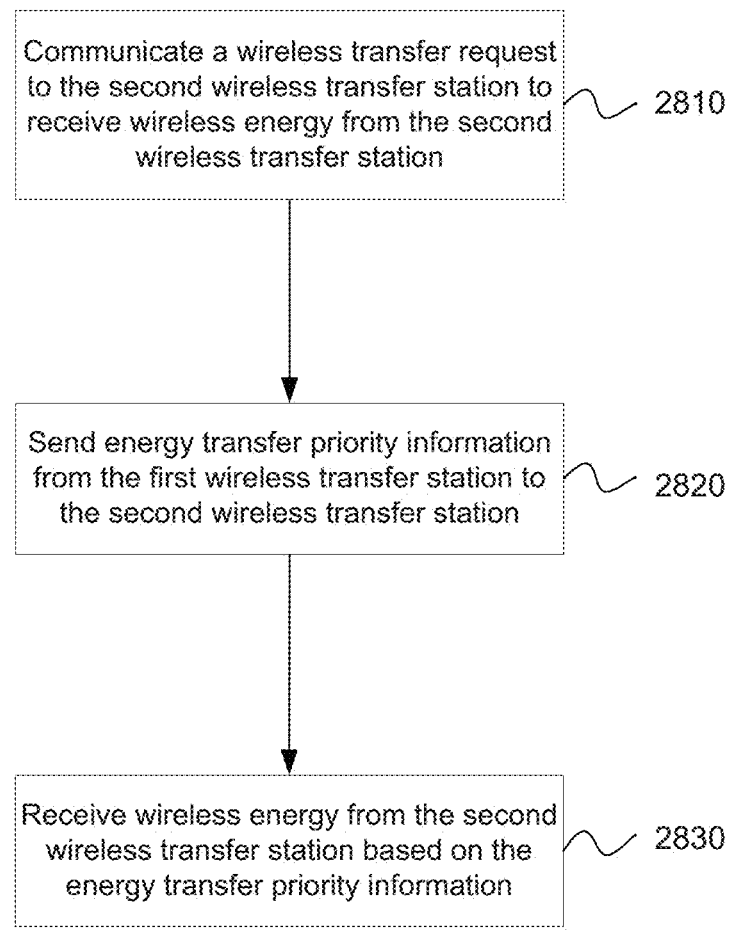
FIG. 28 depicts the functionality of computer circuitry with a wireless transfer station that is operable to wirelessly receive energy from another wireless transfer station in accordance with an example.

FIG. 28 uses a flow chart 2800 to illustrate the functionality of one embodiment of the first wireless transfer station operable to wirelessly receive energy from a second wireless transfer station. The functionality may be implemented as a method or the functionality may be executed as instructions on a machine, where the instructions are included on at least one computer readable medium or one non-transitory machine readable storage medium. The computer circuitry can be configured to communicate a wireless transfer request to the second wireless transfer station to receive wireless energy from the second wireless transfer station, as in block 2810. The computer circuitry can be further configured to send energy transfer priority information from the first wireless transfer station to the second wireless transfer station, as in block 2820. The computer circuitry can be further configured to receive wireless energy from the second wireless transfer station based on the energy transfer priority information, as in block 2830.

In one embodiment, the computer circuitry can be further configured to receive a request for energy transfer priority information from the second wireless transfer station. In another embodiment, the computer circuitry can be further configured to communicate with one or more other wireless transfer stations. In another embodiment, the computer circuitry can be further configured to determine a firmware version of firmware or a software version of software operating at the first wireless transfer station and receive wireless energy from the second wireless transfer station based on the firmware version or the software version of the first wireless transfer station.

Figure 29:
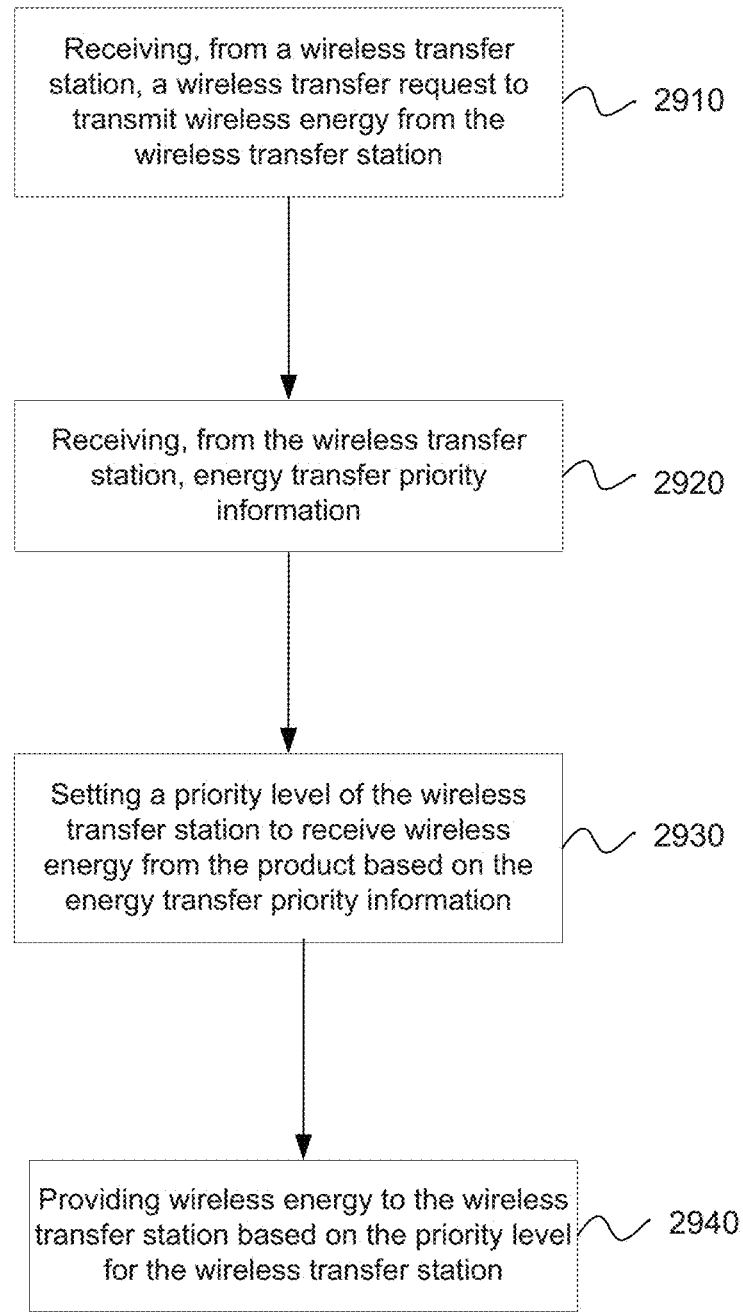
FIG. 29 depicts a product including a non-transitory storage medium having stored thereon instructions that are adapted to be executed to implement a method of prioritizing a distribution of wireless energy to a plurality of wireless transfer stations in accordance with an example.

Another example provides functionality 2900 of product including a non-transitory storage medium having stored thereon instructions that are adapted to be executed to implement a method of prioritizing a distribution of wireless energy to a plurality of wireless transfer stations, as shown in the flow chart in FIG. 29. The instructions of the product can be implemented as a method or as instructions on a machine, where the instructions are included on at least one computer readable medium or one non-transitory machine readable storage medium. The method can comprise receiving, from a wireless transfer station, a wireless transfer request to transmit wireless energy from the wireless transfer station, as in block 2910. The method can further comprise receiving, from the wireless transfer station, energy transfer priority information, as in block 2920. The method can further comprise setting a priority level of the wireless transfer station to receive wireless energy from the product based on the energy transfer priority information, as in block 2930. The method can further comprise providing wireless energy to the wireless transfer station based on the priority level for the wireless transfer station, as in block 2940.

In one embodiment, the method can further comprise providing wireless energy to the wireless transfer station when the priority level for the wireless transfer station is within a priority level threshold. In another embodiment, the method can further comprise receiving the energy transfer priority information from another device or receiving the energy transfer priority information from a graphical user interface in communication with the product.

In one embodiment, the energy transfer priority information includes: a location of the wireless transfer station; a voltage capacity of the wireless transfer station; a current capacity of the wireless transfer station; a charge level of the wireless transfer station; a temperature of the wireless transfer station; a state of health of the wireless transfer station; a state of charge of the wireless transfer station; a type of the wireless transfer station; a number of charging cycles of one or more batteries of the wireless transfer station; a number of charging cycles of the wireless transfer station; a warranty period of the wireless transfer station; an energy transfer threshold of the wireless transfer station; a number of other wireless transfer stations receiving wireless energy from the product; an age of the wireless transfer station; an operational level of the wireless transfer station; a warranty time period of the wireless transfer station; a time since a last recharge of the wireless transfer station; a capacity level of a plurality of batteries in the wireless transfer station; a battery capacity level of a battery in the wireless transfer station; a usage demand rate of the wireless transfer station; or a usage demand rate of the other wireless transfers stations.

In one embodiment, the method can further comprise determining an amount of time to charge the wireless transfer station and prioritizing when the wireless transfer station receives wireless energy from the product based on the amount of time to charge the wireless transfer station. In another embodiment, the method can further comprise communicating with the wireless transfer station to determine an amount of energy provided to the wireless transfer station. In another embodiment, the method can further comprise prioritizing when the wireless transfer station receives wireless energy from the product based on a safety event of the product or a safety event of the wireless transfer station.

In one embodiment, the safety event includes: a temperature threshold of the wireless transfer station; a temperature threshold of a single battery of the wireless transfer station; an error at the wireless transfer station; a current level of the wireless transfer station; a current level of the single battery of the wireless transfer station; an internal short in the wireless transfer station; an internal short in the single battery of the wireless transfer station; an internal pressure level of the wireless transfer station; an internal pressure level of the single battery of the wireless transfer station; a communication error between the product and the wireless transfer station; and a cell imbalance of one or more batteries in the wireless transfers station.

Figure 30:
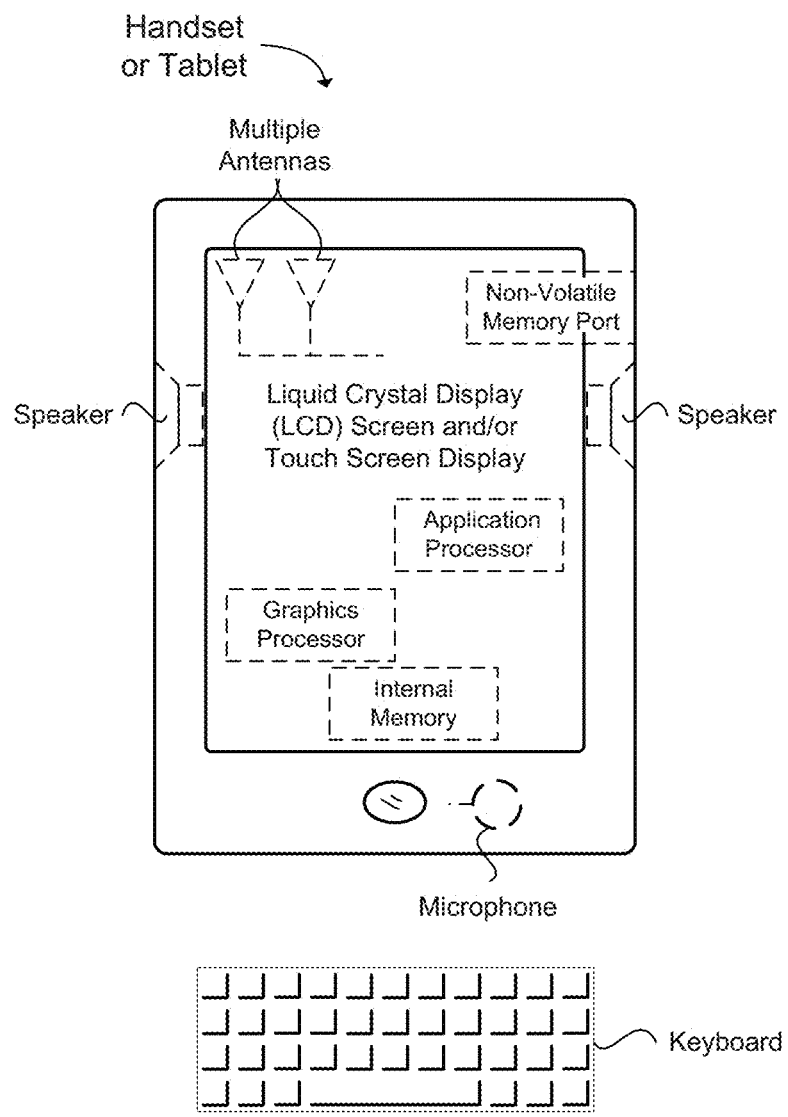
FIG. 30 illustrates a diagram of a device in accordance with an example.

FIG. 30 provides an example illustration of the device, such as a user equipment (UE), a mobile station (MS), a mobile wireless device, a mobile communication device, a tablet, a handset, or other type of device. The device can include one or more antennas configured to communicate with a node or transmission station, such as a base station (BS), an evolved Node B (eNode B), a baseband unit (BBU), a remote radio head (RRH), a remote radio equipment (RRE), a relay station (RS), a radio equipment (RE), a remote radio unit (RRU), a central processing module (CPM), or other type of wireless wide area network (WWAN) access point. The device can be configured to communicate using at least one wireless communication standard including 3GPP LTE, WiMAX, High Speed Packet Access (HSPA), Bluetooth, and Wi-Fi. The device can communicate using separate antennas for each wireless communication standard or shared antennas for multiple wireless communication standards. The device can communicate in a wireless local area network (WLAN), a wireless personal area network (WPAN), and/or a WWAN.

FIG. 30 also provides an illustration of a microphone and one or more speakers that can be used for audio input and output from the device. The display screen may be a liquid crystal display (LCD) screen, or other type of display screen such as an organic light emitting diode (OLED) display. The display screen can be configured as a touch screen. The touch screen may use capacitive, resistive, or another type of touch screen technology. An application processor and a graphics processor can be coupled to internal memory to provide processing and display capabilities. A non-volatile memory port can also be used to provide data input/output options to a user. The non-volatile memory port may also be used to expand the memory capabilities of the device. A keyboard may be integrated with the device or wirelessly connected to the device to provide additional user input. A virtual keyboard may also be provided using the touch screen.

Various techniques, or certain aspects or portions thereof, may take the form of program code (i.e., instructions) embodied in tangible media, such as floppy diskettes, CD-ROMs, hard drives, non-transitory computer readable storage medium, or any other machine-readable storage medium wherein, when the program code is loaded into and executed by a machine, such as a computer, the machine becomes an apparatus for practicing the various techniques. In the case of program code execution on programmable computers, the computing device may include a processor, a storage medium readable by the processor (including volatile and non-volatile memory and/or storage elements), at least one input device, and at least one output device. The volatile and non-volatile memory and/or storage elements may be a RAM, EPROM, flash drive, optical drive, magnetic hard drive, or other medium for storing electronic data. The base station and mobile station may also include a transceiver module, a counter module, a processing module, and/or a clock module or timer module. One or more programs that may implement or utilize the various techniques described herein may use an application programming interface (API), reusable controls, and the like. Such programs may be implemented in a high level procedural or object oriented programming language to communicate with a computer system. However, the program(s) may be implemented in assembly or machine language, if desired. In any case, the language may be a compiled or interpreted language, and combined with hardware implementations.

It should be understood that many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more physical or logical blocks of computer instructions, which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of executable code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. The modules may be passive or active, including agents operable to perform desired functions.

Reference throughout this specification to "an example" means that a particular feature, structure, or characteristic described in connection with the example is included in at least one embodiment of the present invention. Thus, appearances of the phrases "in an example" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as defacto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of layouts, distances, network examples, etc., to provide a thorough understanding of embodiments of the invention. One skilled in the relevant art will recognize, however, that the invention can be practiced without one or more of the specific details, or with other methods, components, layouts, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A wireless transfer station operable to wirelessly provide energy to other wireless transfer stations, the wireless transfer station having computer circuitry configured to:
receive a wireless energy transfer request from each of a plurality of the other wireless transfer stations, each wireless energy transfer request including energy transfer priority criteria, including an operating temperature of the corresponding other wireless transfer station;
prioritize transferring wireless energy to the plurality of other wireless transfer stations based on the energy transfer priority criteria; and
provide wireless energy to at least one of the plurality of other wireless transfer stations based on the prioritization.

2. The wireless transfer station of claim 1, wherein the energy transfer priority criteria of each wireless energy transfer request further includes:
a location of the corresponding other wireless transfer station;
a type of the corresponding other wireless transfer station; and
a time since a last recharge of the corresponding other wireless transfer station.

3. The wireless transfer station of claim 1, wherein the energy transfer priority criteria of each wireless energy transfer request further includes:
a usage demand rate of the corresponding other wireless transfer station.

4. The wireless transfer station of claim 1, wherein the energy transfer priority criteria of each wireless energy transfer request further includes:
an age of the corresponding wireless transfer station;
an age of a battery of the corresponding other wireless transfer station;
a number of charging cycles of the corresponding other wireless transfer station; and
a number of charging cycles of the battery of the corresponding other wireless transfer station.

5. The wireless transfer station of claim 1, wherein the energy transfer priority criteria of each wireless energy transfer request further includes:
a warranty period of the corresponding other wireless transfer station.

6. The wireless transfer station of claim 1, wherein the computer circuitry is further configured to provide wireless energy to the plurality of other wireless transfer stations at an energy transfer rate that is based on the energy transfer rate of each of the other wireless transfer stations.

7. The wireless transfer station of claim 1, wherein the energy transfer priority criteria of each wireless energy transfer request further includes
an energy receive rate capability of the corresponding other wireless transfer station; and
a charge level of the corresponding other wireless transfer station.

8. The wireless transfer station of claim 1, wherein the computer circuitry is further configured to:
sequentially provide wireless energy to the plurality of other wireless transfer stations based on the prioritization.

9. The wireless transfer station of claim 1, wherein the computer circuitry is further configured to:
determine an energy transfer efficiency rate between the wireless transfer station and each of the plurality of other wireless transfer stations; and
prioritize the wireless energy transfer to the plurality of other wireless transfer stations based on the energy transfer efficiency rate,
wherein the energy transfer efficiency rate is determined based on:
a distance between a wireless transfer coil of the wireless transfer station and a wireless transfer coil of each of the plurality of other wireless transfer stations; and
an alignment between the wireless transfer coil of the wireless transfer station and the wireless transfer coil of each of the plurality of other wireless transfer stations.

10. The computer circuitry of claim 1, further configured to:
determine one or more selected other wireless transfer stations not to transfer wireless energy to or to delay transferring wireless energy to based on the energy transfer priority criteria; and
communicate a wireless transfer request denial to the one or more selected other wireless transfer stations;
wherein the wireless transfer request denial includes an estimated wait time indicating when the one or more selected other wireless transfer stations will receive wireless energy, and an event message indicating when the one or more selected other wireless transfer stations will receive energy based on the energy transfer priority criteria.

11. The computer circuitry of claim 10, wherein the energy transfer priority criteria further includes:
a location of the wireless transfer station;
a warranty period of the wireless transfer station; and
an age of the wireless transfer station.

12. A first wireless transfer station operable to wirelessly receive energy from a second wireless transfer station, the first wireless transfer station having computer circuitry configured to:
communicate a wireless transfer request to the second wireless transfer station to receive wireless energy from the second wireless transfer station;
determine a firmware version of firmware or a software version of software operating at the first wireless transfer station;
send energy transfer priority information, including information related to the firmware version or software version operating at the first wireless transfer station, from the first wireless transfer station to the second wireless transfer station; and
receive wireless energy from the second wireless transfer station based on the energy transfer priority information.

13. The first wireless transfer station of claim 12, wherein the computer circuity is further configured to receive a request for energy transfer priority information from the second wireless transfer station.

14. The first wireless transfer station of claim 12, wherein the first wireless transfer station is further configured to communicate with one or more other wireless transfer stations configured to receive wireless energy from the second transfer station.

15. A product including a non-transitory storage medium having stored thereon instructions that are adapted to be executed to implement a method of prioritizing a distribution of wireless energy to a plurality of wireless transfer stations, the method comprising:
   receiving, from a wireless transfer station, a wireless transfer request to transmit wireless energy from the wireless transfer station;
   receiving, from the wireless transfer station, energy transfer priority information including an energy transfer efficiency rate of the wireless transfer station;
   setting a priority level of the wireless transfer station to receive wireless energy from the product based on the energy transfer priority information; and
   providing wireless energy to the wireless transfer station based on the priority level for the wireless transfer station.

16. The product of claim 15, further comprising providing wireless energy to the wireless transfer station when the priority level for the wireless transfer station is within a priority level threshold.

17. The product of claim 15, further comprising receiving the energy transfer priority information from another device.

18. The product of claim 15, further comprising:
   determining an amount of time to charge the wireless transfer station; and
   prioritizing when the wireless transfer station receives wireless energy from the product based on the amount of time to charge the wireless transfer station.

19. The product of claim 15, further comprising communicating with the wireless transfer station to determine an amount of energy provided to the wireless transfer station.

20. The product of claim 15, further comprising prioritizing when the wireless transfer station receives wireless energy from the product based on a safety event of the product or a safety event of the wireless transfer station.

21. The product of claim 20, wherein the safety event can be any of:
   a temperature threshold of the wireless transfer station;
   a temperature threshold of a single battery of the wireless transfer station;
   an error at the wireless transfer station;
   a current level of the wireless transfer station;
   a current level of the single battery of the wireless transfer station;
   an internal short in the wireless transfer station;
   an internal short in the single battery of the wireless transfer station;
   an internal pressure level of the wireless transfer station;
   an internal pressure level of the single battery of the wireless transfer station;
   a communication error between the product and the wireless transfer station; and
   a cell imbalance of one or more batteries in the wireless transfers station.

* * * * *